US010759754B2

(12) United States Patent
Bérubé et al.

(10) Patent No.: US 10,759,754 B2
(45) Date of Patent: Sep. 1, 2020

(54) AMINOBENZOIC ACID DERIVATIVES FOR USE AS ANTI-INFLAMMATORY AGENTS, ANTI-METASTATIC AGENTS AND/OR ANTICANCER AGENTS

(71) Applicant: 3R VALO, S.E.C., Montréal (CA)

(72) Inventors: Gervais Bérubé, Trois-Rivières (CA); Carlos Reyes-Moreno, Trois-Rivières (CA)

(73) Assignee: 3R VALO, S.E.C., Montréal (CA)

( * ) Notice: Subject to any disclaimer, the term of this patent is extended or adjusted under 35 U.S.C. 154(b) by 0 days.

(21) Appl. No.: 16/091,721

(22) PCT Filed: Apr. 10, 2017

(86) PCT No.: PCT/CA2017/050432
§ 371 (c)(1),
(2) Date: Oct. 5, 2018

(87) PCT Pub. No.: WO2017/177316
PCT Pub. Date: Oct. 19, 2017

(65) Prior Publication Data
US 2019/0127325 A1    May 2, 2019

Related U.S. Application Data

(60) Provisional application No. 62/320,654, filed on Apr. 11, 2016.

(51) Int. Cl.
| | | |
|---|---|---|
| C07D 207/452 | (2006.01) | |
| C07D 207/404 | (2006.01) | |
| A61P 35/00 | (2006.01) | |
| C07D 209/48 | (2006.01) | |
| C07D 207/456 | (2006.01) | |

(52) U.S. Cl.
CPC .......... *C07D 207/452* (2013.01); *A61P 35/00* (2018.01); *C07D 207/404* (2013.01); *C07D 207/456* (2013.01); *C07D 209/48* (2013.01)

(58) Field of Classification Search
None
See application file for complete search history.

(56) References Cited

U.S. PATENT DOCUMENTS 3,046,301 A    7/1962 Phillips et al.

FOREIGN PATENT DOCUMENTS

CA    2586080    8/2006

OTHER PUBLICATIONS

Mustafavi et al, Pharm Dev Technol, 2015; 20(7): 845-853.*
Alderton GK, "The tumor microenvironment drives metastasis", Nat. Rev. Cancer 16, 199 (2016). (The year of publication is sufficiently earlier than the effective U.S. filing date so that the particular month of publication is not an issue).
Am et al., "Antibody therapy of cancer", Nat. Rev. Cancer 12, 278-287 (2012). (The year of publication is sufficiently earlier than the effective U.S. filing date so that the particular month of publication is not an issue).
Auwerx J., "The human leukemia cell line, THP-1: A multifacetted model for the study of monocyte-macrophage differentiation", Experientia, 47, 22-31 (1991). (The year of publication is sufficiently earlier than the effective U.S. filing date so that the particular month of publication is not an issue).
Baumann et al., "Radiation oncology in the era of precision medicine", Nat. Rev. Cancer 16, 234-249 (2016). (The year of publication is sufficiently earlier than the effective U.S. filing date so that the particular month of publication is not an issue).
Belgorosky et al., "Inhibition of nitric oxide is a good therapeutic target for bladder tumors that express iNOS", Nitric Oxide, 36, 11-18 (2014). (The year of publication is sufficiently earlier than the effective U.S. filing date so that the particular month of publication is not an issue).
Carmichael et al., "Evaluation of a Tetrazolium-based Semiautomated Colorimetric Assay: Assessment of Radiosensitivity", Cancer Res., 47, 943-946 (1987). (The year of publication is sufficiently earlier than the effective U.S. filing date so that the particular month of publication is not an issue).
Daigneault et al., "The Identification of Markers of Macrophage Differentiation in PMA-Stimulated THP-1 Cells and Monocyte-Derived Macrophages", PloS one, 5, 0008668 (2010). (The year of publication is sufficiently earlier than the effective U.S. filing date so that the particular month of publication is not an issue).
Dallagi et al., "The activating effect of IFN-γ on monocytes/macrophages is regulated by the LIF-trophoblast-IL-10 axis via Stat1 inhibition and Stat3 activation", Cell. Mol. Immunol., 12, 326-341 (2015). (The year of publication is sufficiently earlier than the effective U.S. filing date so that the particular month of publication is not an issue).
Dufresne et al., "Pro-inflammatory type-1 and anti-inflammatory type-2 macrophages differentially modulate cell survival and invasion of human bladder carcinoma T24 cells", Mol. Immunol., 48, 1556-1567 (2011). (The year of publication is sufficiently earlier than the effective U.S. filing date so that the particular month of publication is not an issue).
Dumas et al., "CD40 pathway activation reveals dual function for macrophages in human endometrial cancer cell survival and invasion", Cancer Immunol. Immunother., 62, 273-283 (2013). (The year of publication is sufficiently earlier than the effective U.S. filing date so that the particular month of publication is not an issue).

(Continued)

*Primary Examiner* — Kamal A Saeed
(74) *Attorney, Agent, or Firm* — Bereskin & Parr LLP/S.E.N.C.R.L., s.r.l.

(57) ABSTRACT

There are provided compounds of formula (I) in which $R_2$, $R_2$, $R_3$, $R_4$ and Q can represent various different possibilities. These compounds can be useful as anticancer agents as well as anti-inflammatory agents, anti-proliferative agents and/or anti-metastatic agents.

15 Claims, 28 Drawing Sheets

(56) References Cited

OTHER PUBLICATIONS

Fabris et al., "Cytogenetic characterization of the murine bladder cancer model MB49 and the derived invasive line MB49-I", Cancer Genet., 205, 168-176 (2012). (The year of publication is sufficiently earlier than the effective U.S. filing date so that the particular month of publication is not an issue).

Willner et al., "(6-Maleimidocaproyl)hydrazone of Doxorubicin—A New Derivative for the Preparation of Immunoconjugates of Doxorubicin", Bioconjug. Chem. 4, 521-527 (1993). (The year of publication is sufficiently earlier than the effective U.S. filing date so that the particular month of publication is not an issue).

Al-Azzawi et al., "Synthesis and Antimicrobial Activity of New Succinimides Bearing Different Heterocycles", IJRPC 2014, 4(4), 755-762. (The year of publication is sufficiently earlier than the effective U.S. filing date so that the particular month of publication is not an issue).

Bhat et al., "Design and Synthesis of N-Arylphthalimdes as Inhibitors of Glucocorticoid-Induced TNF Receptor-Related Protein, Proinflammatory Mediators, and Cytokines in Carrageenan-Induced Lung Inflammation", Journal of Medicinal Chemistry 2015, 58, 8850-8867. (The year of publication is sufficiently earlier than the effective U.S. filing date so that the particular month of publication is not an issue.

Desai et al., "Study of Novel Pyrrolidine Compounds", Journal of Chemical and Pharmaceutical Research, 2014, 6(6):2624-2627. (The year of publication is sufficiently earlier than the effective U.S. filing date so that the particular month of publication is not an issue).

Fahmy et al., "Novel Antimicrobial Organic Thermal Stabilizer and Co-Stabilizer for Rigid PVC", Molecules 2012, 17, 7927-7940. (The year of publication is sufficiently earlier than the effective U.S. filing date so that the particular month of publication is not an issue).

Hamelin-Mornssette et al., "Identification of an anti-inflammatory derivative with anti-cancer potential: The impact of each of its structural components on inflammatory responses in macrophages and bladder cancer cells", European Journal of Medicinal Chemistry 96 (2015) 259-268. (The year of publication is sufficiently earlier than the effective U.S. filing date so that the particular month of publication is not an issue.

Mane et al., "Stimuli responsive nanocarrier for an effective delivery of multi-frontline tuberculosis drugs", Polym. Chem., 2014, 5, 2725-2735. (The year of publication is sufficiently earlier than the effective U.S. filing date so that the particular month of publication is not an issue).

Mohamed et al., "Thermogravimetric analysis in the evaluation of the inhibition of degradation of rigid poly(vinyl chloride) using biologically active phthalimido aromatic hydrazide derivatives", Polymer Degradation and Stability 128 (2016) 46-54. (The year of publication is sufficiently earlier than the effective U.S. filing date so that the particular month of publication is not an issue).

Tasler et al., "Non-competitive inhibitors of metabotropic glutamate receptor 5 (mGTuR5)", Bioorganic & Medicinal Chemistry Letters 15 (2005) 2876-2880. (The year of publication is sufficiently earlier than the effective U.S. filing date so that the particular month of pubication is not an issue).

Heindel el al., "A Novel Heterobifunclional Linker for Formyl to Thiol Coupling", Bioconjug. Chem., 2, 427-430 (1991). (The year of publication is sufficiently earlier than the effective U.S. filing date so that the particular month of publication is not an issue).

Lau et al., "Conjugation of Doxorubicin to Monoclonal Anti-carcinoembryonic Antigen Antibody via Novel Thiol-directed Cross-linking Reagents", Bioorg. Med. Chem., 3, 1299-1304 (1995). (The year of publication is sufficiently earlier than the effective U.S. filing date so that the particular month of publicalion is not an issue).

Lau et al., "Novel Doxorubicin-Monoclonal Anti-carcinoembryonic Antigen Antibody Immunoconjugate Activity in vitro", Bioorg. Med. Chem., 3, 1305-1312 (1995). (The year of publication is sufficiently earlier than the effective U.S. filing date so that the particular month of publication is not an issue).

Leduc et al., "Leukemia Inhibitory Factor Regulates Differentiation of Trophoblastlike BeWo Cells Through the Activation of JAK/STAT and MAPK3/1 MAP Kinase-Signaling Pathways", Biol. Reprod., 86, 54, 1-10 (2012). (The year of publication is sufficiently earlier than the effective U.S. filing date so that the particular month of publication is not an issue).

Lemaire et al., "Study of Macrophage Functions in Munne J774 Cells and Human Activated THP-1 Cells Exposed to Oritavancin, a Lipoglycopeptide with High Cellular Accumulation", Antimicrobial agents and chemotherapy, 58, 2059-2066 (2014). (The year of publication is sufficiently earlier than the effective U.S. filing date so that the particular month of publication is not an issue.

Menon et al., "Fluorescence-Based Quantitative Scratch Wound Healing Assay Demonstrating the Role of MAPKAPK-2/3 in Fibroblast Migration", Cell. Motil. Cytoskeleton, 66, 1041-1047 (2009). (The year of publication is sufficiently earlier than the effective U.S. filing date so that the particular month of publication is not an issue).

Qin, "the use of THP-1 cells as a model for mimicking the function and regulation of monocytes and macrophages in the vasculature", Atherosclerosis, 221, 2-11 (2012). (The year of publication is sufficiently earlier than the effective U.S. filing date so that the particular month of publication is not an issue).

Steeg PS, "Targeting metastasis", Nat. Rev. Cancer 16, 201-218 (2016). (The year of publication is sufficiently earlier than the effective U.S. filing date so that the particular month of publication is not an issue).

Still et al., "Rapid Chromatographic Technique for Preparative Separations with Moderate Resolution", J. Org. Chem., 43, 2923-2925 (1978). (The year of publication is sufficiently earlier than the effective U.S. filing date so that the particular month of publication is not an issue).

Taha et al., "Synthesis of novel inhibitors of a-glucosidase based on the benzothiazole skeleton containing benzohydrazide moiety and their molecular docking studies", European Journal of Medicinal Chemistry, 92, 387-400 (2015). (The year of publication is sufficiently earlier than the effective U.S. filing date so that the particular month of publication is not an issue.

Vanneman et al., "Combining Immunotherapy and Targeted Therapies in Cancer Treatment", Nat. Rev. Cancer 12, 237-251 (2012). (The year of publication is sufficiently earlier than the effective U.S. filing date so that the particular month of publication is not an issue).

* cited by examiner (a)

(b)

(a)

4

8 (R = CH₃)

10 (R = CH₃)

11 (R = CH₃)

(b)

AMINOBENZOIC ACID DERIVATIVES FOR USE AS ANTI-INFLAMMATORY AGENTS, ANTI-METASTATIC AGENTS AND/OR ANTICANCER AGENTS

CROSS REFERENCE TO RELATED APPLICATION

The present application is a 35 USC 371 national stage entry of PCT/CA2017/050432 and which claims priority to U.S. provisional application No. 62/320,654 filed on Apr. 11, 2016. These documents are hereby incorporated by reference in their entirety.

FIELD OF THE DISCLOSURE

This disclosure relates to the field of active agents. More particularly, this disclosure relates to anti-inflammatory agents, anti-metastatic agents, anti-proliferative agents and anticancer agents. The present disclosure also relates to methods for treating cancers using these agents.

BACKGROUND OF THE DISCLOSURE

There are several methods used to treat cancer.[1] The most common are: surgery, chemotherapy, radiation therapy, targeted therapy and immunotherapy.[1-6] Other procedures are based on stem cell transplant, photodynamic therapy, and cryogenic therapy.[1] Lasers are nowadays a useful tool during surgery of localized cancers. Many of these methods are quite effective. However, most present important side effects.[7,8] Hence, the need to discover alternative therapeutics and treatment modalities. Particularly, compounds and treatment protocols that could simultaneously attack cancer on diverse fronts (initiation, propagation, metastasis etc.) are of great interest.

Urothelial bladder cancer (UBC) is the fifth most common malignancy of all cancers in North America. Although most of detectable tumors are initially non-muscle-invasive and are generally curable by means of chirurgical resection, 27-30% of them exhibit a lethal phenotype characterized by high histological grade and muscle invasion. Recent studies have also provided ample evidence that UBC intravesical therapy response is influenced by infiltration of major inflammatory cells (mainly macrophages) and activation of key inflammatory mediators (including the cytokines TNFα and IL6 and the transcription factors NFκB and STAT3). Considering the critical functions of inflammatory mediators in UBC growth, dissemination and resistance to cell death, they may represent potential drug targets to improve the efficacy of immunotherapy and chemotherapy agents.

SUMMARY OF THE DISCLOSURE

According to one aspect, there are included compounds of formula (I):

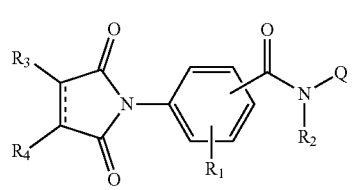

(I)

wherein $R_1$ is H, alkyl or halogen;

$R_2$ is H, or a substituted or unsubstituted member chosen from acetyl, propiolyl, butyryl, isobutyryl and benzoyl;

Q is $Q_A$ or $Q_B$;

$Q_A =$

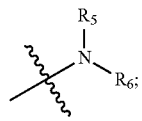

$Q_B =$

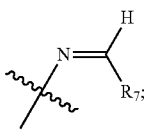

⫽ = a single bond or a double bond;

$R_5$ is H, or a substituted or unsubstituted member chosen from acetyl, propiolyl, butyryl, isobutyryl and benzoyl;

$R_6$ is H, Boc, or a substituted or unsubstituted member chosen from acetyl, propiolyl, butyryl, isobutyryl and benzoyl;

$R_7$ is a substituted or unsubstituted member chosen from $C_1$-$C_8$ alkyl, $C_3$-$C_8$ cycloalkyl, phenyl, furanyl, thiophenyl, pyridinyl, naphthyl, quinolyl and isoquinolyl;

$R_3$ and $R_4$ are independently chosen from H, —$SR_8$ and —$NR_9R_{10}$, or $R_3$ and $R_4$ are joined together to form a 5-7 membered ring that optionally comprises an heteroatom chosen from N, S and O;

$R_8$ is H, $C_1$-$C_8$ alkyl, —$(CH_2)_n$NHBoc, or —$(CH_2)_n$NH$_2$ wherein n=1 to 6;

$R_9$ is H or $C_1$-$C_8$ alkyl;

$R_{10}$ is H, $C_1$-$C_8$ alkyl, acetyl, propiolyl, butyryl, isobutyryl, or benzoyl;

wherein $R_2$, $R_5$, $R_6$ and $R_7$, when substituted, are substituted with at least one substituent chosen from —$OR_9$, —F, —Cl, —Br, —I, acetyl, propiolyl, butyryl, isobutyryl, benzoyl, —$NO_2$, $C_1$-$C_8$ alkyl, methoxycarbonyl-, or alkyloxycarbonyl-;

or an enantiomer, diastereoisomer, racemic mixture, pharmaceutically acceptable salt, solvate or prodrug thereof.

According to another aspect, there is provided compounds of formulae (IIA), (IIB) or (IIC):

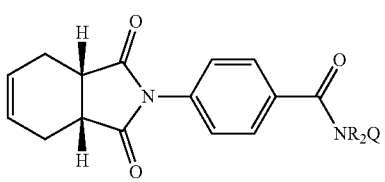

(IIA)

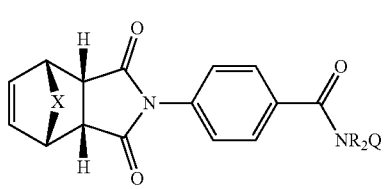 (IIB)

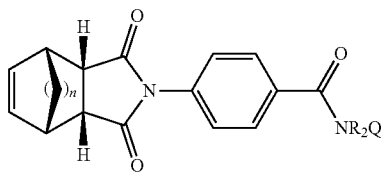 (IIC)

wherein
Q is $Q_A$ or $Q_B$;
$Q_A=$

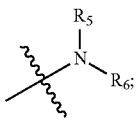

$Q_B=$

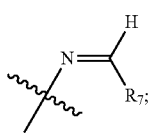

$R_2$ is H, or a substituted or unsubstituted member chosen from acetyl, propiolyl, butyryl, isobutyryl and benzoyl;
$R_5$ is H, or a substituted or unsubstituted member chosen from acetyl, propiolyl, butyryl, isobutyryl and benzoyl;
$R_6$ is H, Boc, or a substituted or unsubstituted member chosen from acetyl, propiolyl, butyryl, isobutyryl and benzoyl;
$R_7$ is a substituted or unsubstituted member chosen from $C_1$-$C_8$ alkyl, $C_3$-$C_8$ cycloalkyl, phenyl, furanyl, thiophenyl, pyridinyl, naphthyl, quinolyl and isoquinolyl;
$R_9$ is H or $C_1$-$C_8$ alkyl;
X is O, S or $NR_2$;
n is 1, 2 or 3;
wherein $R_2$, $R_5$, $R_6$ and $R_7$, when substituted, are substituted with at least one substituent chosen from —$OR_9$, —F, —Cl, —Br, —I, acetyl, propiolyl, butyryl, isobutyryl, benzoyl, —$NO_2$, $C_1$-$C_8$ alkyl, methoxycarbonyl-, or alkyloxycarbonyl-;
or an enantiomer, diastereoisomer, racemic mixture, pharmaceutically acceptable salt, solvate or prodrug thereof.

According to another aspect, there is included a composition comprising a pharmaceutically acceptable carrier and at least one compound of the present disclosure.

According to another aspect, there is included a method for treating cancer or at least one cancer chosen from breast cancer, uterine cancer, ovarian cancer, prostate cancer, bladder cancer, and melanoma, the method comprising administering to a subject in need thereof an effective amount of at least one compound of the present disclosure.

According to another aspect, there is included a method for reducing the risks of developing cancer or for reducing the risk of developing at least one cancer in a subject, the cancer being, for example, chosen from breast cancer, uterine cancer, ovarian cancer, prostate cancer, bladder cancer, and melanoma, the method comprising administering to the subject an effective amount of at least one compound of the present disclosure.

According to another aspect, there is included a method for inhibiting cancer cell growth, the method comprising administering to a subject in need thereof an effective amount of at least one compound of the present disclosure. For example, the cancer can be chosen from breast cancer, uterine cancer, ovarian cancer, prostate cancer, bladder cancer, and melanoma.

According to another aspect, there is included a method for inhibiting cancer cell growth, the method comprising contacting cancer cells with an effective amount of at least one compound of the present disclosure. For example, the cancer can be chosen from breast cancer, uterine cancer, ovarian cancer, prostate cancer, bladder cancer, and melanoma.

According to another aspect, there is included a method for inhibiting cancer tumor growth and/or cancer tumor size, the method comprising administering to a subject in need thereof an effective amount of at least one compound of the present disclosure. For example, the cancer can be chosen from breast cancer, uterine cancer, ovarian cancer, prostate cancer, bladder cancer, and melanoma.

According to another aspect, there is included a method for decreasing and/or preventing cancer tumor metastases, the method comprising administering to a subject in need thereof an effective amount of at least one compound of the present disclosure. For example, the cancer can be chosen from breast cancer, uterine cancer, ovarian cancer, prostate cancer, bladder cancer, and melanoma.

According to another aspect, there is included the use of at least one compound of the present disclosure for treating cancer or for treating at least one cancer chosen from breast cancer, uterine cancer, ovarian cancer, prostate cancer, bladder cancer, and melanoma.

According to another aspect, there is included the use of at least one compound of the present disclosure for reducing the risks of developing cancer or for reducing the risks of developing at least one cancer chosen from breast cancer, uterine cancer, ovarian cancer, prostate cancer, bladder cancer, and melanoma.

According to another aspect, there is included the use of at least one compound of the present disclosure for inhibiting cancer cell growth. For example, the cancer can be chosen from breast cancer, uterine cancer, ovarian cancer, prostate cancer, bladder cancer, and melanoma.

According to another aspect, there is included the use of at least one compound of the present disclosure for inhibiting cancer tumor growth and/or cancer tumor size of at least one cancer chosen from breast cancer, uterine cancer, ovarian cancer, prostate cancer, bladder cancer, and melanoma.

According to another aspect, there is included the use of at least one compound of the present disclosure for decreasing and/or preventing cancer tumor metastases of at least one cancer chosen from breast cancer, uterine cancer, ovarian cancer, prostate cancer, bladder cancer, and melanoma.

According to another aspect, there is included the use of at least one compound of the present disclosure in the manufacture of a medicament for treating cancer or for treating at least one cancer chosen from breast cancer, uterine cancer, ovarian cancer, prostate cancer, bladder cancer, and melanoma.

According to another aspect, there is included the use of at least one compound of the present disclosure in the manufacture of a medicament for reducing the risks of developing cancer or for reducing the risks of developing at least one cancer chosen from breast cancer, uterine cancer, ovarian cancer, prostate cancer, bladder cancer, and melanoma.

According to another aspect, there is included the use of at least one compound of the present disclosure in the manufacture of a medicament for inhibiting cancer cell growth. For example, the cancer can be chosen from breast cancer, uterine cancer, ovarian cancer, prostate cancer, bladder cancer, and melanoma.

According to another aspect, there is included the use of at least one compound of the present disclosure in the manufacture of a medicament for inhibiting cancer tumor growth and/or cancer tumor size. For example, the cancer can be chosen from breast cancer, uterine cancer, ovarian cancer, prostate cancer, bladder cancer, and melanoma.

According to another aspect, there is included the use of at least one compound of the present disclosure in the manufacture of a medicament for decreasing and/or preventing cancer tumor metastases. For example, the cancer can be chosen from breast cancer, uterine cancer, ovarian cancer, prostate cancer, bladder cancer, and melanoma.

BRIEF DESCRIPTION OF FIGURES

The following drawings represent in a non-limitative manner examples of specific embodiments in which.

DETAILED DESCRIPTION OF THE DISCLOSURE

Figure 1:
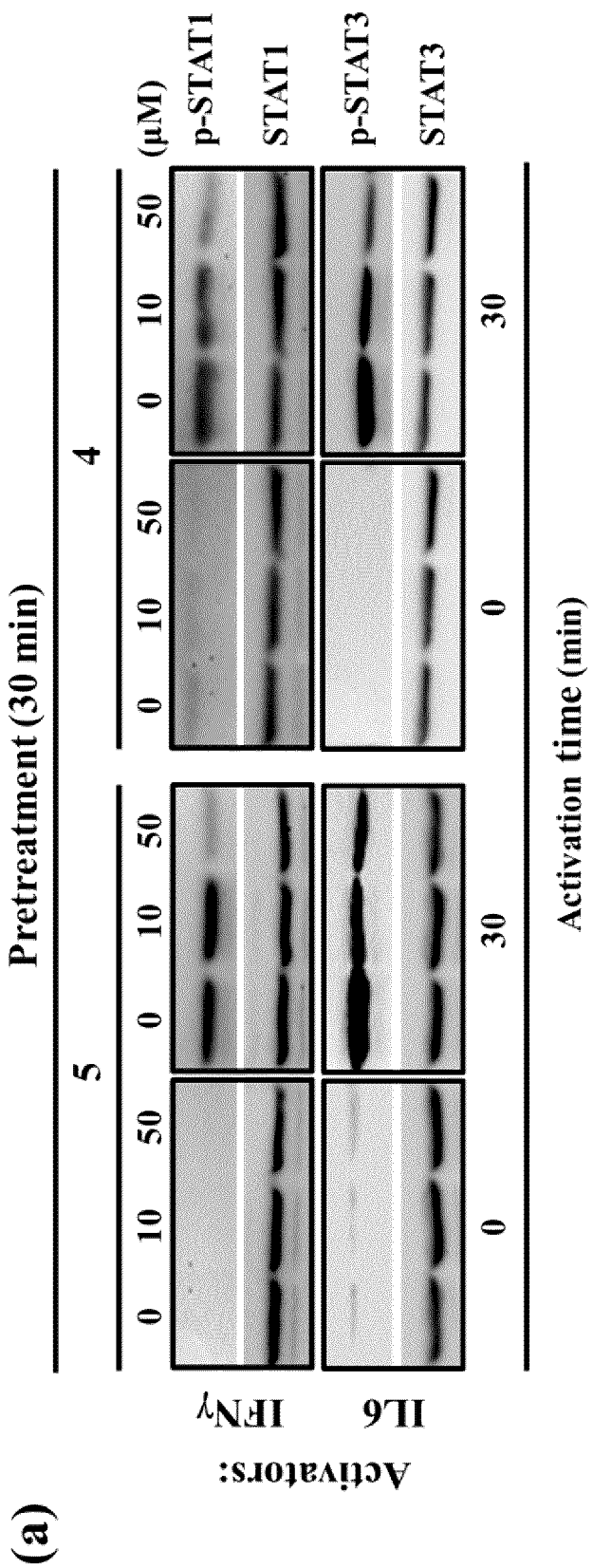
FIG. 1 represents images (a) and graphical analysis (b) showing Western blot analysis to determine the expression level of phosphorylated STAT1 and STAT3 in human macrophages (Mϕs) pretreated for 30 min with vehicle (DMSO) or compounds 4 and 5 (both at 0, 10 and 50 µM), and then washed and recovered immediately (t=0) or after 30 min of activation with either 50 U/mL IFNγ or 25 ng/mL IL6. The ratio of phosphorylated/no phosphorylated proteins was calculated from densitometric analysis of each sample to evaluate the relative activation of pSTAT1 or pSTAT3. Compounds 4 and 5 efficiently inhibited IFNγ-induced STAT1 activation and IL6-induced STAT3 activation. *$p<0.05$ and **$p<0.01$ denote significant differences between treatments.
Figure 1:
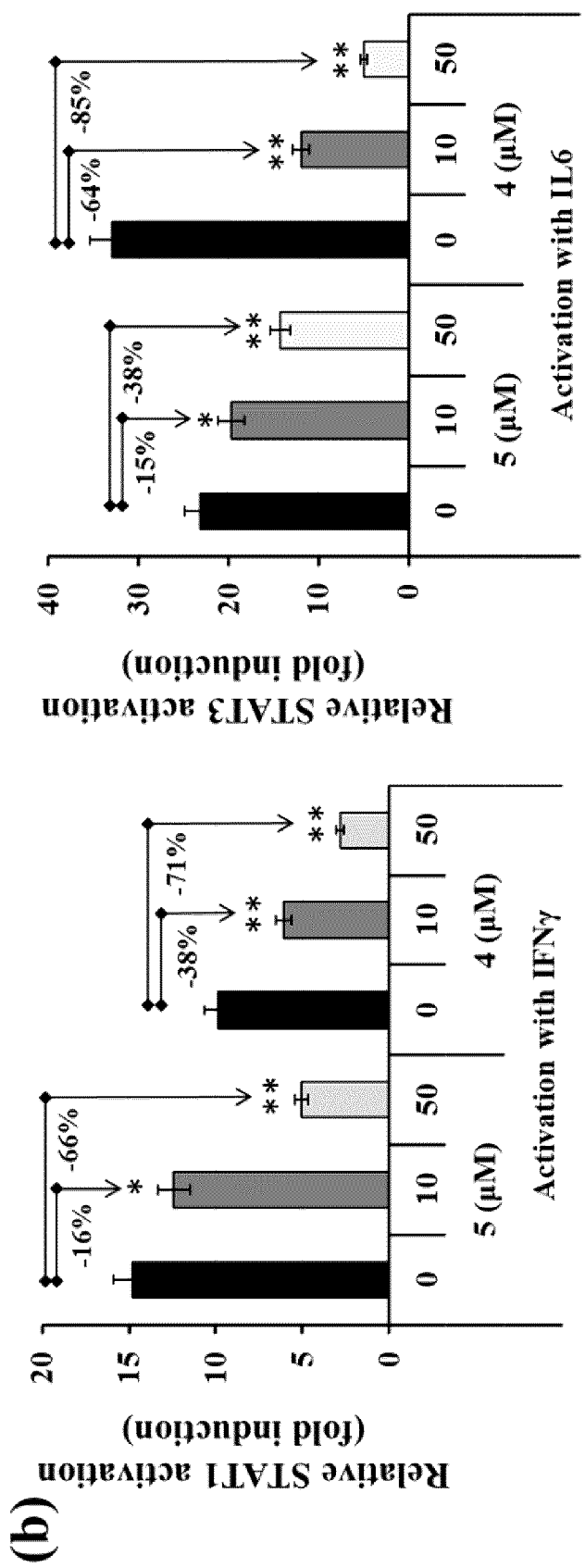

The present disclosure concerns the discovery of small aminobenzoic acid derivatives showing anti-inflammatory, anti-metastatic, anti-proliferative and anticancer properties in vitro and in vivo. It describes the synthetic methodology to make these derivatives from readily available ortho-, meta- and para-benzoic acid and their biological applications for the treatment of a several types of cancers. In addition, this disclosure relates to different pharmaceutical compositions comprising these compounds. The compounds and the pharmaceutical composition of this disclosure have been shown to possess anticancerous activity on various types of cancers. Furthermore, this disclosure provides novel treatment modalities against cancer. The unique biological properties of these compounds may be advantageously used to provide compounds with anticancer activity against cancers including but not limited to breast, prostate, ovarian and bladder cancers.

The term a "therapeutically effective amount", "effective amount" or a "sufficient amount" of a compound of the present disclosure is a quantity sufficient to, when administered to the subject, including a mammal, for example a human, effect beneficial or desired results, including clinical results, and, as such, an "effective amount" or synonym thereto depends upon the context in which it is being applied. For example, in the context of treating cancer, for example, it is an amount of the compound sufficient to achieve such treatment of the cancer as compared to the response obtained without administration of the compound. The amount of a given compound of the present disclosure that will correspond to an effective amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, a "therapeutically effective amount", "effective amount" or a "sufficient amount" of a compound of the present disclosure is an amount which inhibits, suppresses or reduces a cancer (e.g., as determined by clinical symptoms or the amount of cancerous cells) in a subject as compared to a control.

The term "subject" as used herein includes all members of the animal kingdom including human. According to one embodiment, the subject is a human.

The term "alkyl" as used herein means straight and/or branched chain, saturated alkyl groups containing from one to n carbon atoms and includes (depending on the identity of n) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, wherein n is the maximum number of carbon atoms in the group.

The expression "an alkyl component of a naturally occurring amino acid" as used herein refers to the portion of a naturally occurring amino acid that is comprised between the carbon of the carbonyl group of the amino acid and the nitrogen atom of the amino acid.

The expression "compound(s) of the present disclosure" as used in the present document refers to compounds of formulae I, IA, IB, IC, ID, IE, IIA, IIB and IIC presented in the present disclosure, isomers thereof, such as stereoisomers (for example, enantiomers, diastereoisomers, including racemic mixtures) or tautomers, or to pharmaceutically acceptable salts, solvates, hydrates and/or prodrugs of these compounds, isomers of these latter compounds, or racemic mixtures of these latter compounds. The expression "compound(s) of the present disclosure" also refers to mixtures of the various compounds or variants mentioned in the present paragraph.

The term "halogen" as used herein comprises fluoro, chloro, bromo and iodo.

It is to be clear that the present disclosure includes isomers, racemic mixtures, pharmaceutically acceptable salts, solvates, hydrates and prodrugs of compounds described therein and mixtures comprising two or more of such compounds.

The compounds of the disclosure may have at least one asymmetric centre. Where the compounds according to the present document possess more than one asymmetric centre, they may exist as diastereomers. It is to be understood that all such isomers and mixtures thereof in any proportion are encompassed within the scope of the present disclosure. It is to be understood that while the stereochemistry of the compounds of the present disclosure may be as provided for in any given compound listed herein, such compounds of the disclosure may also contain certain amounts (for example less than 30%, less than 20%, less than 10%, or less than 5%) of compounds of the present disclosure having alternate stereochemistry.

The term "suitable", as in for example, "suitable counter anion" or "suitable reaction conditions" means that the selection of the particular group or conditions would depend on the specific synthetic manipulation to be performed and the identity of the molecule but the selection would be well within the skill of a person trained in the art. All process steps described herein are to be conducted under conditions suitable to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The expression "pharmaceutically acceptable" means compatible with the treatment of subjects such as animals or humans.

The expression "pharmaceutically acceptable salt" means an acid addition salt or basic addition salt which is suitable for or compatible with the treatment of subjects such as animals or humans.

The expression "pharmaceutically acceptable acid addition salt" as used herein means any non-toxic organic or inorganic salt of any compound of the present disclosure, or any of its intermediates. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as para-toluene sulfonic and methanesulfonic acids. Either the mono or di-acid salts can be formed, and such salts may exist in either a hydrated, solvated or substantially anhydrous form. In general, the acid addition salts of the compounds of the present disclosure are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of the compounds of the present disclosure, for laboratory use, or for subsequent conversion to a pharmaceutically acceptable acid addition salt. In embodiments of the present disclosure, the pharmaceutically acceptable acid addition salt is the hydrochloride salt.

The term "pharmaceutically acceptable basic addition salt" as used herein means any non-toxic organic or inorganic base addition salt of any acid compound of the disclosure, or any of its intermediates. Acidic compounds of the disclosure that may form a basic addition salt include, for example, where R is $CO_2H$. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art. Other non-pharmaceutically acceptable basic addition salts, may be used, for example, in the isolation of the compounds of the disclosure, for laboratory use, or for subsequent conversion to a pharmaceutically acceptable acid addition salt.

The formation of a desired compound salt is achieved using standard techniques. For example, the neutral compound is treated with an acid or base in a suitable solvent and the formed salt is isolated by filtration, extraction or any other suitable method.

The term "solvate" as used herein means a compound of the present disclosure, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates of the compounds of the present disclosure will vary depending on the compound and the solvate. In general, solvates are formed by dissolving the compound in the appropriate solvent and isolating the solvate by cooling or using an antisolvent. The solvate is typically dried or azeotroped under ambient conditions.

Compounds of the present disclosure include prodrugs. In general, such prodrugs will be functional derivatives of these compounds which are readily convertible in vivo into the compound from which it is notionally derived. Prodrugs of the compounds of the present disclosure may be conventional esters formed with available hydroxy, or amino group. For example, an available OH or nitrogen in a compound of the present disclosure may be acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters. In certain instances, the prodrugs of the compounds of the present disclosure are those in which one or more of the hydroxy groups in the compounds is masked as groups which can be converted to hydroxy groups in vivo. Conventional procedures for the selection and preparation of suitable prodrugs are described, for example, in "Design of Prodrugs" ed. H. Bundgaard, Elsevier, 1985.

Compounds of the present disclosure include radiolabeled forms, for example, compounds labeled by incorporation within the structure $^2H$, $^3H$, $^{14}C$, $^{15}N$, or a radioactive halogen such as $^{125}I$. A radiolabeled compound of the compounds of the present disclosure may be prepared using standard methods known in the art.

As used herein, and as well understood in the art, "treatment" or "treating" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" or "treating" can also mean prolonging survival as compared to expected survival if not receiving treatment.

"Palliating" a disease or disorder, means that the extent and/or undesirable clinical manifestations of a disorder or a disease state are lessened and/or time course of the progression is slowed or lengthened, as compared to not treating the disorder.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

In an embodiment of the present disclosure, there are included compounds of formula (IA):

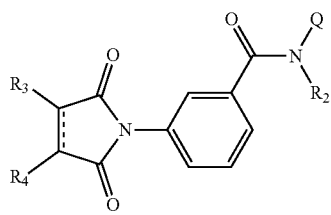

wherein $R_2$, $R_3$, $R_4$ and Q are as previously defined.

In another embodiment of the present disclosure, there are included compounds of formula (IB):

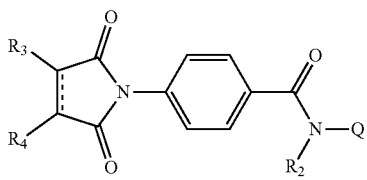

wherein $R_2$, $R_3$, $R_4$ and Q are as previously defined.

In a further embodiment of the present disclosure, there are included compounds of formula (IC):

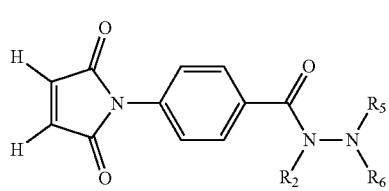

wherein $R_2$, $R_5$ and $R_6$ are as previously defined.

In still a further embodiment of the present disclosure, there are included compounds of formula (ID):

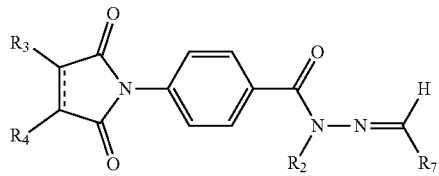

wherein $R_2$, $R_3$, $R_4$ and $R_7$ are as previously defined.

In still a further embodiment of the present disclosure, there are included compounds of formula (IE):

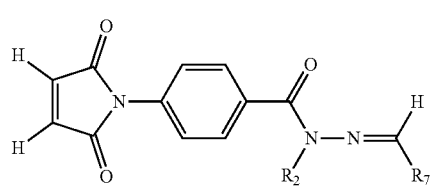

wherein $R_2$ and $R_7$ are as previously defined.

In still a further embodiment of the present disclosure, $R_2$ is H, unsubstituted member chosen from acetyl and propiolyl;

Q is $Q_4$;

$R_5$ is H, unsubstituted member chosen from acetyl and propiolyl; and $R_6$ is Boc, H, or an unsubstituted member chosen from acetyl and propiolyl.

In still a further embodiment of the present disclosure, $R_2$ is H or unsubstituted member chosen from acetyl and propiolyl; and $R_7$ is an unsubstituted member chosen from $C_1$-$C_8$ alkyl, $C_3$-$C_6$ cycloalkyl, phenyl, furanyl, thiophenyl, pyridinyl, naphthyl, quinolyl and isoquinolyl.

For example, in a further embodiment of the present disclosure, the compound of formula I is as previously defined with the proviso that the compound is different from

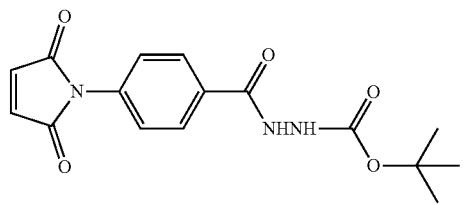

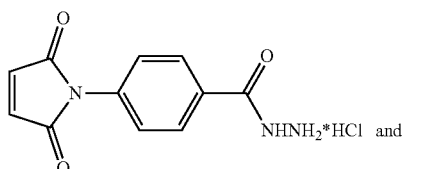

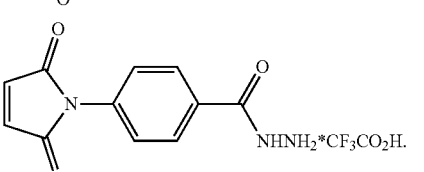

However, according to an embodiment the above three excluded compounds are not to be excluded from the scope of the various uses and methods as previously described.

According to another embodiment, the above three excluded compounds are to be excluded from the scope of the various uses and methods as previously described.

In still a further embodiment of the present disclosure, there are included compounds of the following formulas:
4a
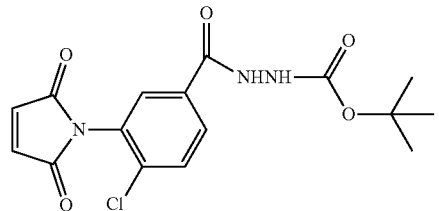
4b
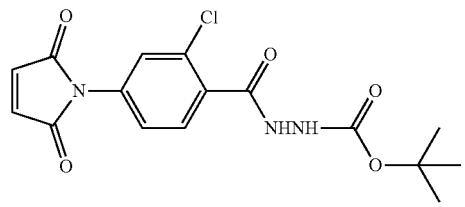
8
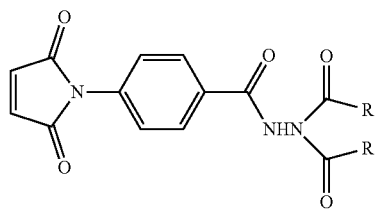
10
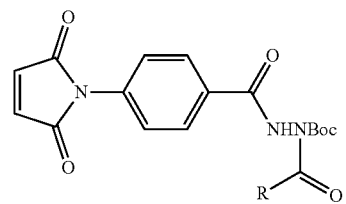
(R = CH₃)
11
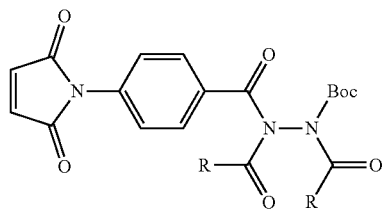
(R = CH₃)
12
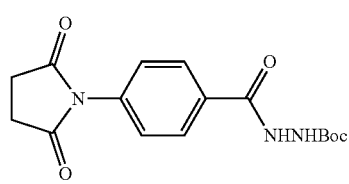
13
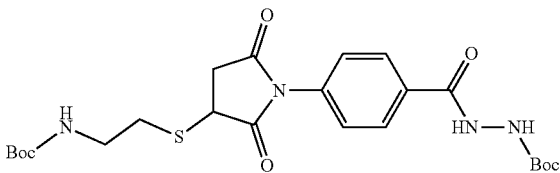
For example, the compound can be chosen from
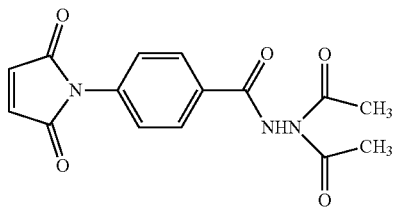
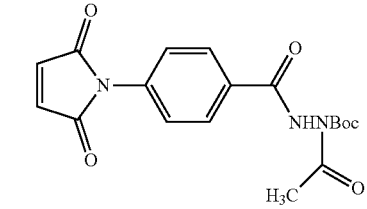
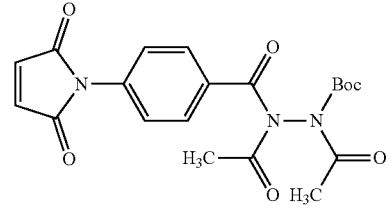
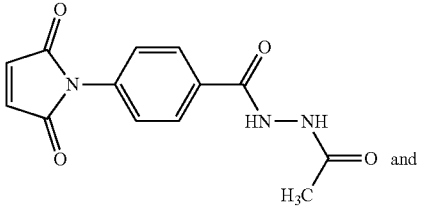
and
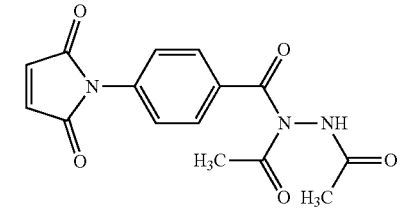
For example, the compounds can be chosen from
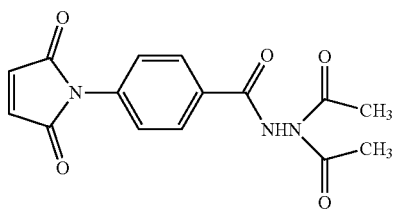

-continued
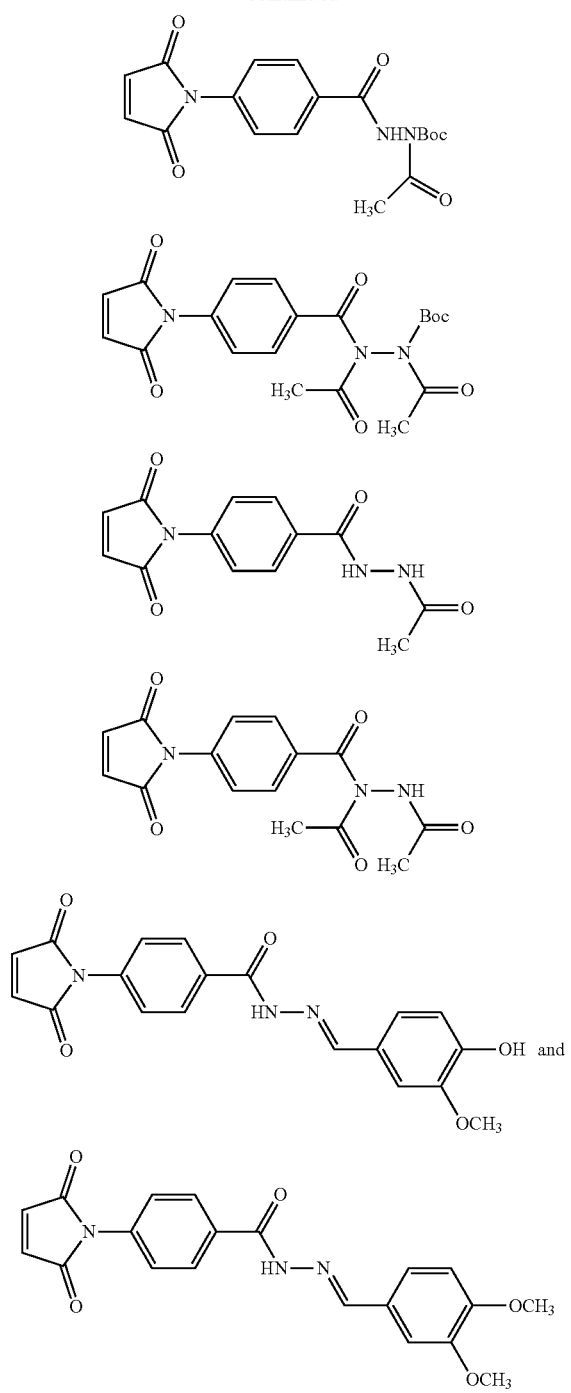
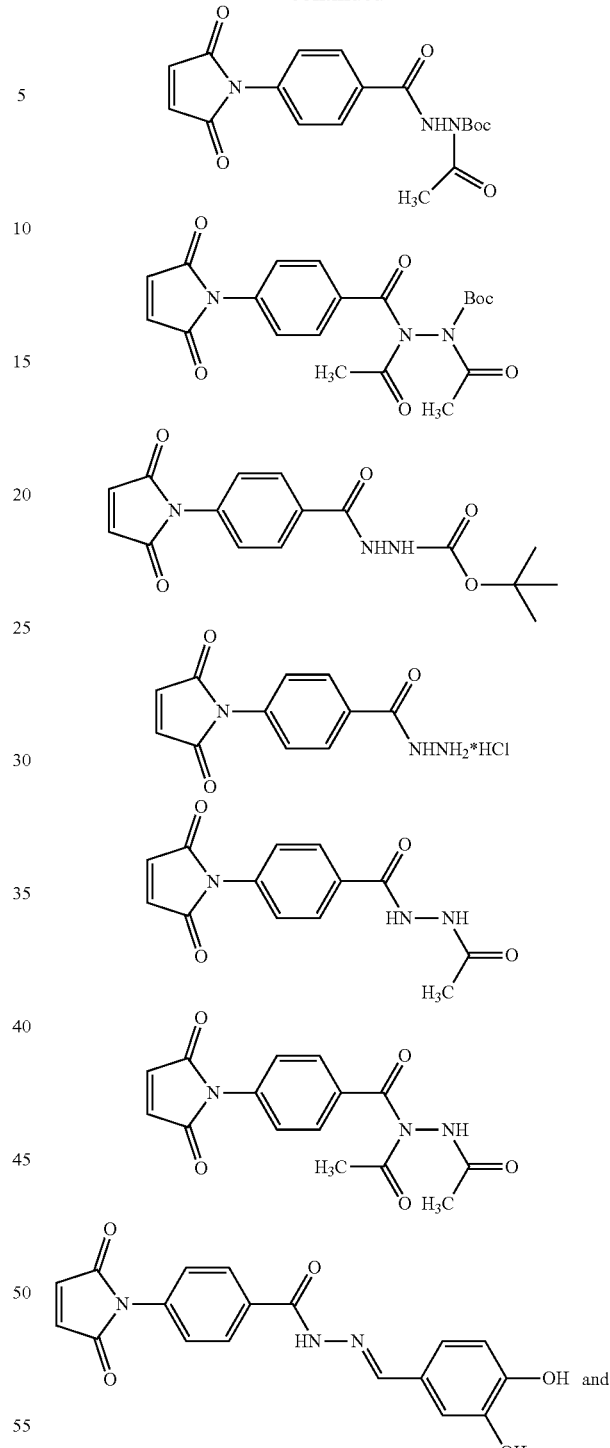
For example, the compounds can be chosen from
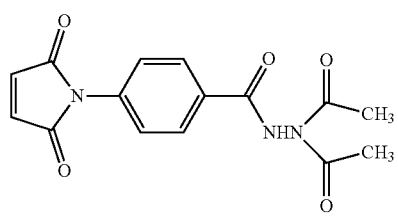
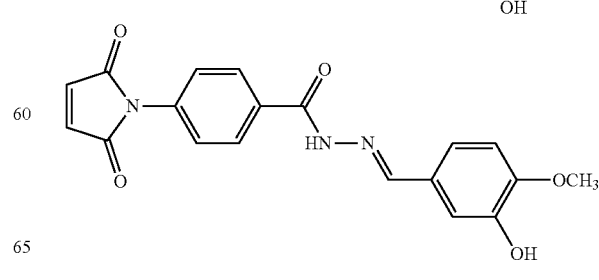

For example, the compounds can be chosen from

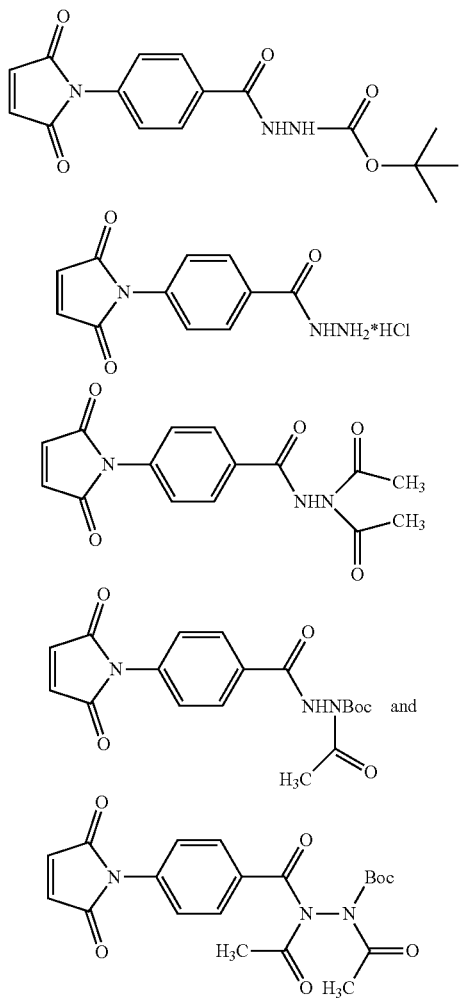

Schemes 1 to 4 represent examples of synthetic routes used for the preparation of the compounds of the present disclosure. The reaction conditions of each step are presented directly in the schemes.

Using para-amino benzoic acid (1) as the starting material derivative 4 was made in a three-step reaction sequence (Scheme 1).[9-11] Para-amino benzoic acid (1 or PABA) was first reacted with maleic anhydride (MA) in dry acetone to give the diacid (2) with 90% yield. Cyclisation to form the maleimide was accomplished with acetic anhydride and sodium acetate to give compound 3 with 89% yield after hydrolysis of the mixed anhydride intermediate with water. Finally, activation of acid 3 with iso-butyl chloroformate in the presence of pyridine was done followed by treatment with tert-butyl carbazate gave the desired anti-inflammatory derivative 4 with 54% yield. Deprotection of 4 with hydrochloric acid in ether gave the hydrochloride salt 5 with 46% yield after recrystallization. Example 1 shows the preparation of compounds 4 and 5. This reaction sequence can be used to produce other derivatives starting from unsubstituted or substituted ortho-, meta- and para-benzoic acid starting materials. Hence, this approach lead to the synthesis of N'-[3-(2,5-dioxo-2,5-dihydro-pyrrol-1-yl)-4-chloro-benzoyl]-hydrazine carboxylic acid tert-butyl ester (4a) and N'-[4-(2,5-dioxo-2,5-dihydro-pyrrol-1-yl)-2-chloro-benzoyl]-hydrazine carboxylic acid tert-butyl ester (4b) shown in examples 2 and 3, respectively.

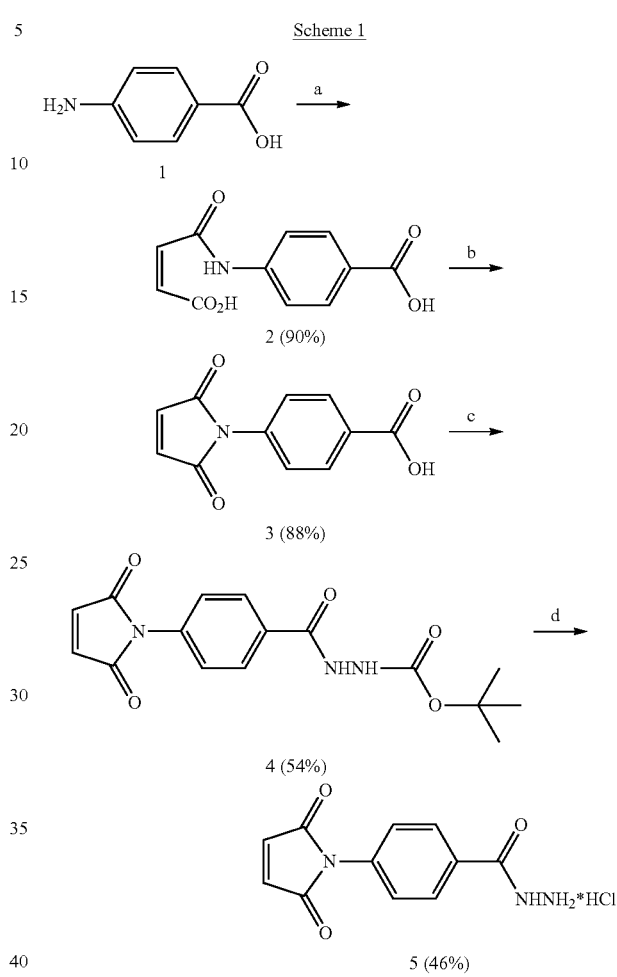

Reagents and conditions: a) Maleic anhydride (MA), dry acetone, methanol, 22° C., 1 h; b) 1) Ac₂O, AcONa, 50° C., 2 h; 2) H₂O, 70° C., 2 h; c) 1) iso-butyl chloroformate, Et₃N, CH₂Cl₂, 0° C., 1 h and 22° C., 1 h; 2) tert-butyl carbazate, CH₂Cl₂, 22° C., 12 h; d) HCl, dioxane, 22° C., 5 h.

Further transformations of derivative 4 can lead to novel compounds with anti-inflammatory, anti-metastatic, antiproliferative and anticancer activities (Scheme 2). However, catalytic hydrogenation of 4 led to compound 12 which lost its anti-inflammatory activity (see example 4). Otherwise, compound 4 is transformed into its trifluoroacetate salt 6 upon treatment with trifluoroacetic acid in dichloromethane. The crude material 6 can be reacted either with acetyl chloride or acetic anhydride (or any relevant anhydride or acid chloride) to give derivative 8. Of note, derivatives 7 and 9 were likely produced but not isolated in example 5. Alternatively, compound 4 can be acylated with a relevant anhydride or acid chloride to yield compound 10 and 11. Interestingly, using acetyl chloride, compound 4 was transformed efficiently into the diacetylated derivative 11 (R═CH₃) and, with acetic anhydride the main product of the reaction was the monoacetylated derivative 10 (R═CH₃). Derivative 10 can be deprotected to give 7 and derivative 11 can lead to derivative 9. It is possible to produce efficienly compound 7 and 9 via a two-step sequence from 4.

Scheme 2

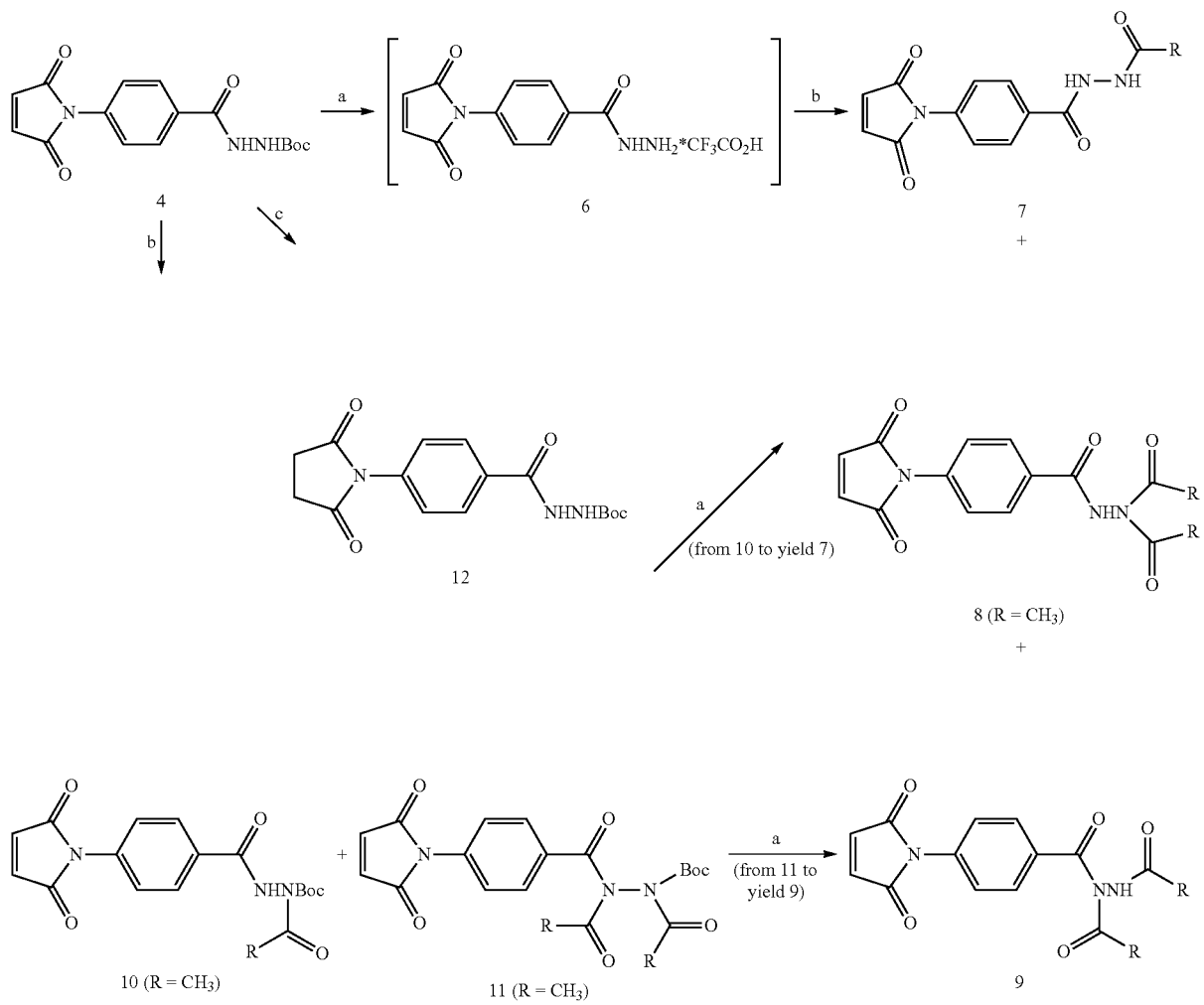

Reagents and conditions: a) TFA, CH$_2$Cl$_2$, 22° C., 0.5 h; b) Relevant anhydride or acid chloride, EtOAc, 22° C., 30 min to 2 h; c) H$_2$, Pd/C, CH$_3$OH, 22° C., 3 h.

Scheme 3 presents the methodology leading to 13 the alkylhydrazones or arylhydrazones derivatives following the procedure described by Taha et al.[12] Accordingly, compound 5 can be treated with a relevant aldehyde (alkyl aldehydes (linear or branched), benzaldehyde or substituted benzaldehydes or other arylaldehydes) under acidic conditions at reflux in butanol (or other solvent) to give the desired derivatives of general structure 13.

Scheme 3

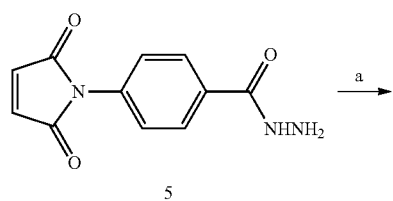

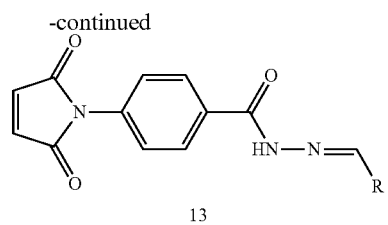

R = alkyl or aromatic (unsubstituted or substituted)
Reagents and conditions: a) RCHO, H$^+$, Butanol, reflux, 1 to 5 h.

On Scheme 4, derivative 4 (or any other maleimides described herein) can be reacted with an appropriate diene (butadiene (unsubstituted or substituted), cyclopentadiene, cyclohexadiene cycloheptadiene, furane, thiophene, pyrrole, N-alkylpyrrole) to give the desired cycloadducts (Diels-Alder products) such as 14, 15 and 16. This reaction can be performed by heating the pure reagents (diene and dienophile) either neat or in solution, with or without pressure as it is described in example 10.

Scheme 4

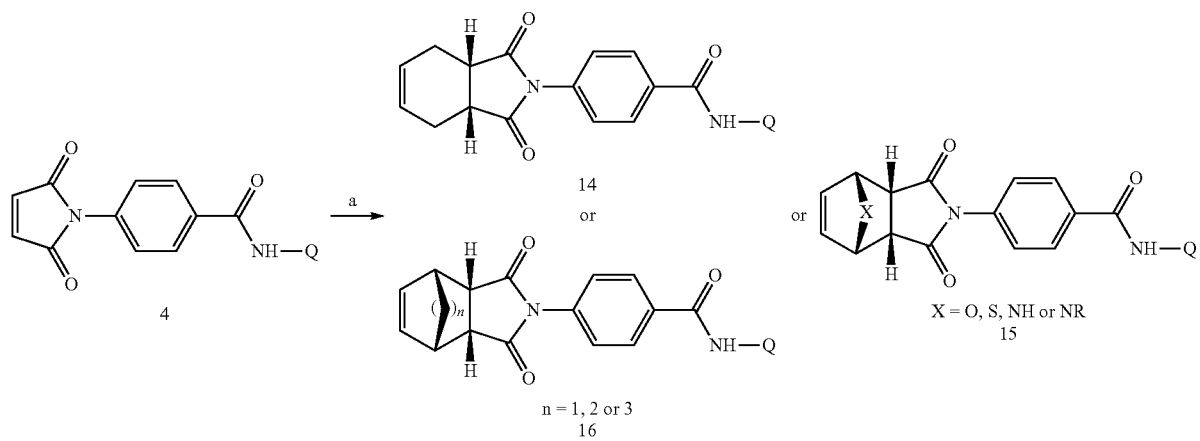

Relevant diene = butadiene (unsubstituted or substituted), cyclopentadiene, cyclohexadiene, furane, thiophene, pyrrole, N-alkyl pyrrole.
Reagents and conditions: a) Relevant diene, toluene, Δ, 3 h.

As it can be appreciated by the skilled artisan, the above synthetic schemes are not intended to be a comprehensive list of all means by which the compounds described and claimed in this application may be synthesized. Further methods can also potentially be used to prepare the compounds of the present disclosure.

The compounds of the present disclosure may be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the present disclosure may contain one or more asymmetric carbon atoms and thus may occur as racemates and racemic mixtures, single enantiomer, diastereomeric mixtures and individual diastereoisomers. All such isomeric forms of these compounds are expressly included in the present disclosure. Each stereogenic carbon may be of the R or S configuration.

It has been found that the small aminobenzoic acid derivatives herein disclosed display anti-inflammatory, anti-metastatic, anti-proliferative and/or anti-cancer properties as well as favorable toxicity profiles, and may be used for example in treating malignancies, for example muscle-invasive and superficial UBC tumors, for example in humans.

An aspect herein provided is a method for treating cancer or at least one cancer chosen from melanoma, breast cancer, uterine cancer, ovarian cancer, prostate cancer and bladder cancer, the method comprising administering to a subject in need thereof an effective amount of at least one compound as defined herein.

Another aspect is a method for reducing the risks of developing cancer or for reducing the risk of developing at least one cancer in a subject, the cancer being, for example, chosen from melanoma, breast cancer, uterine cancer, ovarian cancer, prostate cancer and bladder cancer, the method comprising administering to the subject an effective amount of at least one compound as defined herein.

Yet a further aspect is a method for inhibiting cancer cell growth, the method comprising administering to a subject in need thereof an effective amount of at least one compound as defined herein.

For example, the cancer cell growth is inhibited by at least about 10%, about 20%, about 30%, about 40%, about 50%, about 60%, about 70% or about 80% relative to an untreated subject.

Another aspect is a method for inhibiting tumor growth and/or reducing tumor size, the method comprising administering to a subject in need thereof an effective amount of at least one compound as defined herein.

For example the tumor size is measured in weight and/or volume.

For example, the tumor growth and/or tumor size is decreased by at least about 10%, about 20%, about 30%, about 40%, about 50%, about 60%, about 70%, about 80% or about 90% relative to an untreated subject.

For example, administration of an effective amount of at least one compound disclosed herein to a subject in need thereof increases time to progression of at least one cancer chosen from melanoma, breast cancer, uterine cancer, ovarian cancer, prostate cancer and bladder cancer.

For example, the compound herein disclosed is for use in reducing risks of developing at least one cancer chosen from melanoma, breast cancer, uterine cancer, ovarian cancer, prostate cancer and bladder cancer.

For example, the compound is for use in the treatment of at least one cancer chosen from melanoma, breast cancer, uterine cancer, ovarian cancer prostate cancer and bladder cancer.

For example, the compound is for use as an anticancer agent.

For example the compound is for use as an anti-inflammatory agent.

For example the compound is for use as an anti-metastatic agent.

As described herein, several compounds, namely derivatives 4, 5, 8, 10, 11, and 12, were tested on macrophages and UBC cells for their anti-inflammatory, anti-metastatic and/or anti-cancer properties.

As shown herein, the compounds presently disclosed display anti-inflammatory properties.

Figure 2:
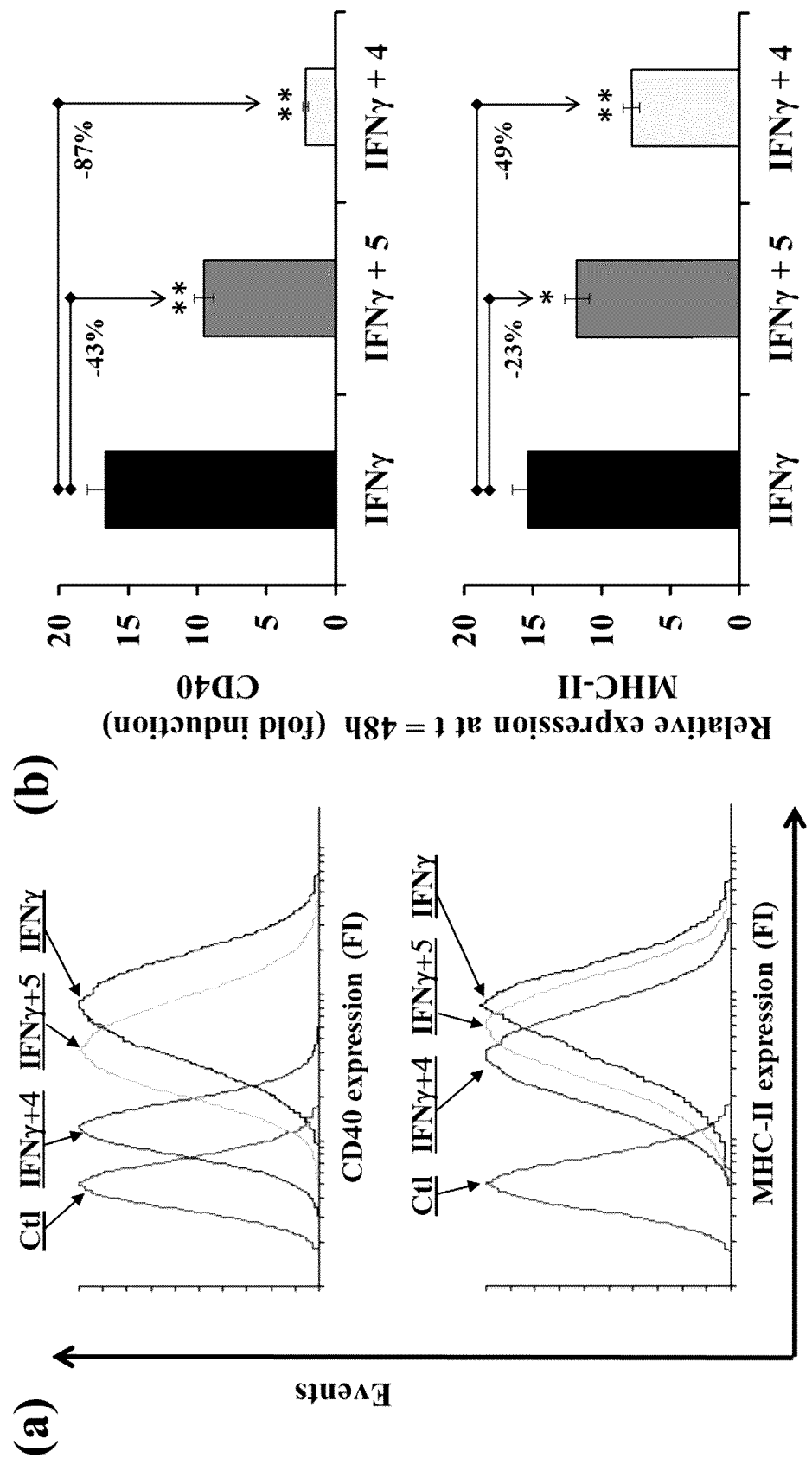
FIG. 2 represents images (a) and graphical analysis (b) showing flow cytometry analysis to determine the expression level of MHC-II and CD40 surface antigens in resting and IFNγ-activated human macrophages untreated and pretreated with compounds 4 (10 µM) and 5 (25 µM). Compounds 4 and 5 efficiently inhibited IFNγ-induced CD40 and MHC-II expression. *$p<0.05$ and **$p<0.01$ denote significant differences between treatments.
Figure 3:
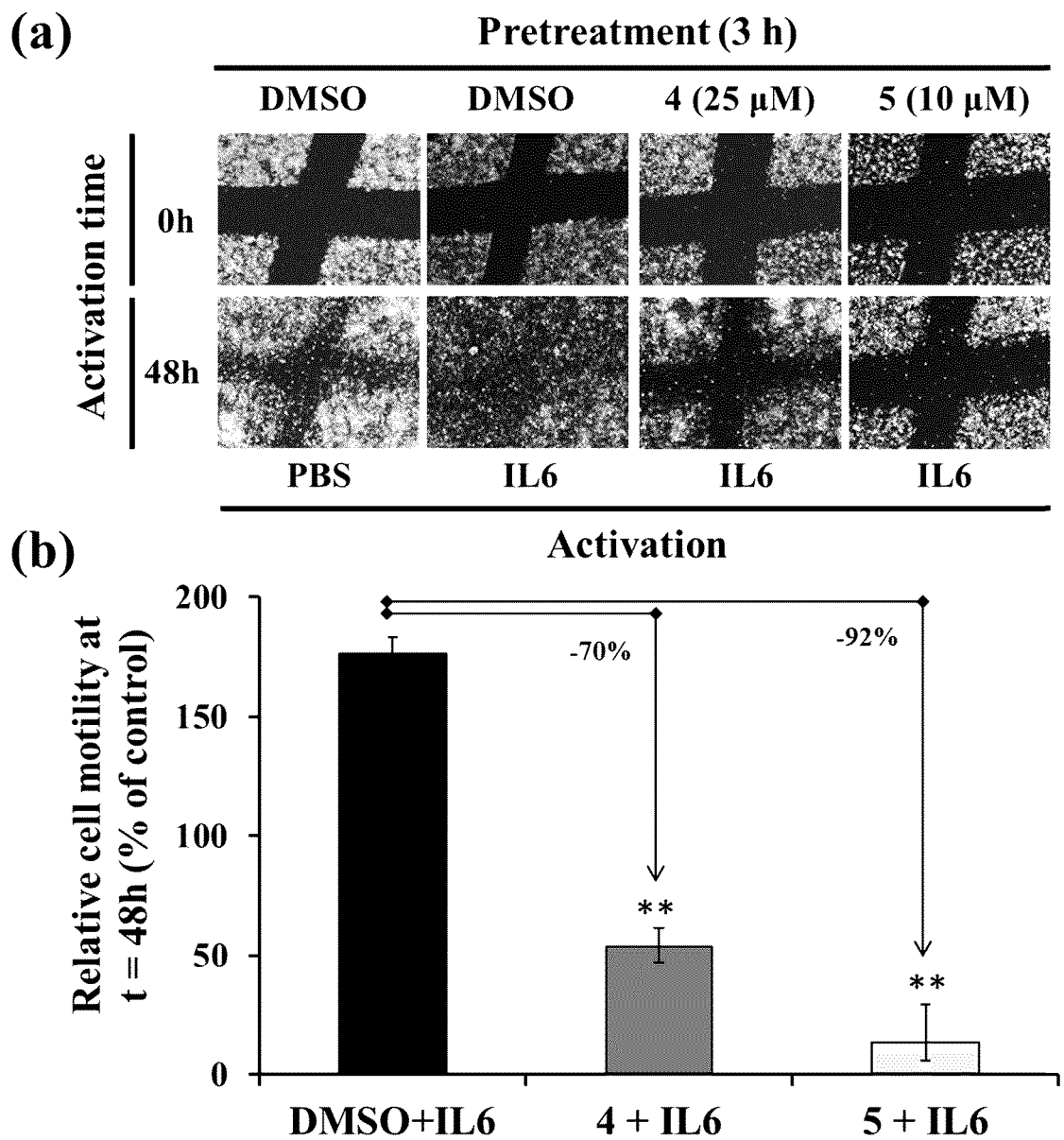
FIG. 3 represents images (a) and graphical analysis (b) showing scratch wound healing assays to determine the motility of human macrophages monolayers cultured for 3 h with vehicle (DMSO) or compounds 4 (10 µM) and 5 (25 µM), and then activated for 48 h with vehicle (PBS) or 25 ng/mL IL6. The images of the scratch were acquired at t=0 h and t=48 h by fluorescence microscopy. Five fields were taken randomly for each different treatment. All observations were performed at 5× magnification. Cell motility was expressed as percent (%) of control of motile cells at t=48 h relative to motile cells at t=0 h. Compounds 4 and 5 efficiently inhibited IFNγ-induced STAT1 activation and IL6-induced STAT3 activation. *$p<0.05$ and **$p<0.01$ denote significant differences between treatments.

Referring to FIGS. 1 to 10, in vitro studies of human macrophages and UBC cells tested with compounds 4 and 5 were conducted to investigate the anti-inflammatory properties of the compounds on pro-inflammatory cytokines. As shown in FIG. 1, IFNγ-induced STAT1 activation and IL6-induced STAT3 activation were decreased in pretreated human macrophages. Similarly, compounds 4 and 5 were found effective in reducing IFNγ-induced CD40 and MHC-II expressions, as shown in FIG. 2. Also, referring to FIG. 3, scratch wound healing assays were conducted and compounds 4 and 5 were found effective in inhibiting IFNγ-induced STAT1 activation and IL6-induced STAT3 activation in human macrophages.

An aspect provided is a method for decreasing anti-inflammatory properties of cancer cells, the method comprising contacting the cancer cells with at least one compound as defined herein.

For example the relative STAT1 activation of cells treated with a compound herein disclosed is decreased by at least about 10%, about 20%, about 30%, about 40%, about 50%, about 60%, about 70% or about 80% relative to untreated cells.

For example the relative STAT3 activation of cells treated with a compound herein disclosed is decreased by at least about 10%, about 20%, about 30%, about 40%, about 50%, about 60%, about 70% or about 80% relative to untreated cells.

For example the CD40 expression of cells treated with a compound herein disclosed is decreased by at least about 10%, about 20%, about 30%, about 40%, about 50%, about 60%, about 70% or about 80% relative to untreated cells.

For example the MHC-II expression of cells treated with a compound herein disclosed is decreased by at least about 10%, about 20%, about 30%, about 40%, about 50%, about 60%, about 70% or about 80% relative to untreated cells.

Figure 4:
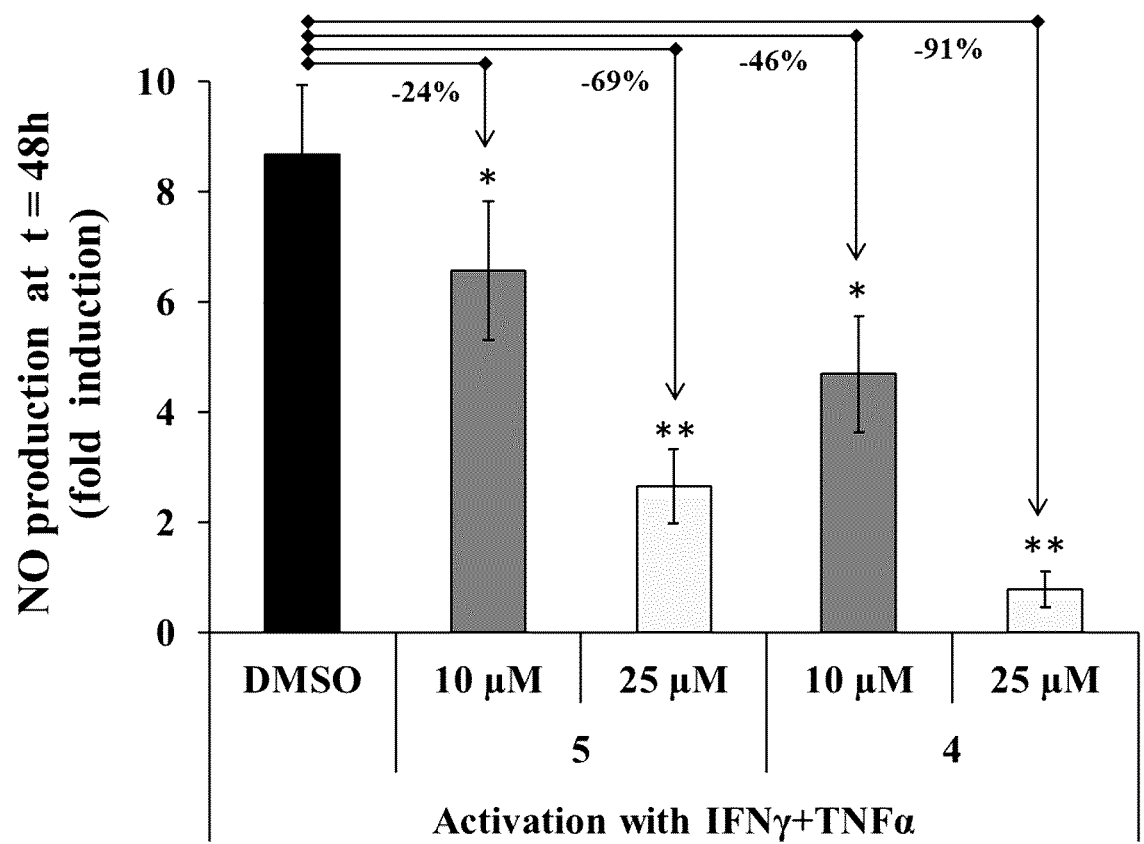
FIG. 4 is a graphical representation of NO production in the macrophage-like J774A.1 cells following a pro-inflammatory stimulation by IFNγ and TNFα after pretreatment with vehicle (DMSO) and the derivatives 4 and 5. Compounds 4 and 5 efficiently inhibited combined IFNγ/TNFα-induced NO synthesis. *$p<0.05$ and **$p<0.01$ denote significant differences between treatments.
Figure 5:
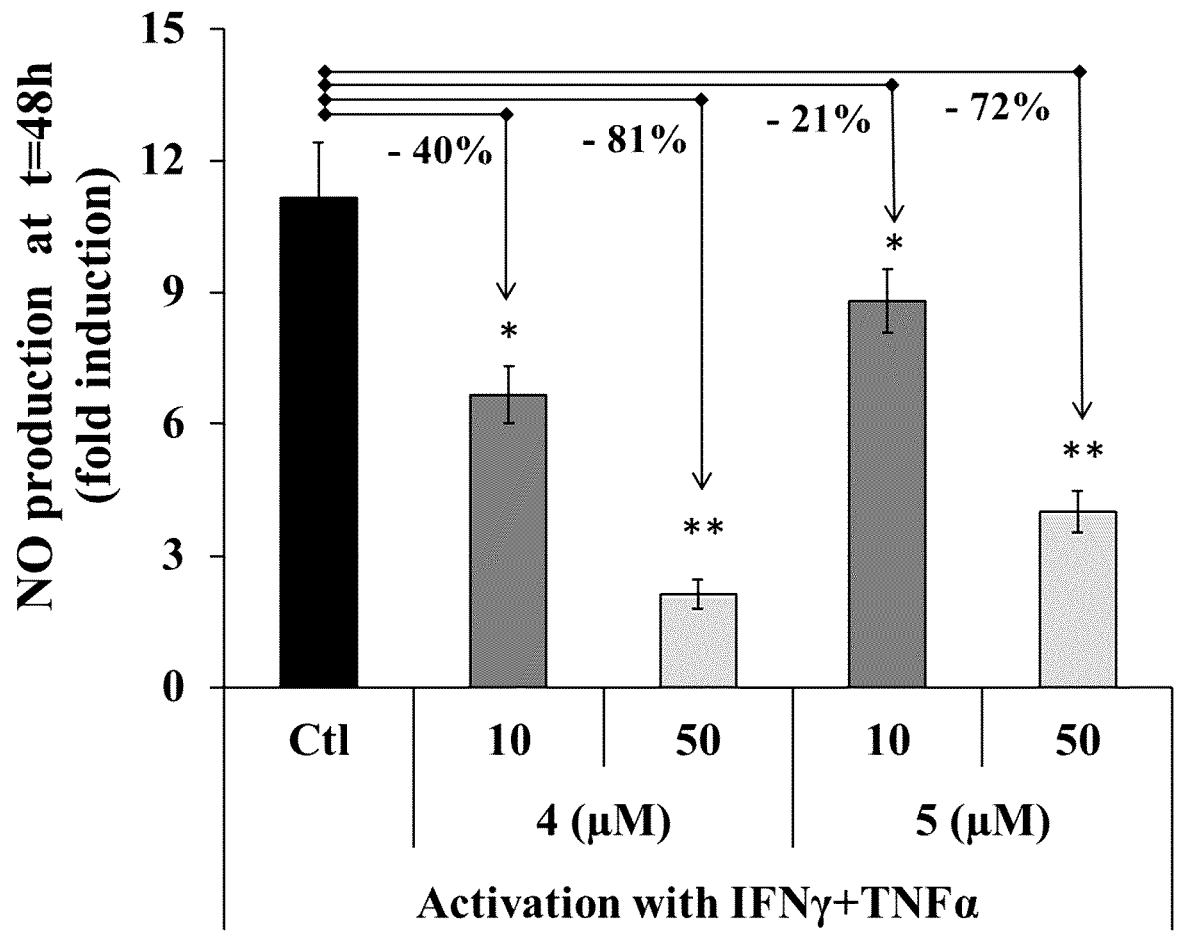
FIG. 5 is a graphical representation of NO production by the murine UBC cell line MB49-I following a pro-inflammatory stimulation by IFNγ and TNFα after pretreatment with vehicle (DMSO) and derivatives 4 and 5. Compounds 4 and 5 at 10 and 50 µM efficiently inhibited combined IFNγ/TNFα-induced NO synthesis. *$p<0.05$ and **$p<0.01$ denote significant differences between treatments.

Referring now to FIGS. 4 and 5, anti-inflammatory activity of compounds 4 and 5 was assessed by measuring nitric oxide (NO) production in murine macrophage-like cells stimulated with inflammatory signals, IFNγ/TNFα. Compounds 4 and 5 were found effective in reducing IFNγ/TNFα induced NO production.

For example, NO production in cells treated with a compound herein disclosed is decreased by at least about 10%, about 20%, about 30%, about 40%, about 50%, about 60%, about 70% or about 80% relative to untreated cells.

Figure 6:
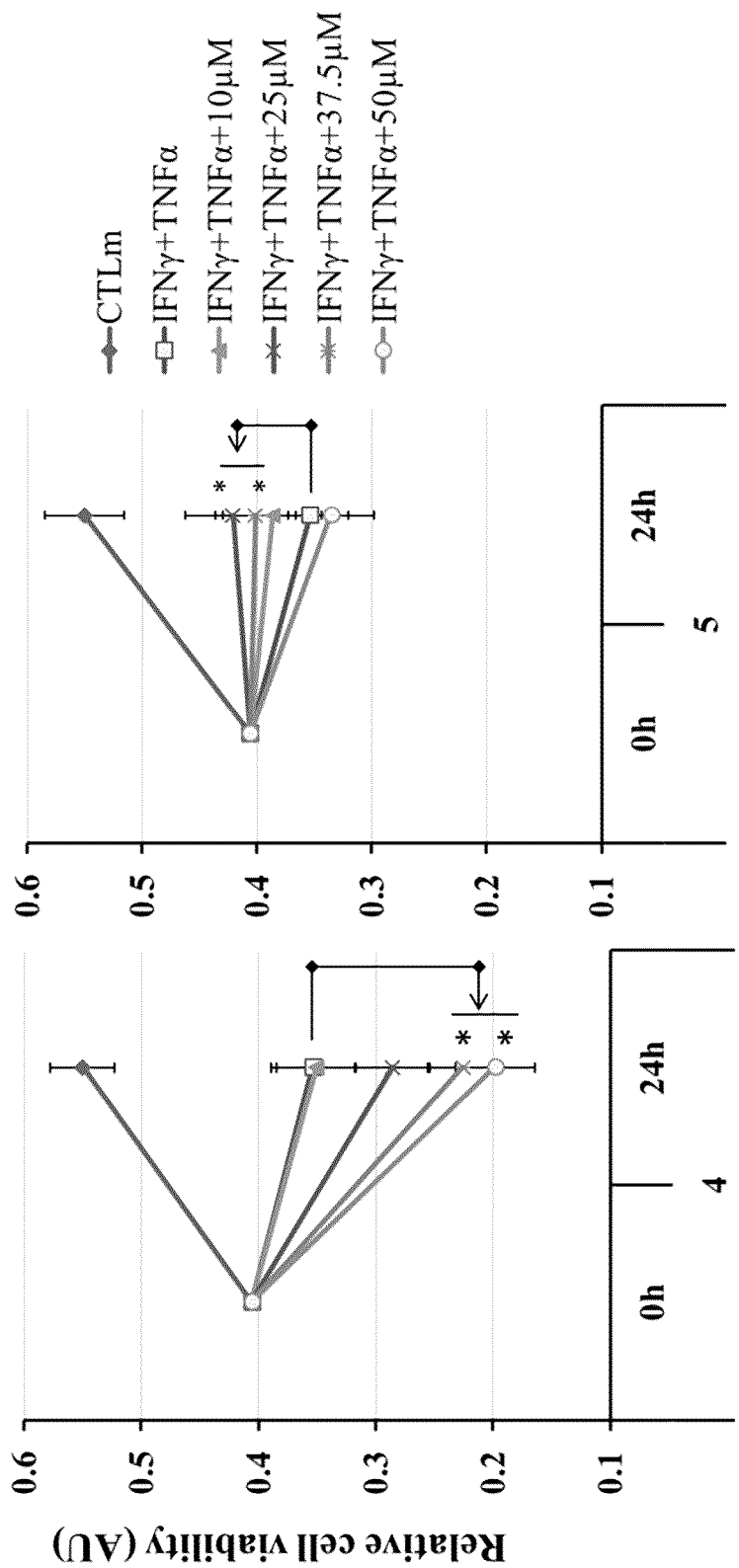
FIG. 6 is a graphical representation of relative cell viability on the murine UBC cell line MB49-I following a pro-inflammatory stimulation by IFNγ and TNFα after pretreatment with vehicle (DMSO) and anti-inflammatory derivatives 4 and 5 at different concentrations. Compounds 4 and 5 at low doses (10, 25 and 37.5 µM) had little or no effect on the anti-proliferative activity of combined IFNγ and TNFα in MB49-I cells. *$p<0.05$ denote significant differences between treatments with combined IFNγ and TNFα plus compounds 4 or 5 versus combined IFNγ and TNFα alone.
Figure 7:
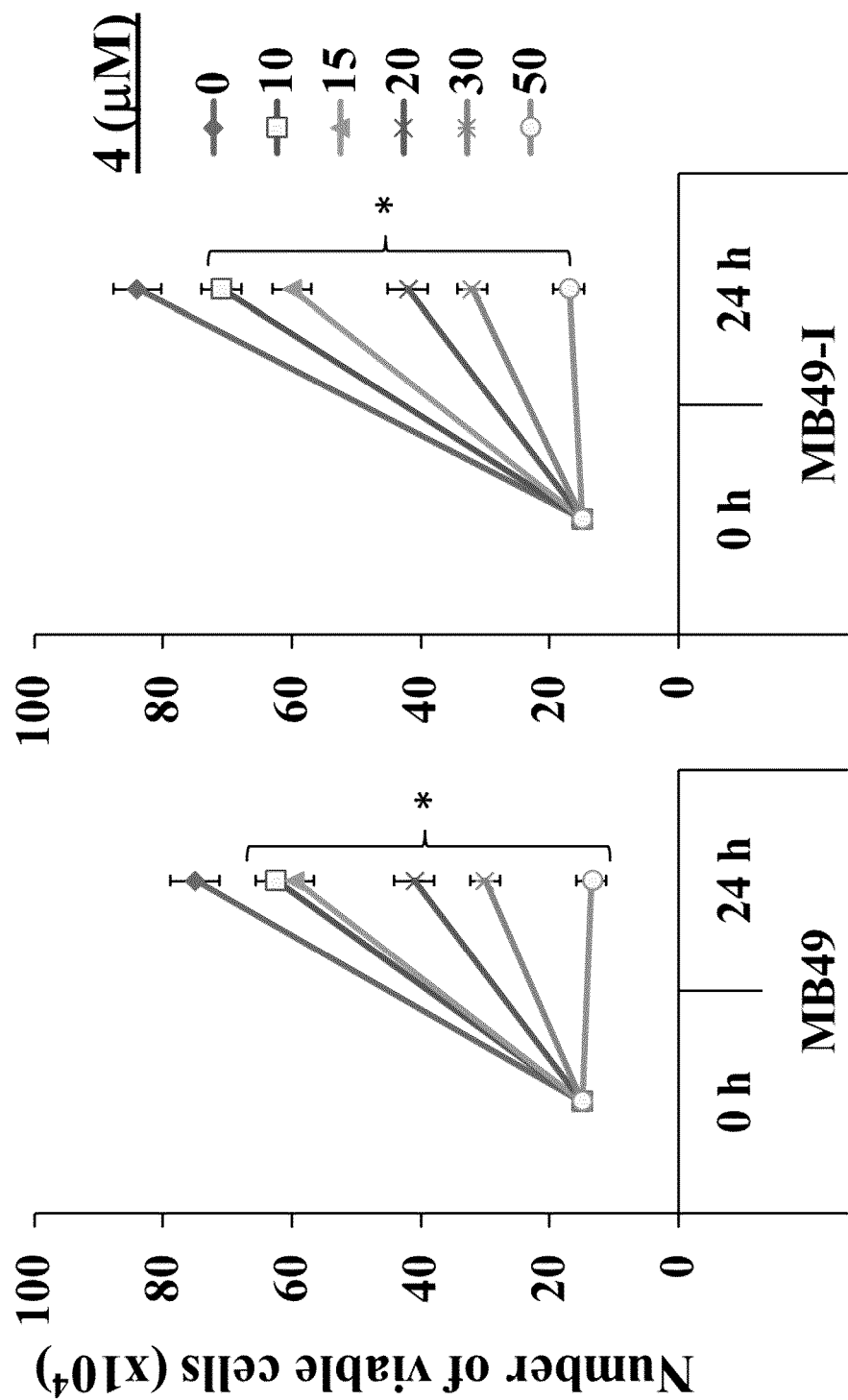
FIG. 7 refers to relative cell viability on MB49 and MB49-I cell lines 24-hour post treatment (3 h) with either vehicle (DMSO) or compound 4 at different concentrations (0, 10, 15, 20, 30, and 50 µM). The negative effects of compound 4 on cell survival would not be caused by an increase in cell mortality of UBC MB49 or MB49-I cells but rather by stopping cell proliferation. *$p<0.05$ denote significant difference compared to control (without compound 4)

Referring to FIGS. 6 and 7 it was demonstrated that compounds 4 and 5 have anti-proliferative properties in UBC cells stimulated with IFNγ/TNFα.

An aspect provided is a method for inducing anti-proliferative properties of cancer cells, the method comprising contacting the cancer cells with at least one compound as defined herein.

For example, the viability of cells treated with a compound herein disclosed is decreased by at least about 10%, about 20%, about 30%, about 40%, about 50%, about 60%, about 70% or about 80% relative to untreated cells.

For example, the cancer cell growth is inhibited by at least about 10%, about 20%, about 30%, about 40%, about 50%, about 60%, about 70% or about 80% relative to untreated cancer cells.

Figure 8:
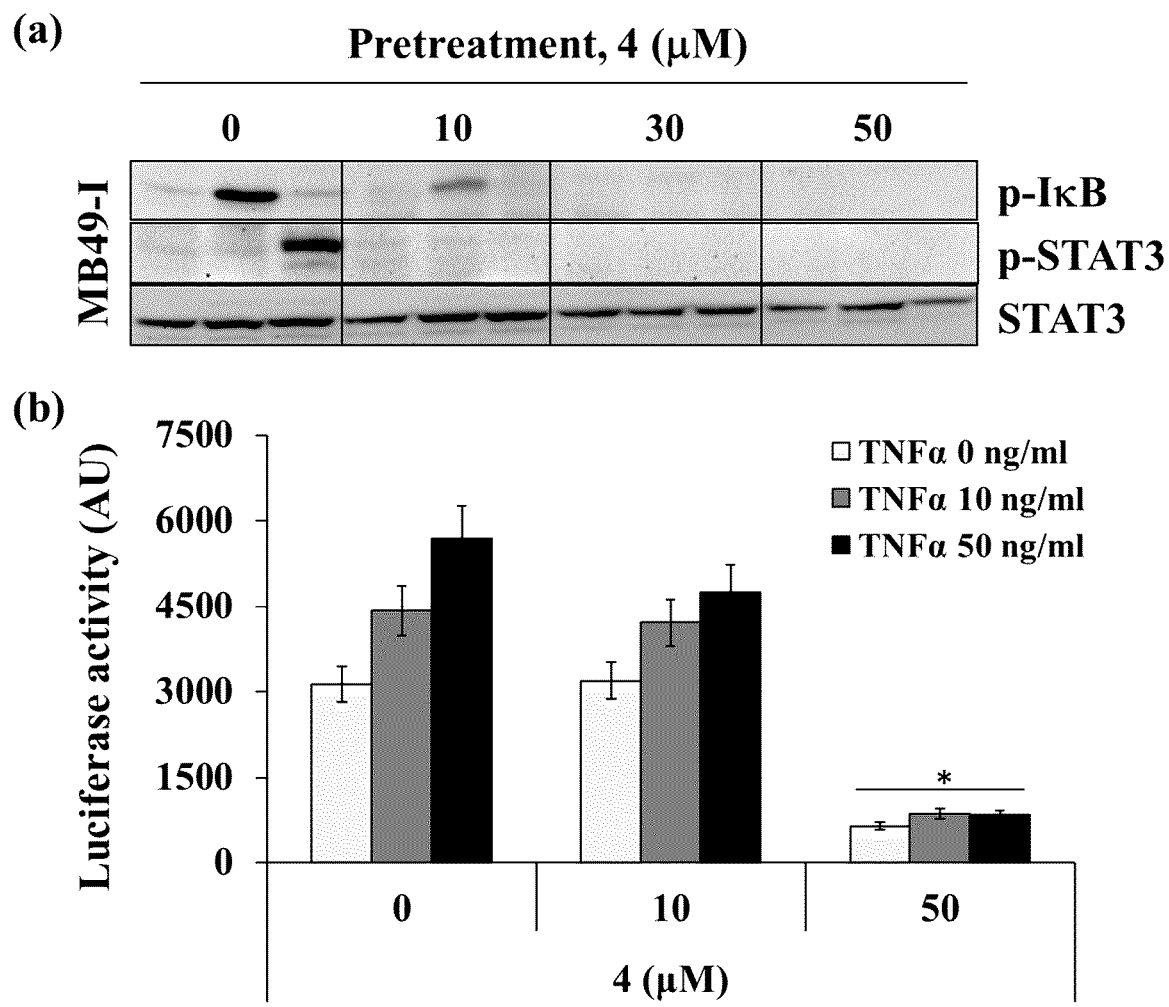
FIG. 8 refers to (a) Western blot analysis: compound 4 efficiently inhibited TNFα/NFκB and IL6/STAT3 signaling pathways in murine UBC MB49-I cells at doses as lower as 10 µM; and (b) Luciferase assay: compound 4 at 50 µM efficiently inhibited NFκB activation. MB49-I cells were transfected with an NFκB-responsive luciferase construct encoding the firefly luciferase reporter gene under the control of CMV promoter and tandem repeats of the NFκB transcriptional response element. *$p<0.01$ denote significant difference compared to control.
Figure 9:
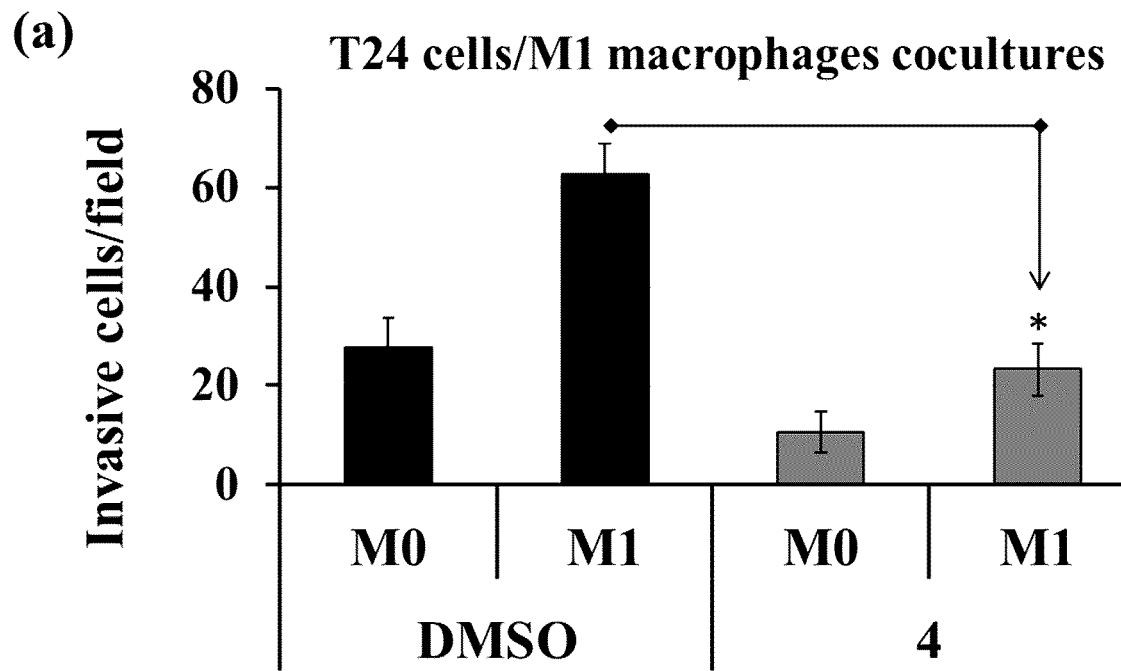
FIG. 9 refers to (a) microinvasion assays: compound 4 efficiently inhibited M1-induced human UBC T24 cell invasion (matrigel in Boyden chamber); and (b) motility assays: compound 4 at 30 µM efficiently inhibited IL6-induced motility (scratch assay) in human UBC T24 cells. *$p<0.05$ denote significant difference compared to control (M1 DMSO)
Figure 9:
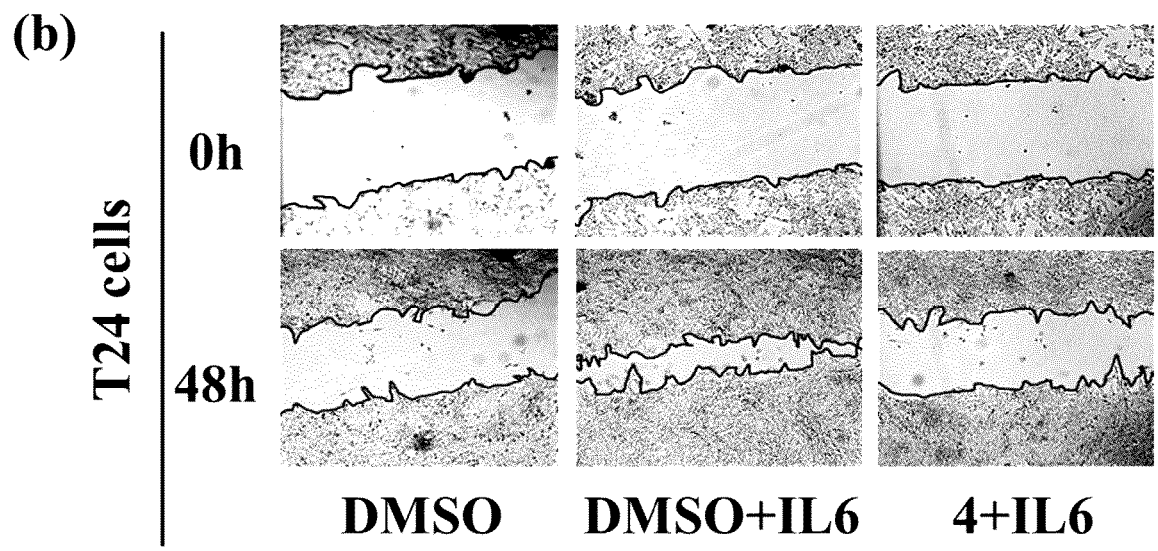
Figure 10:
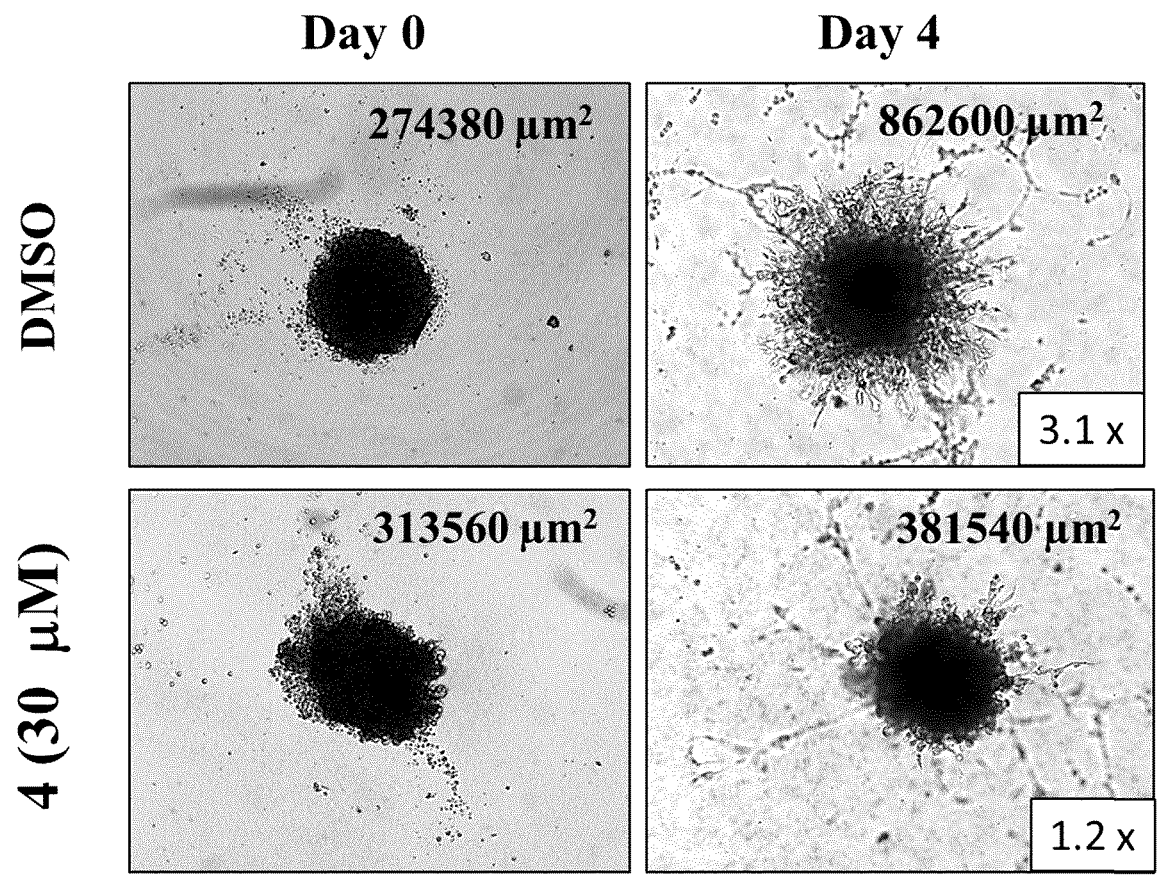
FIG. 10 refers to cellular analysis of 3D spheroid-based tumor invasion assays: compound 4 at 30 µM efficiently inhibited the invasiveness activity of MDA-MB-241 cells, a highly invasive human breast cancer cell line, thus demonstrating that the anti-invasion effects of compound 4 is not cell-specific. *$p<0.01$ denote significant difference compared to day 0.

Referring now to FIG. 8, compound 4 was shown to inhibit TNFα/NFκB and IL6/STAT3 signaling pathways in murine UBC cells. Compound 4 was also tested in human UBC cells and was shown to inhibit IL6-induced motility, as shown in FIG. 9. Similarly, referring to FIG. 10, a human breast cancer cell line was treated with compound 4 which demonstrated anti-invasion properties, thus demonstrating that compound 4 is not cell-specific.

For example, the TNFα/NFκB and/or IL6/STAT3 signaling pathways of cells treated with a compound herein disclosed is decreased by at least about 10%, about 20%, about 30%, about 40%, about 50%, about 60%, about 70% or about 80% relative to untreated cells.

For example, the invasiveness of cells with a compound herein disclosed is decreased by at least about 10%, about 20%, about 30%, about 40%, about 50%, about 60%, about 70% or about 80% relative to untreated cells.

In vivo studies were also conducted to evaluate the anticancer, anti-proliferative and anti-metastatic activities of compound 4 in ectopic and orthotopic murine models of UBC.

Figure 11:
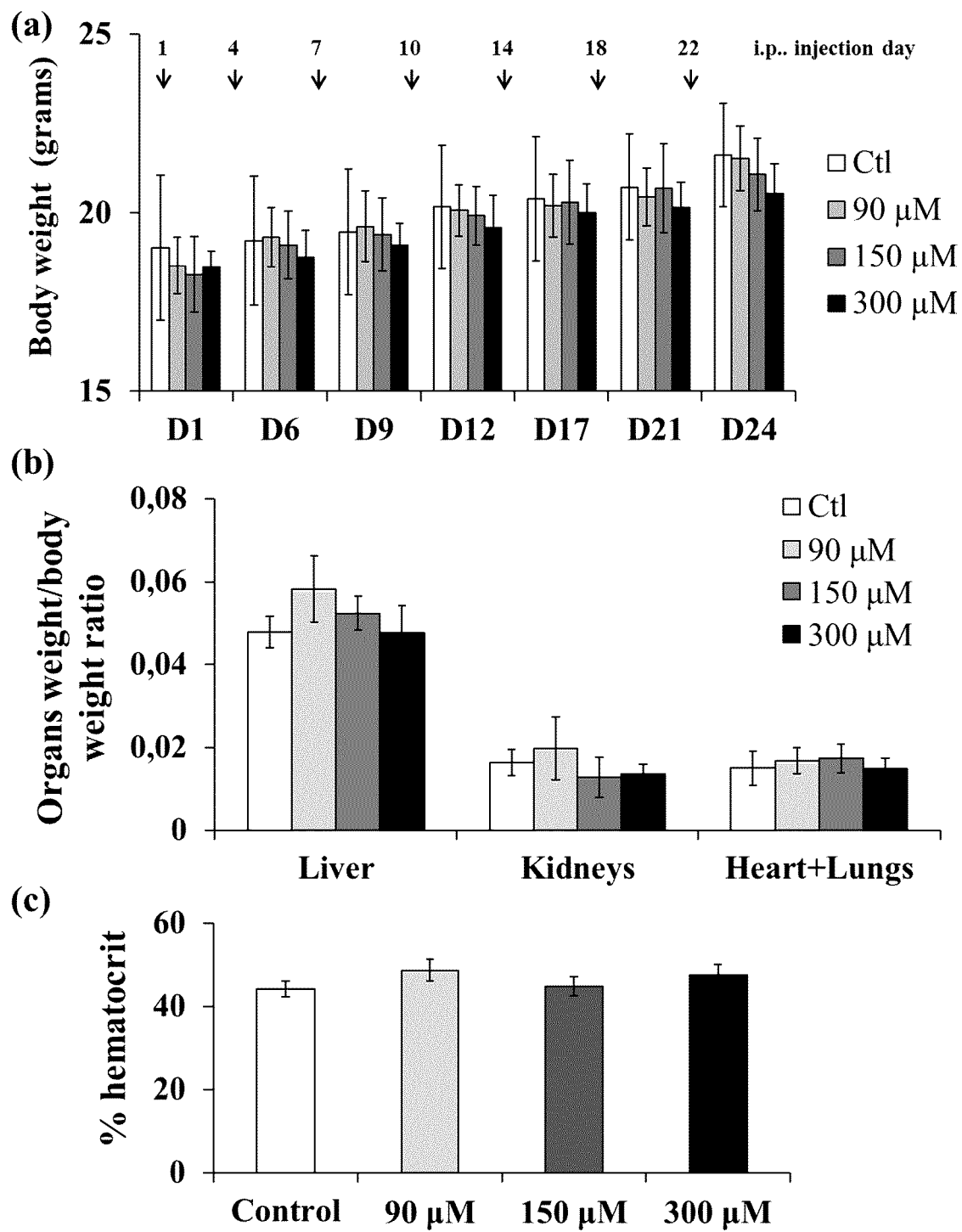
FIG. 11 refers to acute toxicity studies with episodic intraperitoneal (i.p.) injections of compound 4 at different concentrations (0, 90, 150, and 300 µM) in C57Bl/6J mice (n=4) during 3 weeks. Treatments have no obvious effect on normal development and viability (a), as well as in organs weight (b) and hematocrit (c)
Figure 12:
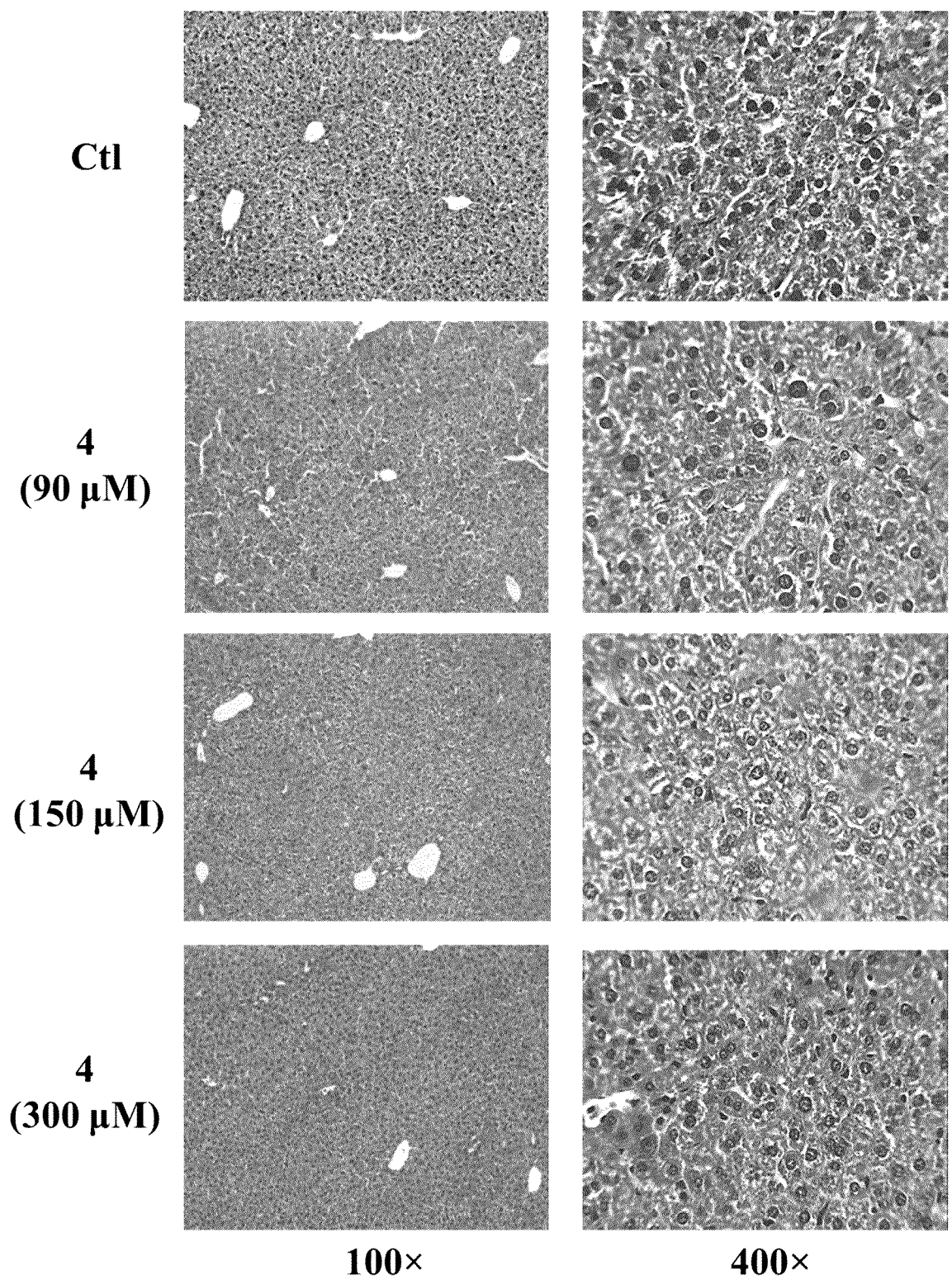
FIG. 12 represents images showing liver histological analysis in C57Bl/6J mice at the end of treatment by periodic i.p. injections of compound 4 at different concentrations (0, 90, 150, and 300 μM) during 3 weeks. Treatment, even at higher dose, does not induce features of liver dysfunction such as hepatocellular injury, inflammation, fibrosis and steatosis (haematoxylin and eosin, 100× and 400× magnification). These results showed no evidence of toxicity from the anti-inflammatory treatment, indicating that compound 4 concentrations up to 300 μM were well tolerated in these mice.

Acute toxicity studies in mice, as shown in FIG. 11, demonstrated that treatment with compound 4 had no obvious effect on normal development and viability, as well as in organ weight and hematocrit, suggesting tolerability in the mice. Similarly, referring to FIG. 12, no evidence of toxicity related to compound 4 was found in liver histological analyses in mice treated with various concentrations of compound 4.

For example, subjects treated with a compound disclosed herein have a similar body weight relative to a comparable untreated subject. "Similar body weight" as used herein means no greater than a 10%, 9%, 8%, 7%, 6%, 5%, 4%, 3%, 2% or 1% difference in body weight loss.

For example, subjects treated with a compound disclosed herein have a similar hematocrit relative to a comparable untreated subject. "Similar hematocrit" as used herein means no greater than a 5%, 4%, 3%, 2% or 1% difference in hematocrit level.

As demonstrated herein, the compounds herein disclosed display anti-proliferative and anti-metastatic activity.

Figure 13:
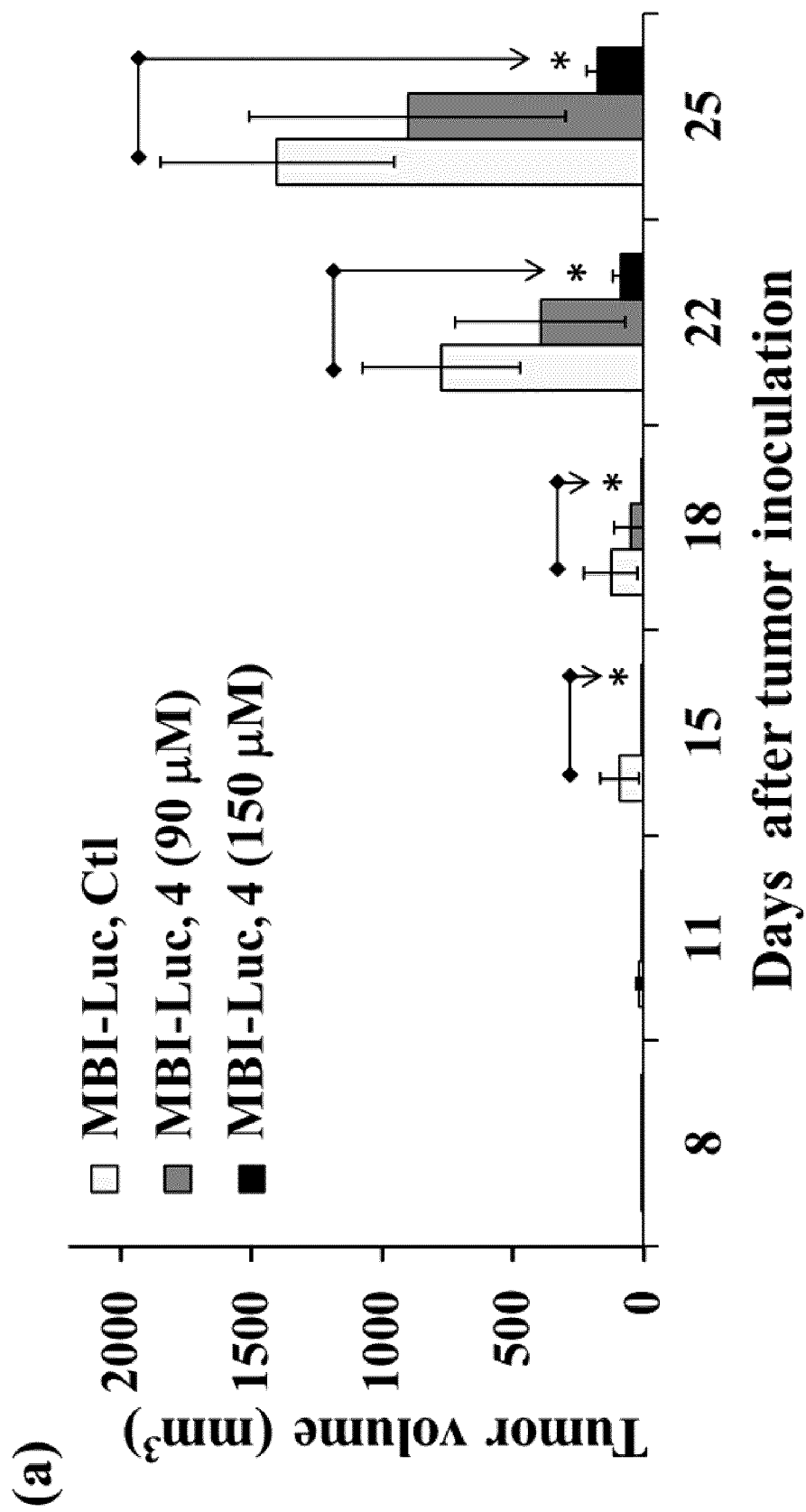
FIG. 13 refers to in vivo targeting study showing the effects of episodic i.p. injections of compound 4 at different concentrations (0, 90, and 150 μM) in C57Bl/6J male mice bearing MB49-I tumors ectopically implanted in the right flank of animals (n=6). Treatment at 150 μM significantly affects tumor development of MB49-I cells subcutaneously implanted in mice. *$p<0.01$ compared to control.
Figure 13:
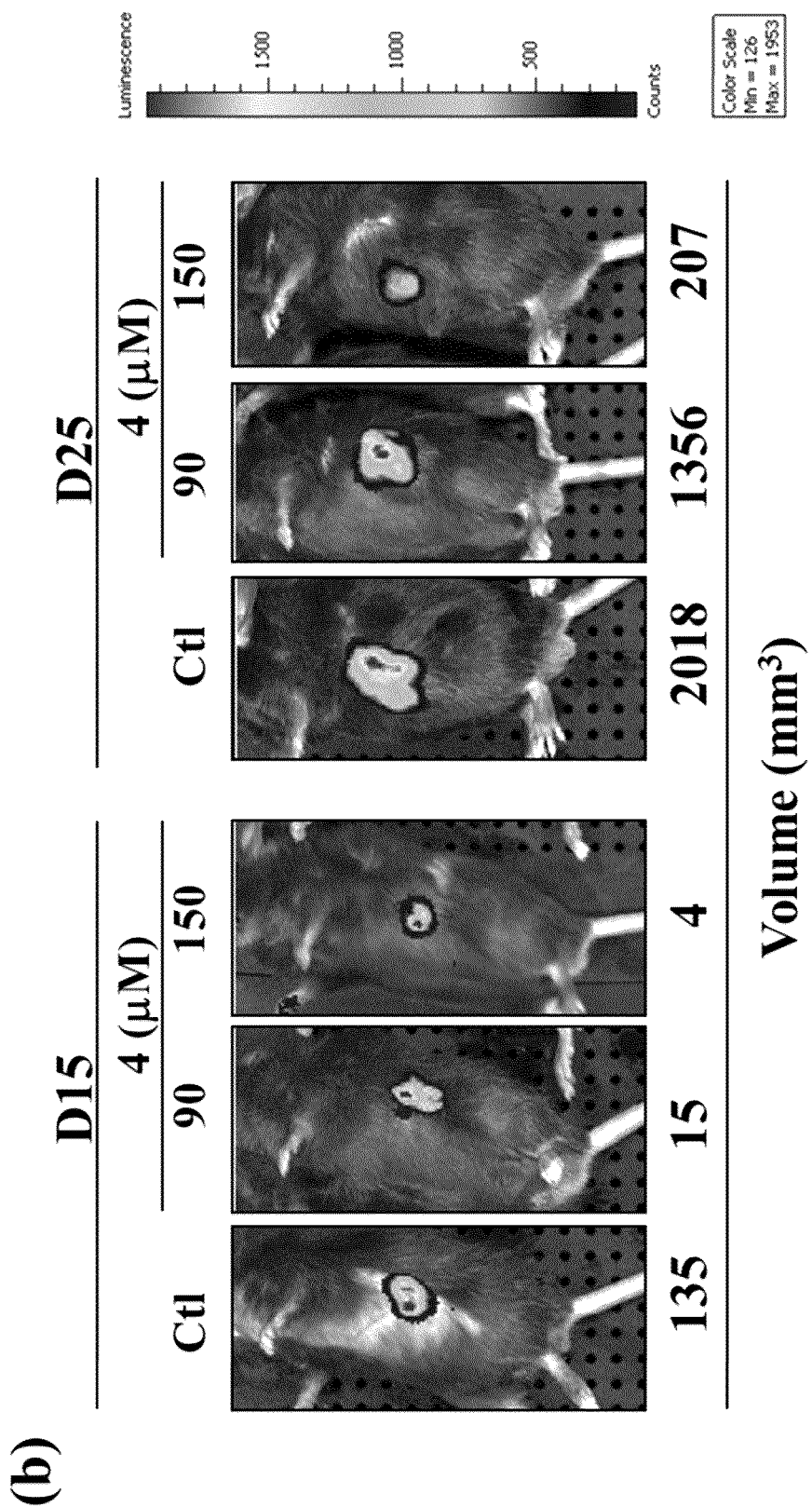
Figure 14:
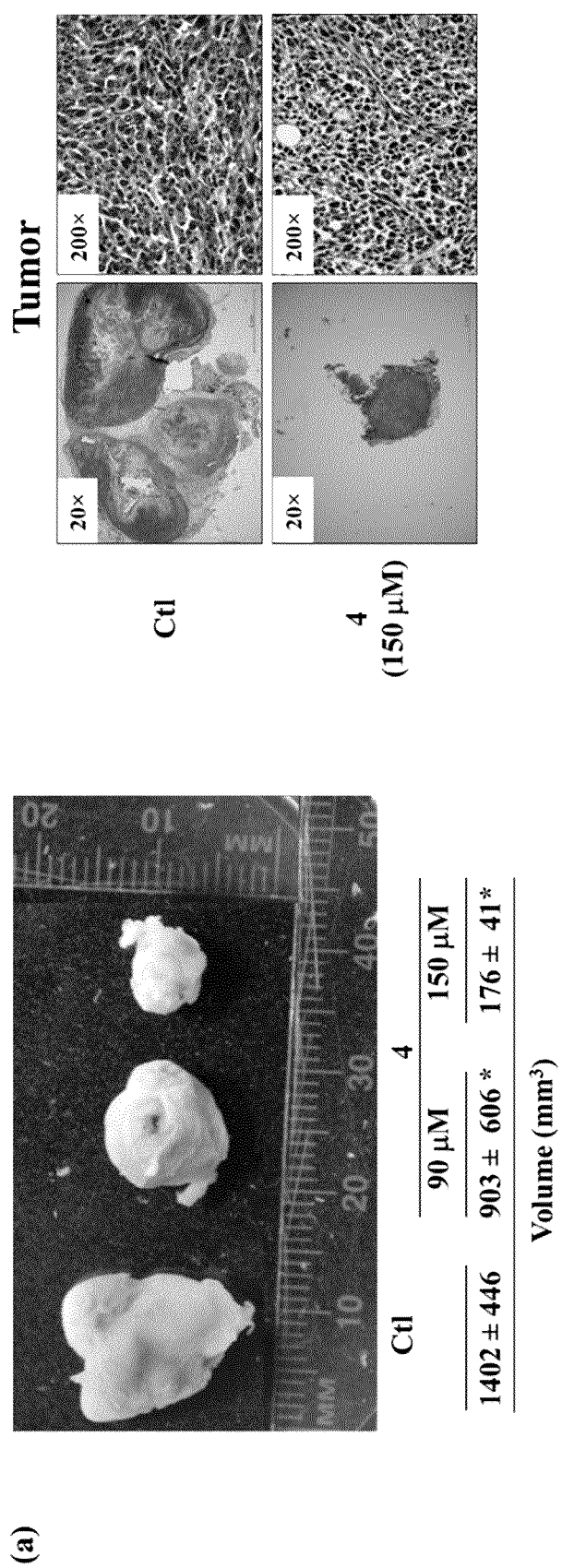
FIG. 14 refers to the anti-metastatic effects of episodic i.p. injections of compound 4 at different concentrations (0, 90, and 150 μM) in C57Bl/6J male mice bearing MB49-I tumors ectopically implanted in animals (n=6). Treatment at 150 μM significantly reduce the size of subcutaneously implanted MB49-I tumors (a) and the number of lung metastases (b). Histological examination of lung specimens demonstrated that MB49-I tumor cell infiltration induced multifocal fibrotic lesions in the lungs of control mice (as indicated by the arrows), whereas no metastatic foci and a well-alveolized normal histology was seen in the lungs of mice treated with 150 μM compound 4. *$p<0.01$ compared to control.
Figure 14:
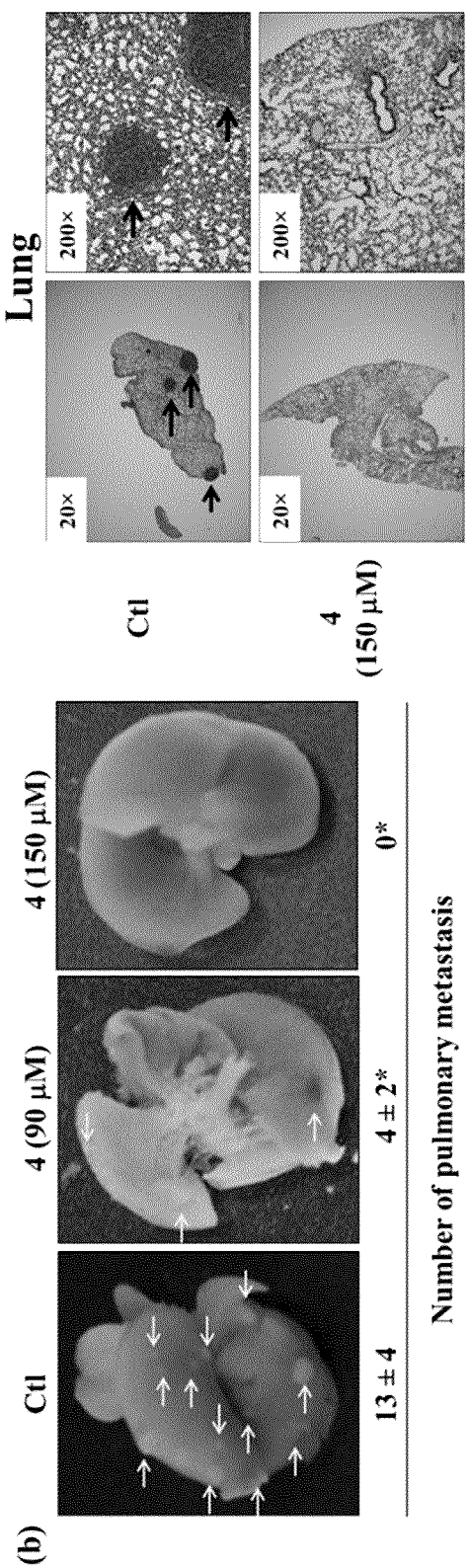
Figure 15:
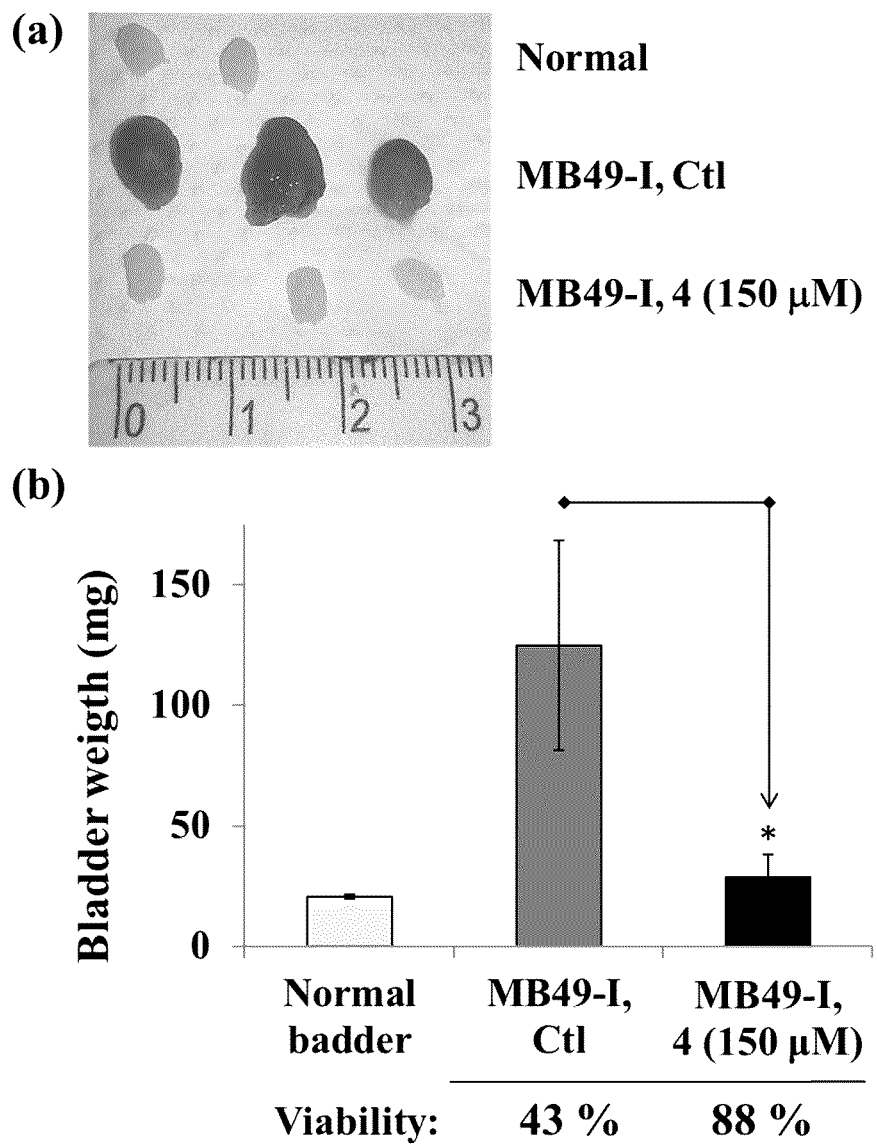
FIG. 15 refers to in vivo targeting study showing the effects of episodic i.p. injections of compound 4 in C57Bl/6J female mice bearing MB49-I tumors orthotopically implanted in the bladder of animals (n=6). (a) Represents images of bladders from normal age-matched mice and bladders that were chirurgically recovered at the end of the study (day 16 after tumor implantation) from control (Ctl) and treated tumor-bearing mice. (b) Graphical representation showing i.p. injections of compound 4 biweekly at 150 μM during two weeks completely abolished the development of muscle-invasive MB49-I tumors (n=6). *$p<0.5$ compared to Ctl.
Figure 16:
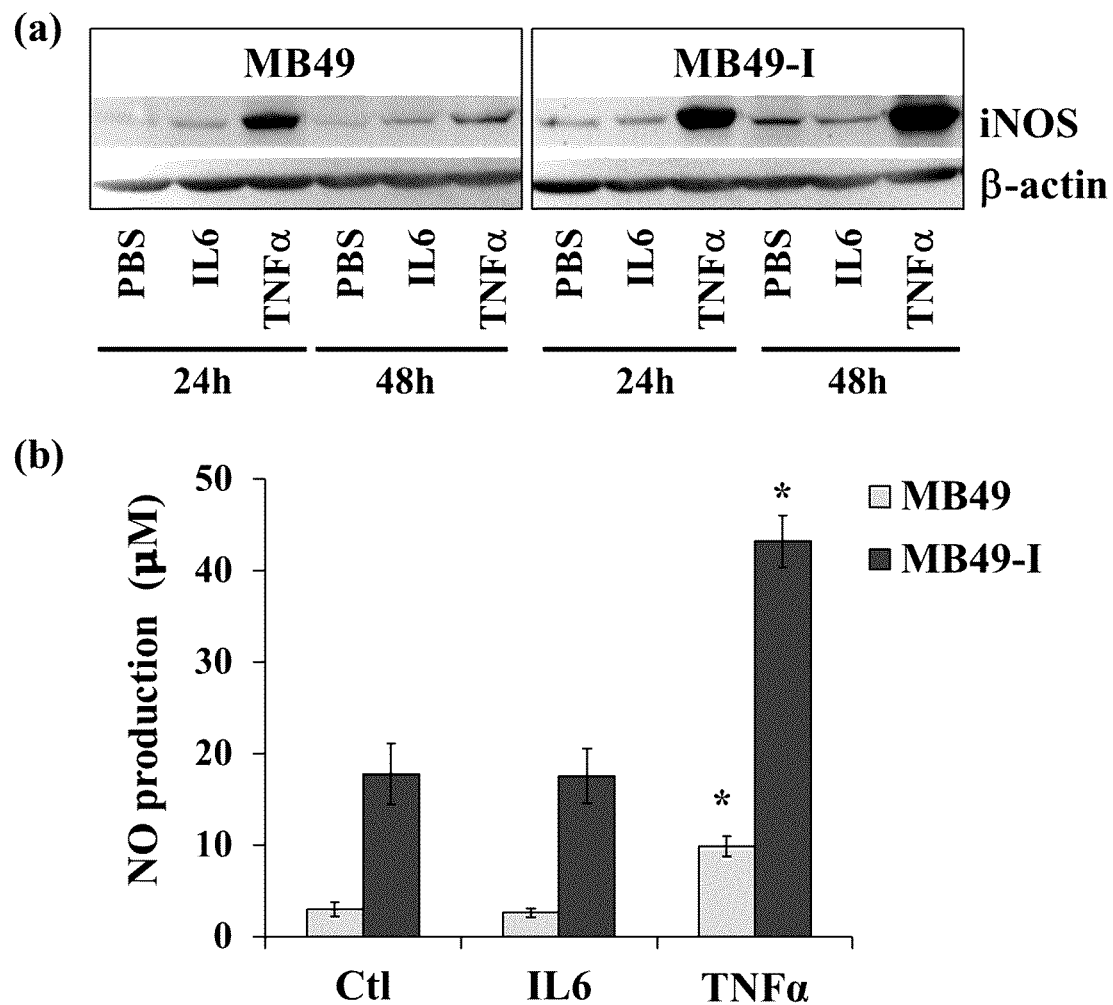
FIG. 16 refers to the regulatory effects of pro-inflammatory IL6 and TNFα in the production of iNOS proteins (a) and NO molecules (b) by MB49 and MB49-I cells. These results shown that non-muscle invasive UBC MB49 cells produced low levels of iNOS and NO relative to highly invasive MB49-I cells in response to TNFα but not IL6. These results strongly support the idea that NO production via inflammatory pathway TNFα/NFκB may provide a permissive environment for MB49-I tumor progression in vivo. *$p<0.01$ compared to control.
Figure 17:
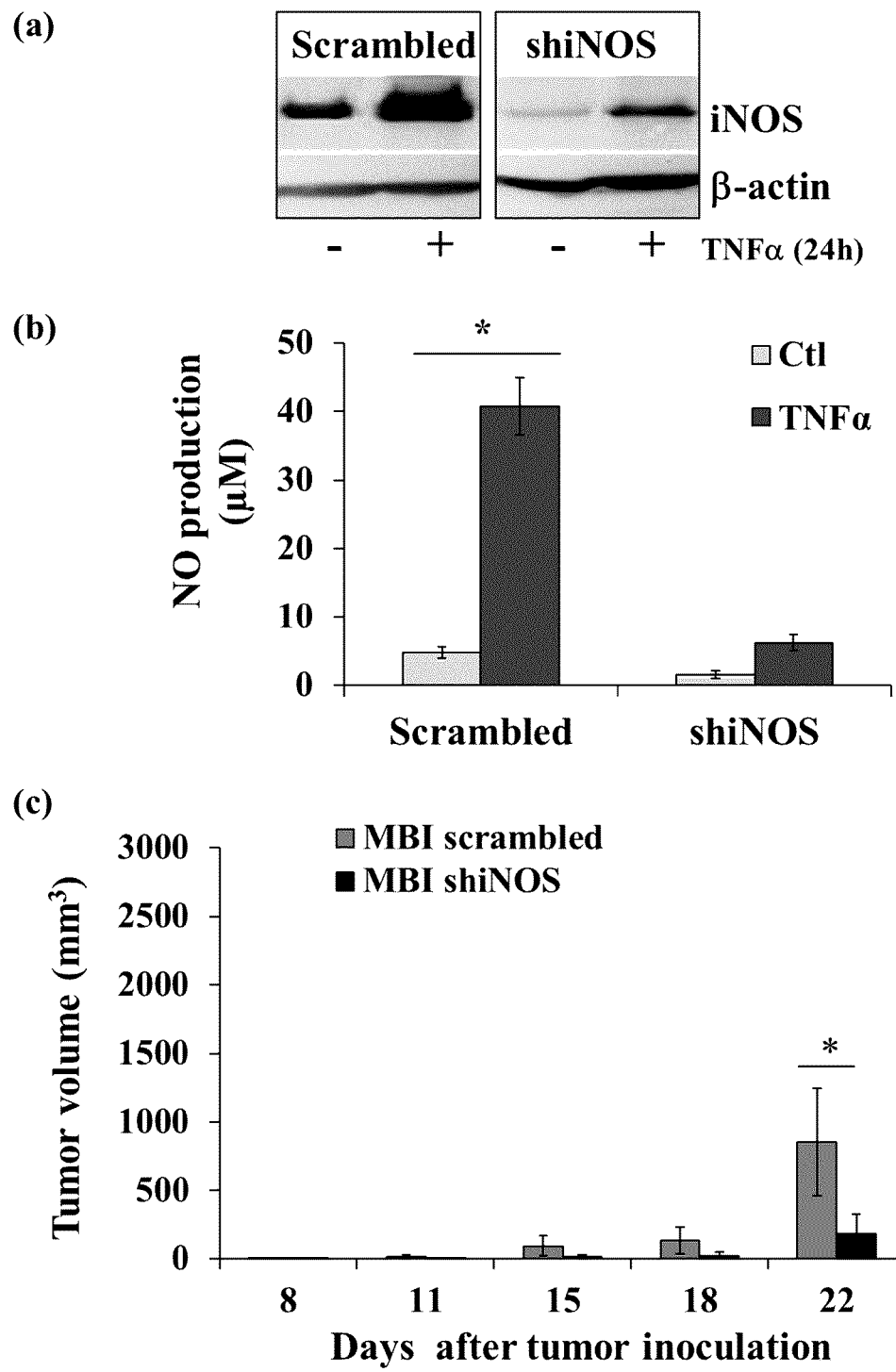
FIG. 17 refers to in vivo study showing loss of basal and TNFα-induced iNOS expression (a) and NO production (b) by shRNA affects luciferase-expressing MB49-I tumor development (c) ectopically implanted in the bladder of C57Bl/6J female mice. These results strongly suggest that MB49-I tumors is probably highly dependent on the presence of functional iNOS/NO system to develop in C57Bl/6J mice *$p<0.01$ compared to control.
Figure 18:
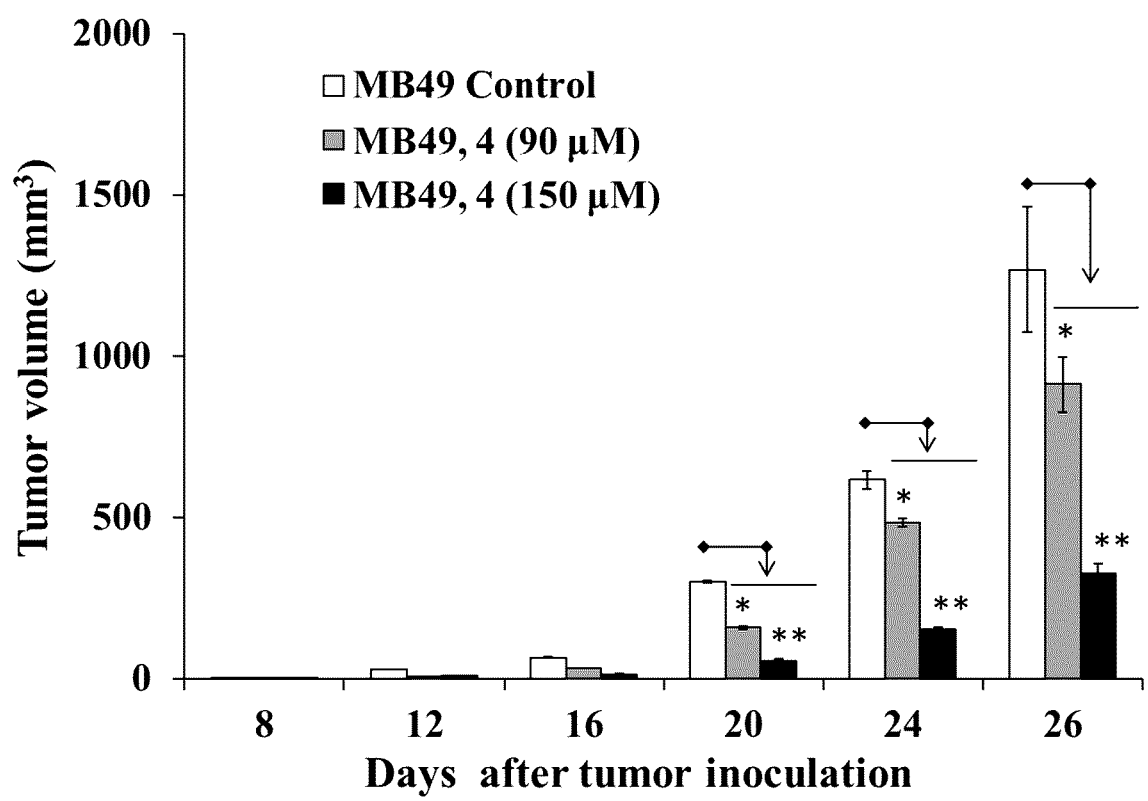
FIG. 18 refers to in vivo targeting study showing the effects of episodic i.p. injections of compound 4 at different concentrations (0, 90, and 150 μM) in C57Bl/6J male mice bearing non-muscle invasive MB49 tumors ectopically implanted in the right flank of animals (n=6). Treatment at 90 and 150 μM significantly reduce the size of subcutaneously implanted MB49 tumors. These results shown that compound 4 is highly efficient to stop the development of UBC tumors producing very low levels of iNOS protein and NO molecules. *$p<0.001$ compared to Ctl.

Referring to FIGS. 13 and 14, male mice implanted ectopically with UBC tumors and treated with compound 4 saw a significant decrease in tumor proliferation and in the number of metastases relative to untreated mice. In female mice bearing orthotopically implanted urothelial bladder cancer tumors, as shown in FIG. 15, anti-proliferative properties of compound 4 were also seen. More particularly, the tumor development was stopped after two weeks of treatment. Similarly, mice ectopically implanted with urothelial bladder cancer tumors and treated with compound 4 saw a significant reduction of the tumor size, as illustrated in FIG. 18.

For example, tumors treated with a compound disclosed herein have a decrease in volume and/or a decrease in tumor growth of at least about 10%, about 20%, about 30%, about 40%, about 50%, about 60%, about 70%, about 80% or about 90% relative to untreated tumors.

Another aspect is a method for decreasing and/or preventing tumor metastases, the method comprising administering to a subject in need thereof an effective amount of at least one compound disclosed herein.

For example, the number of tumor metastases is decreased by at least about 10%, about 20%, about 30%, about 40%, about 50%, about 60%, about 70%, about 80% or about 90% relative to an untreated subject.

Figure 19:
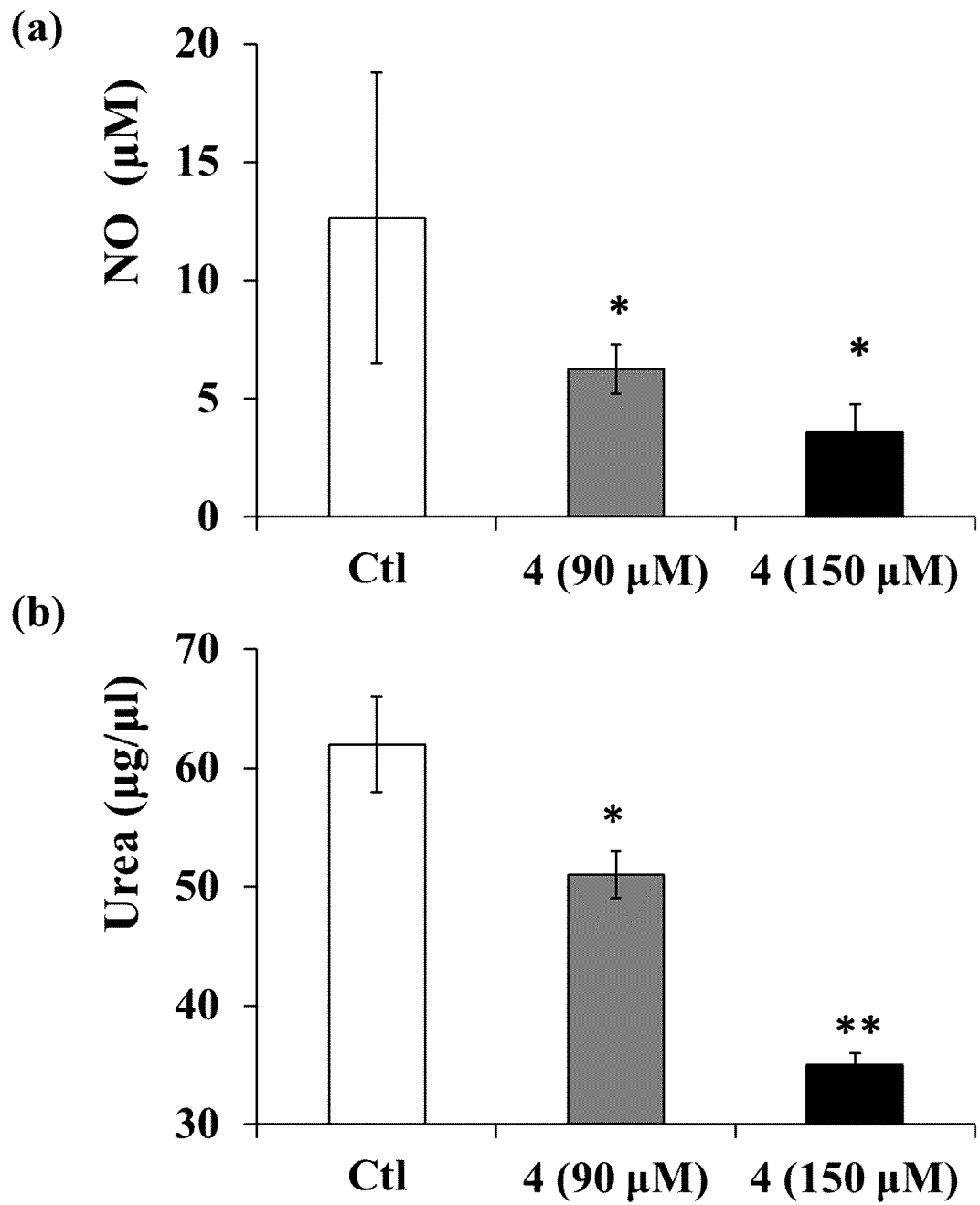
FIG. 19 refers to the anti-inflammatory effects of compound 4 in peritoneal macrophages after in vivo therapeutic targeting of ectopically implanted MB49 tumors in C57Bl/6J male mice. Treatment at 90 and 150 μM significantly decrease NO production (a) and urea synthesis and release (b) in peritoneal macrophages. Peritoneal macrophages were recovered at the end of the study (day 26 after tumor implantation). Polarization to pro-inflammatory M1 macrophages is characterized by NO production through iNOS activity while urea synthesis through arginase-1 activity is related to polarization to anti-inflammatory M2 macrophages. These results strongly suggest that in vivo therapeutic targeting of bladder tumors with compound 4 directly affects macrophage polarization in mice, probably via induction of an «inflammatory anergy» status, a process typically observed in normal intestinal macrophages. *$p<0.05$ and **$p<0.01$ denote significant differences between treatments.
Figure 20:
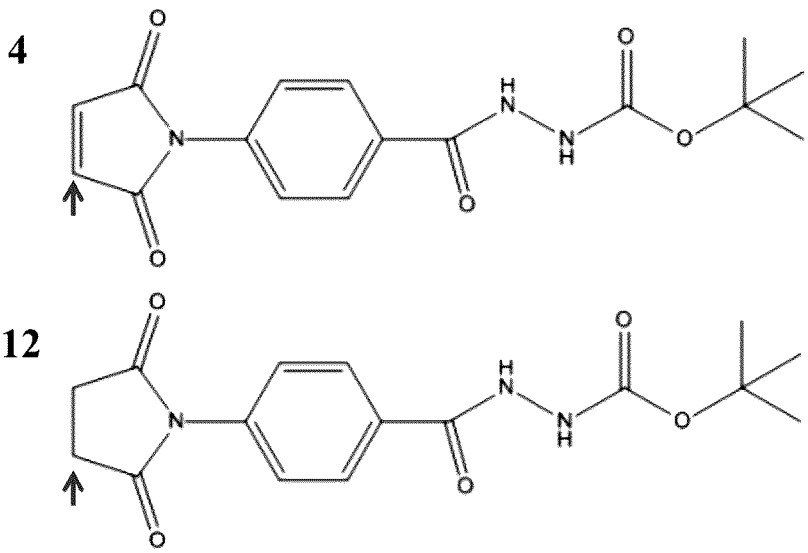
FIG. 20 refers to structure-function relationship study on the anti-inflammatory activity of compound 4. (a) Chemical structures of compounds 4 and 12. (b) Graphical representation of LPS/IFNγ-induced NO production in MB49-I cells after pretreatment with vehicle (DMSO) and the compounds 4 (30 μM) and 12 at different concentrations (10, 20, 37.5 and 50 μM). Compound 12 even at higher concentration does not affect LPS/IFNγ-induced NO synthesis. These results shown that the double bond in the heterocycle of the left part of the molecule is important for the inhibitory effect of compound 4 on NO production by macrophages and tumor cells *$p<0.01$ denote significant difference compared to positive control (DMSO+LPS/IFNγ)
Figure 20:
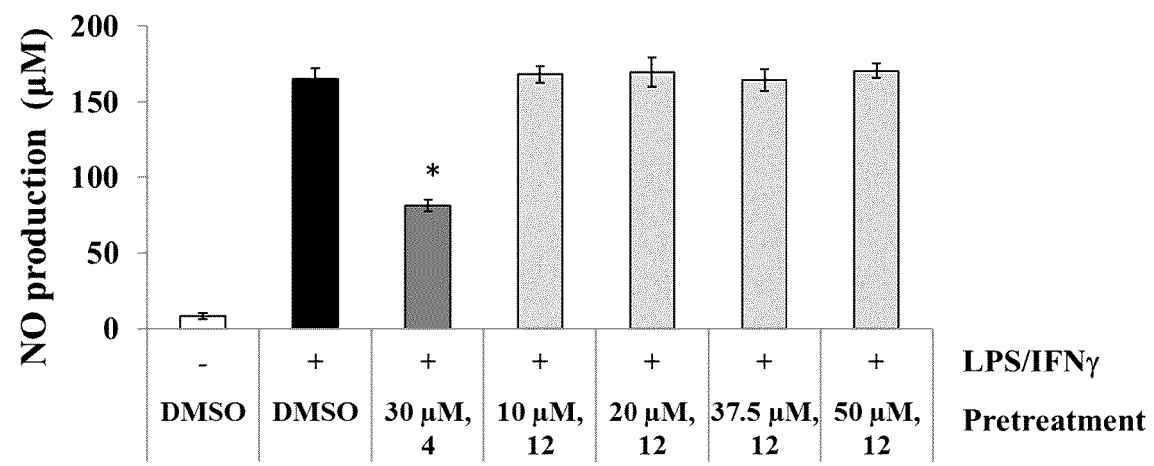

Referring to FIG. 19, further in vivo murine studies of anti-inflammatory properties of compound 4 were conducted and a significant decrease in NO production and urea synthesis was found in peritoneal macrophages.

Derivatives of compound 4 were also found to display anti-inflammatory, anticancer, anti-proliferative and anti-metastatic properties. Additional in vitro and in vivo studies of compound 4 derivatives, compounds 8, 10 and 11 were conducted in macrophages and UBC cells.

Figure 21:
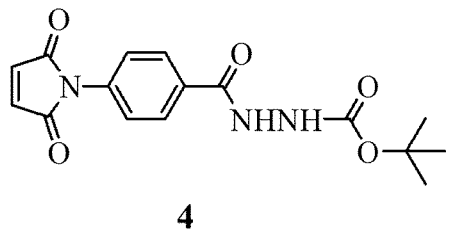
FIG. 21 refers to the comparative effects of compounds 4, 8, 10, and 11 in NO production in MB49-I cells. (a) Chemical structures of compounds 4, 8, 10, and 11; (b) Graphical representation of IFNγ/LPS-induced NO production in MB49-I cells after pretreatment with vehicle (DMSO) and the compounds 4, 8, 10, and 11 at 20 and 37.5 μM. These results shown that compound 8 at the same concentrations (20 and 37.5 μM) is more efficient than compound 4 to inhibit NO production. *$p<0.05$ and **$p<0.01$ denote significant differences between treatments.
Figure 21:
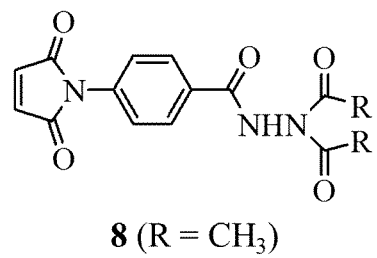
Figure 21:
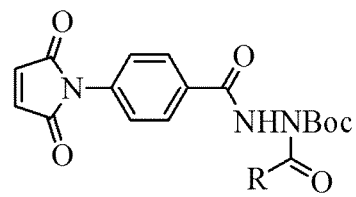
Figure 21:
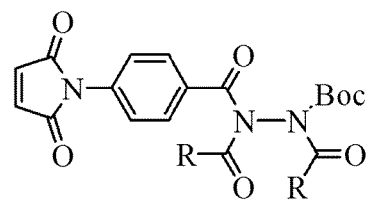
Figure 21:
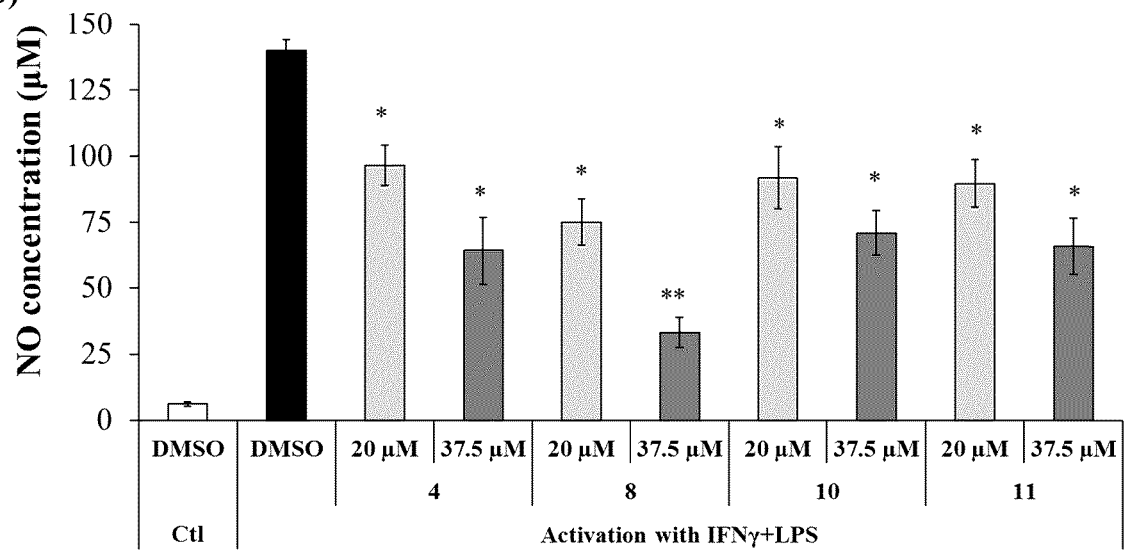
Figure 22:
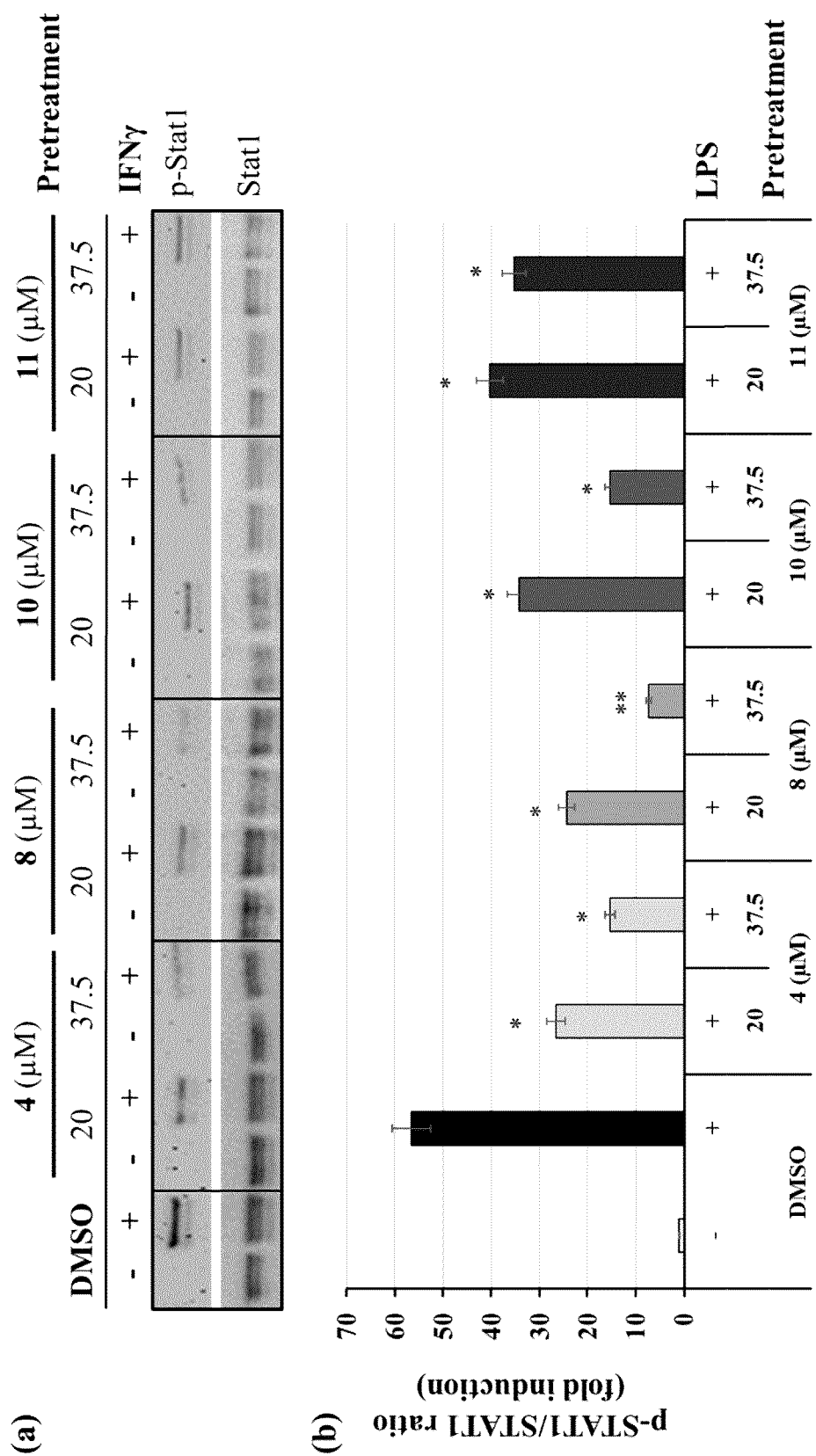
FIG. 22 represents images (a) and graphical analysis (b) showing Western blot analysis to determine the expression level of phosphorylated STAT1 in murine macrophages (RAW 264.7 cells) pretreated for 90 min with vehicle (DMSO) or compounds 4, 8, 10, and 11 (at 20 and 37.5 μM), and then washed and recovered after 15 min of activation with 5 ng/mL IFNγ. The ratio of p-STAT1/STAT1 was calculated from densitometric analysis of each sample to evaluate the relative activation of the transcription factor STAT1. These results shown that compound 8 is more efficient than other compounds to inhibit IFNγ-activated STAT1 signaling pathway in RAW 264.7 cells. *$p<0.05$ and **$p<0.01$ denote significant differences between treatments.
Figure 23:
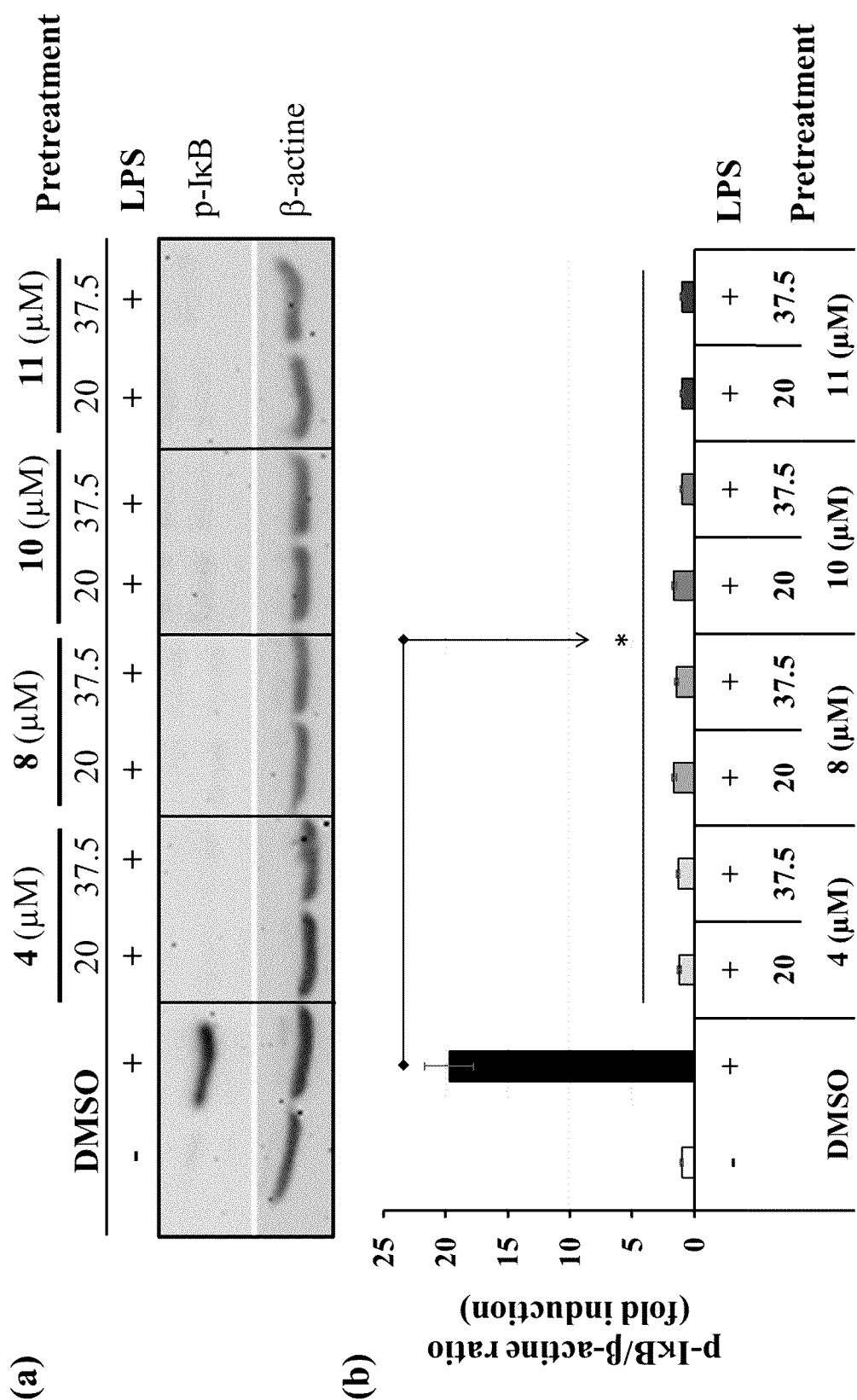
FIG. 23 represents images (a) and graphical analysis (b) showing Western blot analysis to determine the expression level of phosphorylated IκB in murine macrophages (RAW 264.7 cells) pretreated for 90 min with vehicle (DMSO) or compounds 4, 8, 10, and 11 (at 20 and 37.5 μM), and then washed and recovered after 15 min of activation with 100 ng/mL LPS. The ratio of p-IκB/IκB was calculated from densitometric analysis of each sample to evaluate the relative deactivation of IκB proteins, the negative regulator of the transcription factor NFκB. These results shown that all compounds are efficient to inhibit LPS-activated NFκB signaling pathway in RAW 264.7 cells. *p<0.05 and **p<0.01 denote significant differences between treatments.
Figure 24:
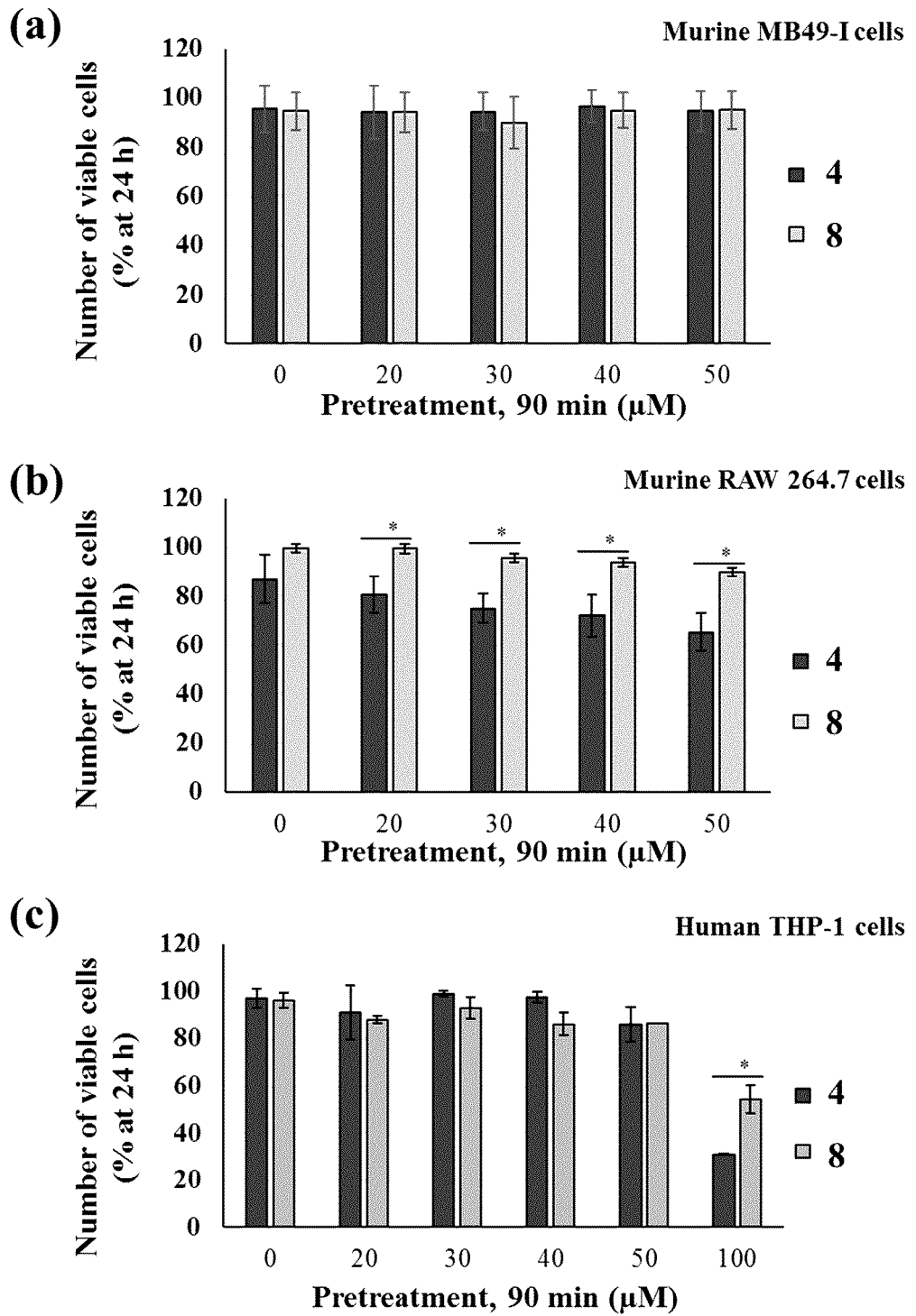
FIG. 24 represents images and graphical analysis showing the comparative effects of compounds 4 and 8 in cell viability of murine UBC MB49-I cells (a), murine macrophages RAW 264.7 cells (b) and human macrophages THP-1 cells (c). Cells were pretreated for 90 min, with vehicle (DMSO) and compounds 4 and 8 at different concentrations, and then washed and counted after a 24-hour period of incubation to estimate the number of viable cells. These results demonstrated that the cytotoxic effect of compound 8 is lower than that of compound 4. *p<0.05 denote significant differences between treatments.

FIG. 21 shows that these compounds were effective in inhibiting NO production. The compounds were also effective in inhibiting the IFNγ-activated STAT1 signaling pathway and the LPS-activated NFκB signaling pathway in macrophage cells (FIGS. 22 and 23).

For example, the LPS-activated NFκB signaling pathway of cells treated with a compound herein disclosed is decreased by at least about 10%, about 20%, about 30%, about 40%, about 50%, about 60%, about 70% or about 80% relative to untreated cells.

Figure 25:
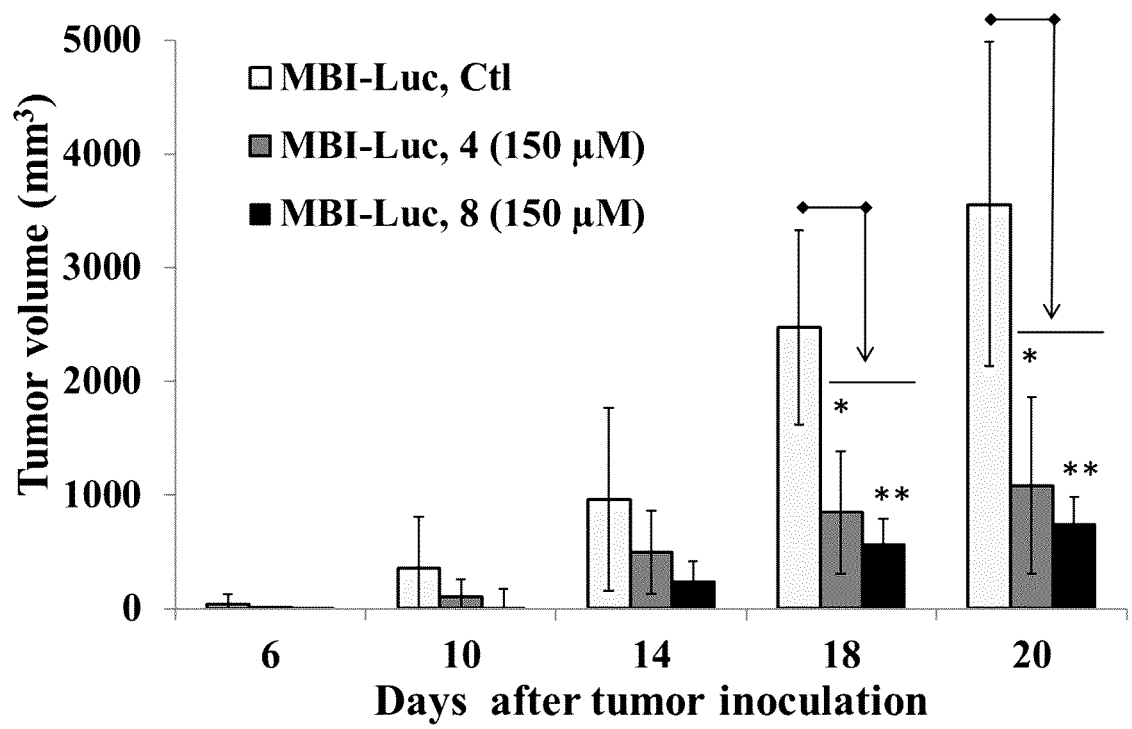
FIG. 25 refers to the comparative anticancer activities of compounds 4 and 8 in the development of MB49-I tumors ectopically implanted in C57Bl/6J male mice. In vivo targeting study showing episodic i.p. injections of compound 8 during 18 days is more efficient than compound 4 to reduce the tumor volume of muscle-invasive MB49-I tumors (n=6) at the same concentration (150 µM). Tumors were chirurgically recovered at the end of the study (day 20 after tumor implantation). These results shown that compound 8 is more efficient than compound 4 to inhibit the development of highly invasive MB49-I tumors. *p<0.05 and **p<0.01 denote significant differences between treatments.

Referring now to FIG. 25, compounds 4 and 8 were found to have anti-proliferative activity in ectopically implanted UBC tumors in male mice.

For example, the compound is compound 4.
For example, the compound is compound 8.
For example, the compound is compound 10.
For example, the compound is compound 11.
For example, the subject is a mammal. For example, the subject is a human.
For example, the cell is in vitro.
For example, the cell is in vivo.
For example, the cell is a cancer cell.
For example, the cancer is melanoma, uterine cancer, ovarian cancer, prostate cancer or bladder cancer.
For example, the bladder cancer is superficial UBC or muscle invasive UBC.
For example the tumor is a melanoma tumor, uterine tumor, ovarian tumor, prostate tumor or bladder tumor.
For example, the bladder tumor is a superficial UBC tumor or a muscle invasive UBC tumor.
For example, the methods disclosed herein are effective for presenting the development of superficial UBC into muscle invasive UBC tumor.

In the present disclosure, the following abbreviations are used:

| Abbreviation | Meaning |
|---|---|
| Ac$_2$O | Acetic anhydride |
| AcONa | Sodium acetate |
| CH$_2$Cl$_2$ | Dichloromethane |
| Boc | t-Butyloxycarbonyl |
| Et$_2$O | Diethyl ether |
| EtOAc | Ethyl acetate |
| Et$_3$N | Triethyl amine |
| h | Hour |
| HCl | Chlorhydric acid |
| i.p. | Intraperitoneal |
| m | Meta |
| MA | Maleic anhydride |
| MeOH | Methanol |
| min | Minute |
| mmol | Millimole |
| MTT | 3-(4,5-Dimethylthiazol-2-yl)-2,5-diphenyltetrazolium bromide |
| NMR | Nuclear magnetic resonance |
| o | Ortho |
| p | Para |
| Phe | Phenyl |
| s.c. | Subcutaneously |
| TLC | Thin layer chromatography |
| TFA | Trifluoroacetic acid |
| UBC | Urothelial bladder cancer |

EXAMPLES

This section also describes the synthesis of several compounds that are presented in this document. These examples are not to be construed as limiting the scope of the present disclosure in any way.

Materials and Methods—Chemistry

Anhydrous reactions were performed under an inert atmosphere, the set-up assembled and cooled under dry nitrogen. Unless otherwise noted, starting material, reactant and solvents were obtained commercially and were used as such or purified and dried by standard means.[13] Organic solutions were dried over magnesium sulfate, evaporated on a rotatory evaporator and under reduced pressure. All reactions were monitored by UV fluorescence, or staining with iodine. Commercial TLC plates were Sigma T 6145 (polyester silica gel 60 Å, 0.25 mm). Flash column chromatography was performed according to the method of Still and co-workers on Merck grade 60 silica gel, 230-400 mesh.[14] All solvents used in chromatography had been distilled prior to use.

The infrared spectra were taken on a Nicolet Impact 420 FT-IR. Mass spectral assays were obtained using a MS model 6210, Agilent technology instrument. The high resolution mass spectra (HRMS) were obtained by TOF (time of flight) using ESI (electrospray ionization) using the positive mode (ESI+). (Plateforme analytique pour molécules organiques de l'Université du Québec à Montréal).

Nuclear magnetic resonance (NMR) spectra were recorded on a Varian 200 MHz NMR apparatus. Samples were dissolved in deuterochloroform (CDCl$_3$), deuteroacetone (acetone-d$_6$) or deuterodimethylsulfoxide (DMSO-d$_6$) for data acquisition using tetramethylsilane or chloroform as internal standard (TMS, δ 0.0 ppm for $^1$H-NMR and CDCl$_3$ δ 77.0 ppm for $^{13}$C-NMR). Chemical shifts (δ) are expressed in parts per million (ppm), the coupling constants (J) are expressed in hertz (Hz). Multiplicities are described by the following abbreviations: s for singlet, d for doublet, dd for doublet of doublets, t for triplet, dt for doublet of triplets, q for quartet, dq for doublet of quartets, m for multiplet, # m for several multiplets, br for a broad signal.

The following compounds were prepared from a relevant aminobenzoic acid derivative using the procedures summarized in schemes 1, 2, 3 or 4.

Example 1

Preparation of N'-[4-(2,5-dioxo-2,5-dihydro-pyrrol-1-yl)-benzoyl]-hydrazine carboxylic acid tert-butyl ester (4), its hydrochloric acid salt (5) and its trifluoroacetic acid salt (6)

Step A. Synthesis of 4-(3-carboxy-acryloylamino)-benzoic acid (2)

4-Aminobenzoic acid (1, 5.34 g, 38.93 mmol) was dissolved in dry acetone (12 mL) to which was added methanol (1 mL). Maleic anhydride (1.05 eq.) dissolved in dry acetone was added to the first solution. The reaction mixture was stirred for a period of 2 h allowing sufficient time for the complete precipitation of the diacid 2. The precipitate was filtered and washed twice with acetone (2×2 mL) and dried in a desiccator overnight. The crude diacid 2 (9.16 g, 90%) was sufficiently pure to be use without further purification at the next step. IR (v, cm-1): 3500-2500 (CO$_2$H), 1686 cm-1 (C=O); $^1$H NMR (DMSO-d$_6$, δ ppm): 12.79 (br s, 2H, 2×CO$_2$H), 10.58 (s, 1H, NH), 7.89 and 7.71 (2×d, J=8.6 Hz, 4H, aromatic), 6.48 and 6.30 (2×d, J=12.2 Hz, 2H, maleimide); $^{13}$C NMR (DMSO-d$_6$, δ ppm): 167.4, 167.3, 164.1, 143.2, 132.1, 130.9 (2), 130.6, 126.0, 119.2 (2); ESI+ HRMS: (M+H)+ calculated for C$_{11}$H$_{10}$NO$_5$=236.0553; found=236.0558.

Step B. Synthesis of 4-(2,5-dioxo-2,5-dihydro-pyrrol-1-yl)-benzoic acid (3)

The diacid 2 (2.01 g, 8.54 mmol) was treated with acetic anhydride (4.0 mL, 36.28 mmol) and anhydrous sodium acetate (350 mg, 4.27 mmol) and the mixture heated at 50° C. for 2 h. Afterwards, the solution was evaporated to dryness and stirred with water at 70° C. for a period of 2 h. The resulting precipitate was filtered and dried in a desiccator overnight to yield 1.65 g (89%) of maleimide 4. The spectral data of this derivative correspond to those reported in the literature.[9,11] IR (v, cm-1): 3475-2600 ($CO_2H$), 1715 (C=O), 1704 (C=O); $^1$H NMR (acetone-$d_6$, δ ppm): 8.14 and 7.57 (2×d, J=8.6 Hz, 4H, aromatic), 7.08 (s, 2H, maleimide); $^{13}$C NMR (acetone-$d_6$, δ ppm): 169.3 (2), 166.2, 136.2, 134.7 (2), 130.1 (2), 129.3, 125.8 (2); ESI+ HRMS: (M+H)+ calculated for $C_{11}H_8NO_4$=218.0448; found=218.0447.

Step C. Synthesis of N'-[4-(2,5-dioxo-2,5-dihydro-pyrrol-1-yl)-benzoyl]-hydrazine carboxylic acid tert-butyl ester (4)

Derivative 4 was synthesized using a modified procedure reported by Willner et al.[15] as it is also described by Lau et al. and Hamelin-Morrissette et al.[9-11] A cooled suspension (0° C.) of molecule 3 (211 mg, 0.97 mmol) in methylene chloride (4.5 mL) was treated with triethylamine (190 μL, 1.36 mmol) and isobutyl chloroformate (175 μL, 1.34 mmol). The mixture was stirrred for 1 h at 0° C. and at room temperature (22° C.) for about 1 h. Afterwards, tert-butyl carbazate (128 mg, 0.97 mmol) dissolved in methylene chloride (0.8 mL) was added dropwise to the mixture and stirred for an additional 12 h at 22° C. The reaction mixture was diluted with ethyl acetate (55 mL) and methylene chloride (20 mL) and washed twice with saturated $NaHCO_3$ (2×50 mL), twice with 0.1 N HCl (2×50 mL), twice with saturated NaCl (2×50 mL), and finally with $H_2O$ (50 mL). The organic phase was dried ($MgSO_4$) and evaporated to give crude derivative 4. The product was purified by flash chromatography, using a mixture of hexanes/acetone (3/2), to yield 173 mg (54%) of 4. The spectral data of this derivative correspond to those reported in the literature.[10] IR (v, cm$^{-1}$): 3360-3240 (NH), 3087 (C=C), 2988 (CH, aliphatic), 1733 (C=O), 1706 (C=O); $^1$H NMR (acetone-$d_6$, δ ppm): 9.05 (s, 1H, NH), 8.02 and 7.53 (2×d, J=8.6 Hz, 4H, aromatic), 7.07 (s, 2H, maleimide), 2.84 (br s, 1H, NH), 1.45 (s, 9H, 3×$CH_3$); $^{13}$C NMR (acetone-$d_6$, δ ppm): 169.3 (2), 166.0, 155.7, 135.1, 134.6 (2), 131.6, 127.9 (2), 125.9 (2), 79.6, 27.5 (3); ESI+ HRMS: (M+Na)+ calculated for $C_{16}H_{17}N_3NaO_5$=354.1060; found=354.1072; (M-2-methylpropene+H)+ calculated for $C_{12}H_{11}N_3O_5$=276.0620; found=276.0627.

Step D. Synthesis of 4-(2,5-dioxo-2,5-dihydro-pyrrol-1-yl)-benzoic acid hydrazide hydrochloride (or 4-maleimidbenzoic acid hydrazide hydrochloride) (5)

The hydrolysis of 4 was performed using a similar procedure reported by Heindel et al. for the cleavage of maleimidoacetic acid (tert-butyloxycarbonyl) hydrazide with hydrochloric acid to form maleimidoacetic acid hydrazide hydrochloride.[16] To a solution of 4 (2.41 g, 7.27 mmol) dissolved in dry dioxane (30 mL) was added a solution of hydrochloric acid (60 mL, 1.0 M in diethyl ether, 60 mmol). The mixture was stirred at room temperature for a period of 5 hours. Afterwards, 150 mL of hexanes were added to complete the precipitation of the hydrochloride salt 5. The crude precipitated was filtered, washed with hexanes and recrystallized twice with a mixture of methanol/isopropyl alcohol/hexanes (8/3/10) to yield 1.7 g (46%) of the desired material. IR (v, cm$^{-1}$): 3200-2500 ($CO_2H$), 3269 (NH), 1702 (C=O), 1693 (C=O); $^1$H NMR (DMSO-$d_6$, δ ppm): 8.06 and 7.52 (2×d, J=8.8 Hz, 4H, aromatic), 7.21 (s, 2H, maleimide); $^{13}$C NMR (DMSO-$d_6$, δ ppm): 170.0 (2), 165.6, 135.9, 135.4 (2), 129.6, 129.0 (2), 126.8 (2); ESI+ HRMS: (M+H)+ calculated for $C_{11}H_{10}N_3O_3$=232.0717; found=232.0717 and ESI+ HRMS: (M+H)+ calculated for $C_{11}H_{11}ClN_3O_3$=268.0483; found=268.0483.

Step E. Synthesis of 4-(2,5-dioxo-2,5-dihydro-pyrrol-1-yl)-benzoic acid hydrazide trifluoroacetic acid salt (6)

A solution of 4 (106 mg, 0.32 mmol) dissolved in trifluoroacetic acid (0.5 mL) was stirred at 0° C. for a period of 30 minutes. Afterwards, the excess trifluoroacetic acid was removed under vacum at 22° C. to give compound 6 quantitatively. IR (v, cm$^{-1}$): 3500-2500 ($CO_2H$), 3277 (NH), 1710 (C=O); $^1$H NMR (DMSO-$d_6$, δ ppm): 11.62 (br s, 1H, N$\underline{H}$NH$_3^+$CF$_3$CO$_2^-$), 8.63 (br s, NH$_3^+$), 8.01 and 7.56 (2×d, J=8.5 Hz, 4H, aromatic), 7.24 (s, 2H, maleimide); $^{13}$C NMR (DMSO-$d_6$, δ ppm): 169.6 (2), 165.4, 135.5, 135.0 (2), 129.4, 128.4 (2), 126.5 (2).

Example 2

Preparation of N'-[3-(2,5-dioxo-2,5-dihydro-pyrrol-1-yl)-4-chloro-benzoyl]-hydrazine carboxylic acid tert-butyl ester (4a)

Following the procedure of Example 1, steps A-C described above using 3-amino-4-chloro benzoic acid as the starting material instead of 4-amino benzoic acid derivative 4a was prepared efficiently.

Step A. Synthesis of 3-(cis-3-carboxy-acryloylamino)-4-chloro benzoic acid (2a)

Spectral data for 2a: IR (v, cm$^{-1}$): 3500-2500 ($CO_2H$), 3310 (NH), 1696 (C=O); $^1$H NMR (DMSO-$d_6$, δ ppm): 13.08 (s, 2H, 2×$CO_2H$), 10.13 (s, 1H, NH), 8.37 (s, 1H, aromatic) 7.72 and 7.61 (2×d, 2H, J=10.0 Hz, aromatic), 6.59 and 6.34 (2×d, 2H, J=12.0 Hz, maleimide); $^{13}$C MNR (DMSO-$d_6$, δ ppm); 167.5, 166.7, 164.1, 135.0, 131.6, 131.2 (2), 130.4 (2), 127.2 (2).

Step B. Synthesis of 3-(2,5-dioxo-2,5-dihydro-pyrrol-1-yl)-4-chloro benzoic acid (3a)

Spectral data for 3a: IR (v, cm$^{-1}$): 3300-2500 ($CO_2H$), 3490 (amine), 1674 (C=O). $^1$H NMR (acetone-$d_6$, δ ppm): 8.1 (m, 2H, aromatic), 7.76 (d, 1H, J=8.0 Hz, aromatic), 7.14 (s, 2H, maleimide) $^{13}$C NMR (acetone-$d_6$, δ ppm): 168.7 (2), 165.0, 143.0, 137.84, 134.9 (2), 132.3, 131.6, 130.6, 130.2.

Step C. Synthesis of N'-[3-(2,5-dioxo-2,5-dihydro-pyrrol-1-yl)-4-chloro-benzoyl]-hydrazine carboxylic acid tert-butyl ester (4a)

Spectral data for 4a: IR (v, cm$^{-1}$): 3494 (amine), 3090 (C=C), 2974 (aliphatic), 1717 (C=O). $^1$H NMR (acetone-$d_6$, δ ppm): 9.71 (s, 1H, NH), 8.05 (dd, 1H, J=8.2 Hz and J=1.8 Hz, aromatic) 7.95 (d, 1H, J=1.8 Hz, aromatic), 7.75 (d, 1H, J=8.6 Hz, aromatic), 7.11 (s, 2H, maleimide), 2.91 (s, 1H, NH), 1.43 (s, 9H, 3×$CH_3$); $^{13}$C NMR (acetone-$d_6$, δ ppm): 169.5 (2), 166.0, 156.5, 135.0 (2), 134.0 (2), 130.0, 130.7, 129.0 (2), 80.0, 28.1 (3).

Example 3

Preparation of N'-[4-(2,5-dioxo-2,5-dihydro-pyrrol-1-yl)-2-chloro-benzoyl]-hydrazine carboxylic acid tert-butyl ester (4b)

Following the procedure of Example 1, steps A-C described above using 4-amino-2-chloro benzoic acid as the starting material instead of 4-amino benzoic acid derivative 4b was prepared efficiently.

Step A. Synthesis of 4-(cis-3-carboxy-acryloylamino)-2-chloro benzoic acid (2b)

Spectral data for 2b: IR (v, cm$^{-1}$): 3500-2500 (CO$_2$H), 3262 (NH), 1689 (C=O); $^1$H NMR (DMSO-d$_6$, δ ppm): 13.8 (s, 2H, 2×CO$_2$H), 10.7 (s, 1H, NH), 7.85 (m, 2H, aromatic) 7.55 (dd, 1H, J=10.0 Hz and J=2.0 Hz, aromatic), 6.45 and 6.31 (2×d, 2H, J=12.0 Hz, maleimide); $^{13}$C MNR (DMSO-d$_6$, δ ppm): 168.0, 166.0, 164.0, 143.0, 136.5, 135.0, 132.0, 131.5, 126.0, 121.5, 119.2.

Step B. Synthesis of 3-(2,5-dioxo-2,5-dihydro-pyrrol-1-yl)-4-chloro benzoic acid (3b)

Spectral data for 3b: IR (v, cm$^{-1}$): 3300-2500 (CO$_2$H), 3470 (amine), 1723 (C=O). $^1$H NMR (acetone-d$_6$, δ ppm): 7.90 (d, 1H, J=8.6 Hz, aromatic), 7.67 (d, 1H, J=2.2 Hz, aromatic), 7.50 (dd, 1H, J=8.3 Hz and J=2.0 Hz, aromatic) 7.11 (s, 2H, maleimide); $^{13}$C NMR (acetone-d$_6$, δ ppm): 168.0 (2), 165.0, 138.0, 136.0 (2), 135.0, 132.0, 128.0, 124.0, 118.0.

Step C. Synthesis of N'-[3-(2,5-dioxo-2,5-dihydro-pyrrol-1-yl)-4-chloro-benzoyl]-hydrazine carboxylic acid tert-butyl ester (4b)

Spectral data for 4b: IR (v, cm$^{-1}$): 3473 (amine), 3090 (C=C), 2984 (aliphatic), 1708 (C=O). $^1$H NMR (acetone-d$_6$, δ ppm): 9.03 (s, 1H, NH), 7.65 (d, 1H, J=8.0 Hz, aromatic) 7.59 (d, 1H, J=1.6 Hz, aromatic), 7.45 (dd, 1H, J=8.2 and J=1.8 Hz aromatic), 7.08 (s, 2H, maleimide), 2.96 (s, 1H, NH), 1.47 (s. 9H, 3×CH$_3$); $^{13}$C NMR (acetone-d$_6$, δ ppm): 169.0 (2), 166.0, 156.0, 135.0 (2), 134.6, 133.0, 131.0, 127.9(2), 125.9, 80.0, 27.5 (3).

Example 4

Preparation of N'-[4-(2,5-dioxo-pyrrolidin-1-yl)-benzoyl]-hydrazine carboxylic acid tert-butyl ester (12)

Maleimide 4 (103 mg, 0.31 mmol) was dissolved in methanol (1 mL) to which was added 5% Pd/C (14 mg). Some hydrogen gas was bubbled during 30 seconds into the mixture. The suspension was stirred vigorously under a hydrogen atmosphere for a period of 3 hours. Of note, a longer period of time is required on a larger scale. Afterwards, the suspension was filtered on silica with a mixture of hexanes/acetone (3/2) as the eluent, to yield 87 mg (84%) of 12. IR (v, cm$^{-1}$): 3400-3100 (NH), 2981 (CH), 1703 (C=O); $^1$H NMR (acetone-d$_6$, δ ppm): 9.54 (br s, 1H, NH), 8.00 and 7.45 (2×d, J=8.6 Hz, 4H, aromatic), 1.45 (s, 9H, 3×CH$_3$); $^{13}$C NMR (acetone-d$_6$, δ ppm) 176.2 (2), 165.9, 155.7, 136.1, 132.4, 127.8 (2), 126.7 (2), 79.6, 28.2, 27.5; ESI+ HRMS: (M+H)+ calculated for C$_{16}$H$_{20}$N$_3$O$_5$=334.1397; found=334.1391 and ESI+ HRMS: (M+H-C$_4$H$_9$)+ calculated for C$_{12}$H$_{12}$N$_3$O$_5$=278.0771; found=278.0769.

Example 5

Preparation of 4-(2,5-dioxo-2,5-dihydro-pyrrol-1-yl)-benzoic acid N'-diacetyl-hydrazide (8, R=CH$_3$)

To a solution of crude 6 (444 mg, 1.28 mmol) dissolved in dichloromethane (10 mL) was added triethylamine (1.07 mL, 780 mg, 7.7 mmol) and acetic anhydride (0.61 mL, 659 mg, 6.4 mmol). The mixtured was stirred at 22° C. for about 30 minutes. Afterwards, the organic phase was diluted with ethyl acetate (75 mL) directly into an extraction funnel. The organic phase was washed successively with a 5% sodium bicarbonate aqueous solution (50 mL), with a 10% sodium chloride aoous solution (50 mL) and finnally with water (50 mL). The organic phase was dried with anhydrous magnesium sulfate, filtered and evaporated to the crude material (111 mg). The product was purified by flash column chromatography using a mixture of hexanes/acetone (7/3) to give 75 mg (18%) of the desired material 8, R=CH$_3$). Of note, different anhydrides or alkaloyl chlorides can be used to produce analogs of this specific derivative. IR (v, cm$^{-1}$): 3200 (NH), 1702 (C=O), 1662 (C=O); $^1$H NMR (acetone-d$_6$, δ ppm): 10.15 (br s, 1H, NH), 8.09 and 7.61 (2×d, J=8.6 Hz, 4H, aromatic), 7.10 (s, 2H, maleimide), 2.41 (s, 6H, 2×CH$_3$); $^{13}$C NMR (acetone-d$_6$, δ ppm): 171.1 (2), 169.3 (2), 166.0, 135.8, 134.7 (2), 130.8, 128.2 (2), 126.1 (2), 24.2 (2). ESI+ HRMS: (M+H)+ calculated for C$_{15}$H$_{14}$N$_3$O$_5$=316.0928; found=316.0945 and ESI+ HRMS: (M+H-Ac)+ calculated for C$_{13}$H$_{12}$N$_3$O$_4$=275.08252; found=275.0856.

Example 6

Preparation of N-acetyl-N-[4-(2,5-dioxo-2,5-dihydro-pyrrol-1-yl)-benzoyl]-hydrazinecarboxylic acid tert-butyl ester (10, R=CH$_3$)

To a solution of 4 (100 mg, 0.30 mmol) dissolved in dichloromethane (3 mL) was added triethylamine (252 μL, 183 mg, 1.81 mmol) and acetic anhydride (71 μL, 76.7 mg, 0.75 mmol). The mixtured was stirred at 22° C. for about 30 minutes. Afterwards, the organic phase was diluted with ethyl acetate (25 mL) directly into an extraction funnel. The organic phase was washed successively with a 5% sodium bicarbonate aqueous solution (10 mL), with a 10% sodium chloride aoous solution (10 mL) and finnally with water (20 mL). The organic phase was dried with anhydrous magnesium sulfate, filtered and evaporated to the crude material (123 mg). The product was purified by flash column chromatography using a mixture of hexanes/acetone (4/1) to give 22 mg (20%) of the desired material 10, R=CH$_3$). It is noteworthy, that a longer reaction time (2 hours) lead to higher yield of the desired material. However, some diacetylated product (11) is also present as a side product. IR (v, cm$^{-1}$): 3286 (NH), 1753 (C=O), 1711 (C=O), 1652 (C=O); $^1$H NMR (CDCl$_3$, δ ppm): 8.28 (br s, 1H, NH), 7.90 and 7.50 (2×d, J=8.6 Hz, 4H, aromatic), 6.89 (s, 2H, maleimide), 2.61 (s, 3H, CH$_3$), 1.51 (s, 9H, 3×CH$_3$); $^{13}$C NMR (CDCl$_3$, δ ppm): 170.5, 168.9 (2), 165.2, 151.0, 135.0, 134.4 (2), 130.9, 128.3 (2), 125.7 (2), 84.8, 27.8 (3), 25.5;

ESI+ HRMS: (M+Na)+ calculated for $C_{18}H_{19}N_3NaO_6$=396.1166; found=396.1165 and ESI+ HRMS: (M+H-tert-Boc)+ calculated for $C_{13}H_{12}N_3O_4$=274.0822; found=274.0824.

Example 7

Preparation of N,N'-diacetyl-N'-[4-(2,5-dioxo-2,5-dihydro-pyrrol-1-yl)-benzoyl]-hydrazinecarboxylic acid tert-butyl ester (11, R=CH$_3$)

To a solution of 4 (100 mg, 0.30 mmol) dissolved in dichloromethane (3 mL) was added triethylamine (252 µL, 183 mg, 1.81 mmol) and acetyl chloride (54 µL, 60 mg, 0.75 mmol). The mixtured was stirred at 22° C. for about 2 hours. Afterwards, the organic phase was diluted with ethyl acetate (25 mL) directly into an extraction funnel. The organic phase was washed successively with a 5% sodium bicarbonate aqueous solution (10 mL), with a 10% sodium chloride aoous solution (10 mL) and finally with water (20 mL). The organic phase was dried with anhydrous magnesium sulfate, filtered and evaporated to the crude material (118 mg). The product was purified by flash column chromatography using a mixture of hexanes/acetone (4/1) to give 100 mg (80%) of the desired material 11, R=CH$_3$). IR (v, cm$^{-1}$): 3193 (NH), 1701 (C=O), 1660 (C=O); $^1$H NMR (CDCl$_3$, δ ppm): 7.68 and 7.50 (2×d, J=8.6 Hz, 4H, aromatic), 6.89 (s, 2H, maleimide), 2.49 and 2.48 (2×s, 6H, 2×CH$_3$), 1.50 (s, 9H, 3×CH$_3$); $^{13}$C NMR (CDCl$_3$, δ ppm): 170.2, 169.9 (2), 168.8 (2), 150.2, 134.6, 134.4 (2), 132.9, 128.2 (2), 125.0 (2), 85.9, 27.8 (3), 25.4, 24.6; ESI+ HRMS: (M+Na)+ calculated for $C_{20}H_{21}N_3NaO_7$=438.1272; found=438.1281 and ESI+ HRMS: (M+H-Ac and -tert-Boc)+ calculated for $C_{13}H_{12}N_3O_4$=274.0822; found=274.0833.

Example 8

Preparation of N'-{4-[3-(2-tert-butoxycarbonylamino-ethylsulfanyl)-2,5-dioxo-pyrrolidin-1-yl]-benzoyl}-hydrazinecarboxylic acid tert-butyl ester (13)

To a solution of 4 (115 mg, 0.34 mmol) dissolved in methanol (3 mL) was added 2-(Boc-amino) ethanethiol (70 µL, 73 mg, 0.41 mmol). The mixture was stirred at 22° C. for 2 hours and at 50° C. for 1 hour. The organic phase was diluted with ethyl acetate (30 mL) directly into an extraction funnel and washed successively with a 5% sodium bicarbonate aqueous solution (2×10 mL) and with water (2×20 mL). The organic phase was dried with anhydrous magnesium sulfate, filtered and evaporated to the crude material (191 mg). The product was purified by flash column chromatography using a mixture of hexanes/acetone (3/2) to give 107 mg (61%) of the desired material 15. IR (v, cm$^{-1}$): 3300 (NH), 1707 (C=O), 1680 (C=O); $^1$H NMR (CDCl$_3$, δ ppm): 8.80 (br s, 1H, NH), 7.86 and 7.34 (2×d, J=8.2 Hz, 4H, aromatic), 6.90 (br s, 1H, NH), 5.07 (br s, 1H, NH), 3.98 (1H, m, —CHS—) 2.6-3.6 (several m, 6H, 3×-CH$_2$—), 1.50 and 1.45 (2×s, 18H, 2×3×CH$_3$); $^{13}$C NMR (CDCl$_3$, δ ppm): 175.4, 173.2, 165.8, 155.9 (2), 134.8, 131.7, 128.2 (2), 126.4 (2), 82.1, 79.7, 39.4, 38.9, 36.1, 32.7, 28.4 (3), 28.2 (3); ESI+ HRMS: (M+Na)+ calculated for $C_{23}H_{32}N_4NaO_7S$=531.1884; found=531.1881.

Example 9

General Procedure for the Preparation of Derivatives of General Structure 13 (See Scheme 3)

Following the procedure described by Taha et al.[12] compound 5 can be treated with a relevant aldehyde (alkyl aldehydes (linear or branched), benzaldehyde or substituted benzaldehydes) under acidic conditions at reflux in butanol (or other solvent) to give the desired alkylhydrazones or benzoylhydrazones derivatives.

Example 10

General Procedure for the Preparation of Derivatives 14, 15 or 16 (See Scheme 4)

Derivative 4 (or any other maleimides described herein) can be reacted with an appropriate diene (butadiene (unsubstituted or substituted), cyclopentadiene, cyclohexadiene cycloheptadiene, furane, thiophene, pyrrole, N-alkylpyrrole) to give the desired cycloadducts (Diels-Alder products) such as for example 14, 15 and 16. This reaction can be performed by heating the pure reagents (diene and dienophile) either neat or in solution, with or without pressure.

Example 11

Specific Procedure for the Preparation of Hydrazone 13 with R=4-hydroxy-3-methoxybenzene (See Scheme 3)

The intermediate 4-(2,5-dioxo-2,5-dihydro-pyrrol-1-yl)-benzoic acid hydrazide trifluoroacetic acid salt (6) was prepared as described in example 1, step E using the following quantities: derivative 4 (100 mg, 0.303 mmol), trifluoroacetic acid 250 µL, dichloromethane (1 mL). The intermediate 6 was dissolved in dichloromethane (2 mL) and treated with 4-hydroxy-3-methoxybenzaldehyde (vanillin, 46.1 mg, 0.303 mmol) and sodium bicarbonate (25.4 mg, 0.303 mmol). Dichloromethane (2-3 mL) was used to dissolve the aldehyde stuck to the reaction vessel wall. The reaction was stirred at room temperature for 12 hours. Afterwards, the reaction mixture was transferred into a separatory funnel containing ethyl acetate (50 mL). The organic phase was washed twice with 3% aqueous solution of sodium bicarbonate (2×20 mL) and with water (3×15 mL). The organic phase was dried with anhydrous magnesium sulfate, filtered and evaporated to the crude hydrazone 13, R=4-hydroxy-3-methoxybenzene (79 mg, 71%). The product was homogeneous by thin layer chromatography. $^1$H NMR (DMSO-d$_6$, δ ppm): 11.71 (br s, 1H, NH), 9.54 (br s, 1H, OH), 8.32 (br s, 1H, —CH=N—), 7.97 and 7.49 (2×d, J=8.2 Hz, 4H, aromatic), 7.32 (br s, 1H, aromatic), 7.21 (s, 2H, maleimide), 7.09 (br d, J=7.8 Hz, 1H, aromatic) 6.83 (d, J=8.2 Hz, 1H, aromatic), 3.82 (s, 3H, OCH$_3$).

Using iso-vanillin instead of vanillin the hydrazone 13 with R=4-methoxy-3-hydroxybenzene was obtained: $^1$H NMR (DMSO-d$_6$, δ ppm): 11.71 (br s, 1H, NH), 9.30 (br s, 1H, OH), 8.29 (br s, 1H, —CH=N—), 7.98 (d, J=8.2 Hz, 2H, aromatic), 7.49 (d, J=8.6 Hz, 2H, aromatic), 7.27 (d, J=1.5 Hz, 1H, aromatic), 7.22 (s, 2H, maleimide), 7.04 (dd, J=1.6 and 8.2 Hz, 1H, aromatic) 6.96 (d, J=8.2 Hz, 1H, aromatic, 3.80 (s, 3H, OCH$_3$).

Materials and Methods—Biology

In Vitro Studies (for Derivatives 4, 5, 8, 10, 11, and 12, etc.)

Cell culture—general: Biological assays were performed using the human monocytic cell line THP1, the murine macrophage-like cell lines J774A.1 and RAW 264.7, and the murine UBC cell lines MB49 and MB49-I. The cells were maintained in RPMI medium supplemented with 10% heat-inactivated fetal bovine serum (FBS) and containing 1 mM sodium pyruvate, 10 mM 4-(2-hydroxyethyl)piperazine-1-ethanesulfonic acid (HEPES) and 50 µg/mL gentamycin (referred as 10% FBS RPMI-1640). The cells were maintained at 37° C. in a moisture-saturated atmosphere containing 5% $CO_2$.

THP1 cells, RAW 264.7 cells and J774A.1 cells are the most widely used cell lines to investigate the function and differentiation of monocytes and macrophages in response to various inflammatory mediators.[17,18] Undifferentiated THP1 cells resemble primary monocytes/macrophages isolated from healthy donors or donors with inflammatory diseases, such as diabetes mellitus and atherosclerosis.[19] After treatment with phorbol esters, THP1 cells differentiate into macrophage-like cells which mimic native monocyte-derived macrophages in several respects.[20] As we previously described, green fluorescent protein-expressing (GFP)-THP1 cells were cultured for 18 h in 50 nM phorbol 12-myristate 13-acetate to induce monocyte-to-macrophage differentiation.[21-23] The cell lines RAW 264.7 and J774A.1 were kindly provided by Dr Tatiana Scorza (Université du Québec à Montréal, Canada). These cell lines are macrophage-like cell models which produce large amount of NO in response to IFNγ, TNFα, bacterial infection and bacterial products, such as lipopolysaccharide (LPS).[17] The cell line MB49-I is a highly invasive and tumorigenic UBC cell model that was developed by successive in vivo passages of MB49 primary tumors.[24]

Cell signaling studies: THP1-derived human macrophages ($750\times10^3$ cells/mL) and MB49-I cells ($500\times10^3$ cells/mL) were pretreated for 30 min with vehicle (DMSO), compounds 4 and 5, at 10, 25 or 50 μM; and then washed and recovered immediately (t=0 min) or after 30 min of activation with 50 U/mL IFNγ, 25 ng/mL IL6, or 10 ng/mL TNFα. Cell lysates were prepared and analyzed by immunoblotting as described.[21-23,25] Briefly, protein samples were resolved by SDS-PAGE under reducing conditions and transferred onto a PVDF membrane. Blots were first probed with rabbit polyclonal antibodies against phospho-STAT1 (pSTAT1), pSTAT3, or p-IκB (all at 1:2000) overnight at 4° C. Blots were then incubated with HRP-conjugated goat anti-rabbit IgG Ab (1:3000) for 1 h at room temperature. The same blots were stripped and then probed with anti-STAT1 or anti-STAT3 Abs (both at 1:1000). In both cases, probed molecules were visualized using an enhancement chemiluminescence detection kit (Thermo Fisher Scientific).

Luciferase assay. To assess the transcriptional activity of NFκB in response to TNFα, MB49-I cells cultured in monolayers ($7.5\times10^4$ cells/well in 24-well plates) were transiently transfected with an expression vector allowing the transcription of the firefly luciferase reporter gene under the control of CMV promoter and tandem repeats of the NFκB transcriptional response element. The luciferase gene encodes a 61-kDa enzyme that oxidizes D-luciferin in the presence of ATP, oxygen, and $Mg^{++}$, yielding a fluorescent product that can be quantified by measuring the released light. Transfection was performed using Opti-MEM reduced serum media and Lipofectamine 2000 (Thermo Fisher Scientific). Then, MB49-I cells were pretreated for 30 min with vehicle (DMSO) and compound 4 (at 10 μM or 30 μM); and then washed and recovered after 24 h of activation with 10 ng/mL or 50 ng/mL TNFα. Cell lysates were mixed with Luciferase assay reagent (a mixture of luciferine, coenzyme A, ATP and $Mg^{2+}$) and the light produced was measured using a luminometer.

Surface antigen expression analysis. To study membrane receptor expression, THP1-derived human macrophages ($750\times10^4$ cells/mL) were pretreated for 3 h with DMSO or compounds 4 and 5, and then left untreated (control) or treated for 48 h with 50 U/mL IFNγ. The expression level of MHC-II and CD40 was evaluated by flow cytometry as described.[21-23]

Motility assays. The in vitro scratch wound healing assay was performed to study the effects of compounds 4 and 5 in IL6-induced macrophage cell migration, as described.[26] Briefly, THP1-derived human macrophages ($750\times10^3$ cells/mL) were seeded into 24-well tissue culture plate to reach ~70-80% confluence as a monolayer. The cell monolayers were scraped in a straight line in one direction to create a "scratch" with a p200 pipet tip. To obtain the same field during the image acquisition, another straight line was scratched perpendicular to the first would line to create a cross in each well. Cell debris were removed and the edges of the scratch were smoothed by washing the cells once with 1 mL of Hank's buffer. Cell monolayers were pretreated for 3 h with vehicle (DMSO) or compounds 4 (10 μM) and 5 (25 μM), and then left untreated (control) or treated for 48 h with 25 ng/mL IL6. Using the cross as reference points the plate was placed under an inverted fluorescence microscope, and the images of the scratch were acquired at t=0 h and t=48 h. The number of motile cells was determined using Java-based image processing program ImageJ (National Institutes of Health) and relative cell motility was expressed as percent (%) of control of motile cells at t=48 h relative to motile cells within the initial wound (at t=0 h).

Microinvasion assays. Invasion was measured by assessment of human UBC T24 cell migration rate through an artificial basement membrane in a modified Boyden chamber (HTS Transwell System). Briefly, the membrane consisted of a polycarbonate filter with 0.4 μm pores diameter and was coated on ice with Matrigel (BD Biosciences) diluted 1:2 (v/v) in serum-free culture media. T24 cells ($50\times10^3$ cells) were seeded into the Matrigel coat in the upper well of the chamber, while polarized M1 macrophages ($50\times10^3$ cells) were seeded in the lower well. The polycarbonate filter with 0.4 μm pores diameter is too small to left the cells move to the bottom of the lower wells. Thus, non-invading cells into the matrigel coat were removed and cells that migrated down to the polycarbonate filter were stained with Hoescht 33258 dye after a 48-h incubation period, visualized by fluorescence microscopy and counted.

Cellular analysis of 3D spheroid-based tumor invasion assays. Cell preparation and spheroid formation were performed following the manufacturer instructions (Corning). Briefly, MDA-MB-231 cells were harvested and diluted to a concentration of $5\times10^4$ cells/mL in (complete) culture media supplemented with 10% serum. 100 μL of cell suspension was then pipetted to appropriate 96 well spheroid formation plate and placed at 37° C./5% $CO_2$. Spheroid formation was monitored every 24 hours. The typical cell aggregation period was 48 hours. Upon spheroid formation completion, 70 μL of complete medium was removed from each well, and replaced by 70 μL of serum-free medium. This was repeated on a daily basis to create a serum starvation period of 48 hours. Matrigel matrix (100 μL) was then added to each well. The plate was centrifuged at 300×g for 5 minutes in a swinging bucket centrifuge. The plate was then transferred to a 37° C./5% CO2 incubator for one hour to initiate gel formation. Following the 1-hour gel formation incubation period, DMSO or compound 4 was added to appropriate wells during 60 minutes. After pretreatment, the media was removed and replaced by complete culture media, and then the media was changed every day for a period of 4 days. Brightfield images at day 0 and day 4 was used to measure invasive protrusion (invadopodia) extending away from the tumoroid and into the extracellular matrix. The role of these protrusions is the breakdown of Matrigel matrix, thus aiding the invasion process. These protrusions were identified, and their area and perimeter properly quantified using the ImageJ software (National Institutes of Health).

Evaluation of NO and Urea production by chemical methods. The MB49-I cells and the J774A.1 cells ($25 \times 10^3$ cells/well) were grown and pretreated, as indicated, with various anti-inflammatory derivatives, precursors and mono-functional derivatives for a period of 3 h. Afterwards the cells were washed twice with 10% FBS RPMI-1640 and then activated to produce NO for a period of 24 h with cytokines INFγ and TNFα. NO production was measured using the Griess reagent method as previously described.[27] This method involves the detection of nitrite ions ($NO_2^-$) formed by the spontaneous oxidation of NO under physiological conditions. According the manufacture procedure (Life Technologies; # G-7921), equal volumes of sulfanilic acid and N-(1-naphthyl)ethylenediamine are mixed together to form the Griess reagent. In the presence of $NO_2^-$, sulfanilic acid is converted to a diazonium salt, which in turn is coupled to N-(1-naphthyl)ethylenediamine to produce a pink coloration that is measured with a spectrophotometer (Biotek, synergy HT) at 548 nm. In the same manner, urea synthesis through arginase-1 activity was measured using commercially available kit.

Evaluation of cell proliferation by the MTT assay. To evaluate the anti-proliferative activity, cell viability/proliferation MTT assays were performed as previously described.[21-23,25,28] Briefly, MB49-I cells ($5 \times 10^3$ cells/well) were plated in 96-well plates in 100 µL 10% FBS RPMI-1640 and cultured for 24 h at 37° C. and 5% $CO_2$. Cells were pretreated for a period of 3 h with vehicle (DMSO) or derivatives 1 and 1A at 0, 10, 25, 37.5, and 50 µM, and then incubated for 24 h in the absence or the presence of INFγ and TNFα. At the end of the culture period, 10 µL of 5 mg/mL methylthiazolyldiphenyl-tetrazolium bromide (MTT) solution was added to each well. After a 3-h incubation period with MTT reagent, 100 µL of MTT solubilization buffer (10% SDS in 10 mM HCl) was added and plates were placed overnight in the cell incubator before absorbance measure. The optical density was read at 580 nm using the Microplate Reader Manager (from Bio-Rad Laboratories).

Statistical analyses. For all biological assays, data were presented as mean±SD from three independent experiments. Data were analyzed by one-way ANOVA followed by Bonferonni post-test using Prism software, version 3.03 (GraphPad, San Diego, Calif.). p values of ≤0.05 were considered to indicate statistical significance.

In Vivo Studies (for Derivatives 4 and 8)

Ectopic UBC model. Male C57BL/6J mice (6-8 weeks old), each weighing 15-18 g, were used for the experiments (supplied by Charles River). The mice were housed with free access to food and water on a 12:12 h light:dark cycle with the room temperature maintained at 21° C. MB49 cells, MB49-I cells, and iNOS-deficient MB49-I cells ($5 \times 10^4$ in 100 µL PBS) were injected subcutaneously (s.c.) into the right flank of the mice. Growth rates of the s.c. tumors were monitored. The size of tumors was determined every 3 days for 24-28 days using a digital caliper and by measuring luciferin luminescence at days 15 and 25 using the IVIS imaging system. A blinded observer measured tumor length and width. The volume of the tumor was calculated from the formula: Length×width2×0.52, where length and width were tumor diameters measured with calipers in mutually perpendicular directions. At a tumor size of approximately 10 mm³ the mice were divided into different groups. A control group received PBS as treatment. As indicated, other groups were treated at different doses (90, 150 or 300 µM) with an intraperitoneal (i.p.) injection of compounds 4 or 8 every 3-4 days for 18-20 days.[24,27]

Orthotopic UBC model. Female C57BL/6J mice (6-8 weeks old), each weighing 15-18 g, were anesthetized and a 24-gauge Teflon catheter was introduced into the bladder lumen through the urethra. To prepare the bladder for tumor implantation, a point lesion was induced in the bladder wall by electrocauterization. Then, $1 \times 10^5$ of MB49-I cells in 100 µl of PBS were instilled into the bladder. When indicated, control mice were electrocauterized and PBS was instilled into the bladder. Syringes containing the cell suspension were maintained into the catheter for 20 min to allow cell attachment to the bladder wall.[24,27]

Statistical analyses. Mann-Whitney test was used to compare tumor growth, using Prism software, version 3.03 (GraphPad, San Diego, Calif.). p values of ≤0.05 were considered to indicate statistical significance.

The results from the in vitro and in vivo experiments are presented in FIGS. 1 to 25.

REFERENCES

1. LaFond, R. In *Cancer: The outlaw cell*, 3$^{rd}$ Ed., ACS publication, Washington, D.C., 384 pages (2012)
2. Alderton G K. The tumor microenvironment drives metastasis, *Nat. Rev. Cancer* 16, 199 (2016)
3. Steeg P S. Targeting metastasis, *Nat. Rev. Cancer* 16, 201-218 (2016)
4. Baumann M, Krause M, Overgaard J, Debus J, Bentzen S M, Daartz J, Richter C, Zips D, Bortfeld T. Radiation oncology in the era of precision medicine, *Nat. Rev. Cancer* 16, 234-249 (2016)
5. Vanneman M, Dranoff G. Combining immunotherapy and targeted therapies in cancer treatment, *Nat. Rev. Cancer* 12, 237-251 (2012)
6. Scott A M, Wolchok J D, Old L J. Antibody therapy of cancer. *Nat. Rev. Cancer* 12, 278-287 (2012)
7. Phillips A P, Mentha J W. U.S. Pat. No. 3,046,301 (Oct. 29, 1959); Deglin J H, Vallerand A H. In *Guide des médicaments*, ERPI, pp. 424-427 (1995)
8. Remers, W A. Antineoplastic agents, In *Wilson and Gisvold's Textbook of organic Medicinal and pharmaceutical chemistry*, 9$^{th}$ Ed., Delgado J N, Remers, W A. J. B. Eds, Lippincott, N.Y., Chapter 8, 321-322 (1989)
9. Lau A, Berube G, Ford C H J. Conjugation of doxorubicin to monoclonal anti-carcinoembryonic antigen antibody via novel thiol-directed cross-linking reagents, *Bioorg. Med. Chem.*, 3, 1299-1304 (1995)
10. Lau A, Berube G, Ford C H J, Gallant M. Novel doxorubicin-monoclonal anti-carcinoembryonic antigen antibody immunoconjugate activity in vitro, *Bioorg. Med. Chem.*, 3, 1305-1312 (1995)
11. Hamelin-Morrissette J, Cloutier S, Girouard J, Belgorosky D, Eiján A-M, Legault J, Reyes-Moreno C, and Bérubé G. Identification of an anti-inflammatory derivative with anti-cancer potential: The impact of each of its structural components on inflammatory responses in macrophages and bladder cancer cells, *Eur. J. Med. Chem.*, 96, 259-269 (2015)
12. Taha M, Ismail N H Lalani S, Fatmi M Q, Atia-tul-Wahab, Siddiqui S, Khan K M, Imran S, Choudhary M I. Synthesis of novel inhibitors of a-glucosidase based on the benzothiazole skeleton containing benzohydrazide moiety and their molecular docking studies, *Eur. J. Med. Chem.*, 92, 387-400 (2015)

13. Perrin D D, Armarego C F. In *Purification of Laboratory Chemicals*, 3rd Ed., Pergamon Press, Oxford, New York (1988)
14. Still W C, Kahn M, Mitra A. Rapid chromatographic technique for preparative separations with moderate resolution, *J. Org. Chem.*, 43, 2923-2925 (1978)
15. Willner D, Trail P A, Hofstead S J, King H D, Lasch S J, Braslawsky G R, Greenfield R S, Kaneko T, Firestone R A. (6-Maleimidocaproyl)hydrazone of doxorubicin. A new derivative for the preparation of immunoconjugates of doxorubicin, *Bioconjug. Chem.*, 4, 521-527 (1993)
16. Heindel N D, Zhao H R, Egolf R A, Chang C H, Schray K J, Emrich J G, McLaughlin J P, Woo D V, A novel heterobifunctional linker for formyl to thiol coupling, *Bioconjug. Chem.*, 2, 427-430 (1991)
17. Lemaire S, Mingeot-Leclercq M P, Tulkens P M, Van Bambeke F. Study of macrophage functions in murine J774 cells and human activated THP-1 cells exposed to oritavancin, a lipoglycopeptide with high cellular accumulation, *Antimicrobial agents and chemotherapy*, 58 2059-2066 (2014)
18. Auwerx J, The human leukemia cell line, THP-1: A multifacetted model for the study of monocyte-macrophage differentiation, *Experientia*, 47, 22-31 (1991)
19. Qin Z, The use of THP-1 cells as a model for mimicking the function and regulation of monocytes and macrophages in the vasculature, *Atherosclerosis*, 221, 2-11 (2012)
20. Daigneault M, Preston J A, Marriott H M, Whyte M K, Dockrell D H. The identification of markers of macrophage differentiation in PMA-stimulated THP-1 cells and monocyte-derived macrophages, *PloS one*, 5, 0008668 (2010)
21. Dufresne M, Dumas G, Asselin E, Carrier C, Pouliot M, Reyes-Moreno C, Pro-inflammatory type-1 and anti-inflammatory type-2 macrophages differentially modulate cell survival and invasion of human bladder carcinoma T24 cells, *Mol. Immunol.*, 48 1556-1567 (2011)
22. Dumas G, Dufresne M, Asselin E, Girouard J, Carrier C, Reyes-Moreno C. CD40 pathway activation reveals dual function for macrophages in human endometrial cancer cell survival and invasion, *Cancer Immunol. Immunother.*, 62, 273-283, (2013)
23. Dallagi A, Girouard J, Hamelin-Morrissette J, Dadzie R, Laurent L, Vaillancourt C, Lafond J, Carrier C, Reyes-Moreno C. The activating effect of IFN-gamma on monocytes/macrophages is regulated by the LIF-trophoblast-IL-10 axis via Stat1 inhibition and Stat3 activation, *Cell. Mol. Immunol.*, 12, 326-341 (2015).
24. Fabris V T, Lodillinsky C, Pampena M B, Belgorosky D, Lanari C, Eijan A M. Cytogenetic characterization of the murine bladder cancer model MB49 and the derived invasive line MB49-I, *Cancer Genet.*, 205, 168-176 (2012).
25. Leduc, Bourassa V, Asselin E, Leclerc P, Lafond, Reyes-Moreno C. Leukemia Inhibitory Factor Regulates Differentiation of Trophoblast-Like BeWo Cells Through the Activation of JAK/STAT and MAPK3/1 MAP Kinase-Signaling Pathways, *Biol. Reprod.*, 86, 54, 1-10 (2012)
26. Menon M B, Ronkina N, Schwermann J, Kotlyarov A, Gaestel M. Fluorescence-based quantitative scratch wound healing assay demonstrating the role of MAP-KAPK-2/3 in fibroblast migration, *Cell. Motil. Cytoskeleton*, 66, 1041-1047 (2009)
27. Belgorosky D, Langle Y, Prack Mc Cormick B, Colombo L, Sandes E, Eijan A. M. Inhibition of nitric oxide is a good therapeutic target for bladder tumors that express iNOS, *Nitric Oxide*, 36, 11-18 (2014)
28. Carmichael J, Degraff W G, Gazdar A F, Minna J D, Mitchell J D. Evaluation of a tetrazolium-based semiautmated colorimetric assay: Assessment of radiosensitivity. *Cancer Res.*, 47, 943-946 (1987)

The present disclosure has been described with regard to specific examples. The description was intended to help the understanding of the present disclosure, rather than to limit its scope. It will be apparent to one skilled in the art that various modifications may be made to the present disclosure without departing from the scope of the present disclosure as described herein, and such modifications are intended to be covered by the present document.

The invention claimed is:
1. A compound of formula (I):

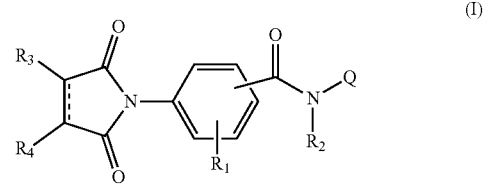

wherein:
$R_1$ is H, alkyl or halogen;
$R_2$ is H, or a substituted or unsubstituted member chosen from acetyl, propiolyl, butyryl, isobutyryl and benzoyl;
Q is $Q_A$ or $Q_B$,
$Q_A=$

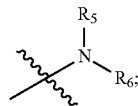

$Q_B=$

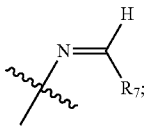

=a single bond or a double bond;
$R_5$ is H, or a substituted or unsubstituted member chosen from acetyl, propiolyl, butyryl and isobutyryl;
$R_6$ is Boc, or a substituted or unsubstituted member chosen from acetyl, propiolyl, butyry and isobutyryl;
$R_7$ is a substituted or unsubstituted member chosen from $C_1$-$C_8$ alkyl, $C_3$-$C_8$ cycloalkyl, phenyl, furanyl, thiophenyl, pyridinyl, naphthyl, quinolyl and isoquinolyl;

$R_3$ and $R_4$ are independently chosen from H, —$SR_8$ and $NR_9R_{10}$;

$R_8$ is H, $C_1$-$C_8$ alkyl, —$(CH_2)_n$NHBoc, or —$(CH_2)_n$$NH_2$ wherein n=1 to 6;

$R_9$ is H or $C_1$-$C_8$ alkyl;

$R_{10}$ is H, $C_1$-$C_8$ alkyl, acetyl, propiolyl, butyryl, isobutyryl, or benzoyl;

wherein $R_2$, $R_5$, $R_6$ and $R_7$, when substituted, are substituted with at least one substituent chosen from —$OR_8$, —F, —Cl, —Br, —I, acetyl, propiolyl, butyryl, isobutyryl, benzoyl, —$NO_2$, $C_1$-$C_8$ alkyl, methoxycarbonyl-, or alkyloxycarbonyl-;

or an enantiomer, diastereoisomer, racemic mixture, pharmaceutically acceptable salt, solvate or prodrug thereof, with the proviso that the compound is different from

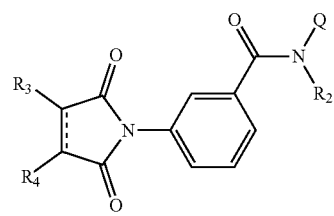

2. The compound of claim 1, wherein said compound is a compound of formula (IA):

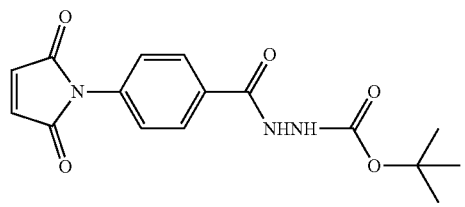

(IA)

wherein $R_2$, $R_3$, $R_4$ and Q are as defined in claim 1 and wherein is a double bond.

3. The compound of claim 2, wherein $R_2$ is H, unsubstituted member chosen from acetyl and propiolyl;

Q is $Q_A$;

$R_5$ is H, unsubstituted member chosen from acetyl and propiolyl; and $R_6$ is Boc, or an unsubstituted member chosen from acetyl and propiolyl.

4. The compound of claim 1, wherein said compound is a compound of formula (IB):

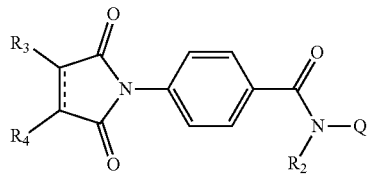

(IB)

wherein $R_2$, $R_3$, $R_4$ and Q are as defined in claim 1 and wherein is a double bond.

5. The compound of claim 4, wherein $R_2$ is H, unsubstituted member chosen from acetyl and propiolyl;

Q is $Q_A$;

$R_5$ is H, unsubstituted member chosen from acetyl and propiolyl; and $R_6$ is Boc, or an unsubstituted member chosen from acetyl and propiolyl.

6. The compound of claim 1, wherein said compound is a compound of formula (IC):

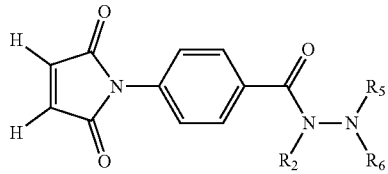

(IC)

wherein $R_2$, $R_5$ and $R_6$ are as defined in claim 1.

7. The compound of claim 6, wherein $R_2$ is H, unsubstituted member chosen from acetyl and propiolyl;

Q is $Q_A$;

$R_5$ is H, unsubstituted member chosen from acetyl and propiolyl; and $R_6$ is Boc, or an unsubstituted member chosen from acetyl and propiolyl.

8. The compound of claim 1, wherein said compound is a compound of formula (ID):

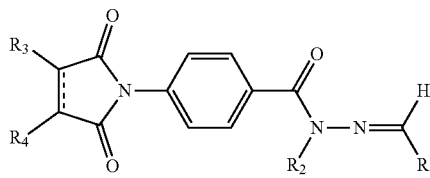

(ID)

wherein $R_2$, $R_3$, $R_4$ and $R_7$ are as defined in claim 1 and wherein $$||$$

is a double bond.

9. The compound of claim 8, wherein $R_2$ is H or unsubstituted member chosen from acetyl and propiolyl; and $R_7$ is an unsubstituted member chosen from $C_1$-$C_8$ alkyl, $C_3$-$C_6$ cycloalkyl, phenyl, furanyl, thiophenyl, pyridinyl, naphthyl, quinolyl and isoquinolyl.

10. The compound of claim 1, wherein said compound is a compound of formula (IE):

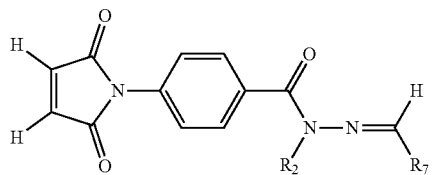

(IE)

wherein $R_2$ and $R_7$ are as defined in claim 1.

11. The compound of claim 10, wherein $R_2$ is H or an unsubstituted member chosen from acetyl and propiolyl; and $R_7$ is an unsubstituted member chosen from $C_1$-$C_8$ alkyl, $C_3$-$C_6$ cycloalkyl, phenyl, furanyl, thiophenyl, pyridinyl, naphthyl, quinolyl and isoquinolyl.

12. The compound of claim 1, wherein said compound is chosen from:

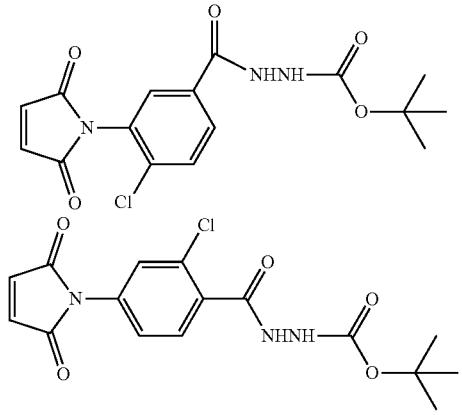

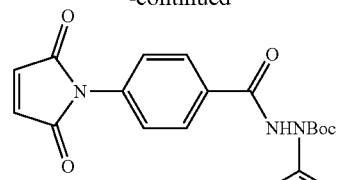

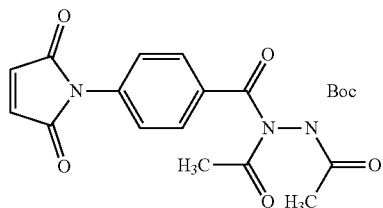

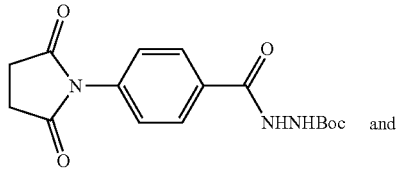

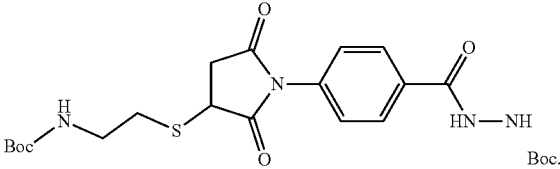

13. The compound of claim 1, wherein said compound is chosen from:

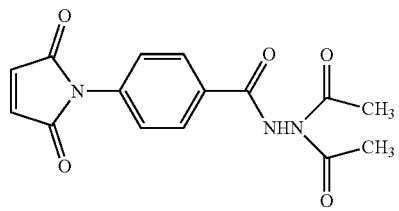

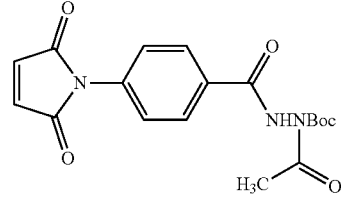

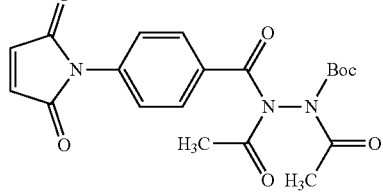

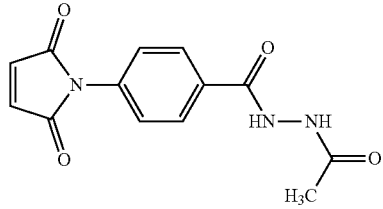

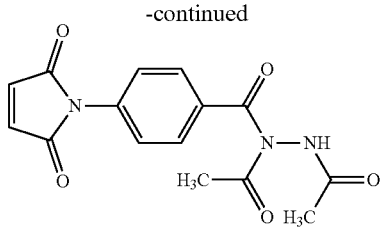
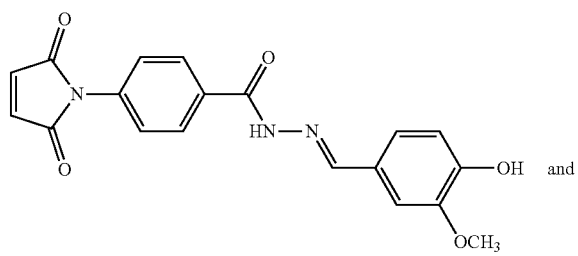 and
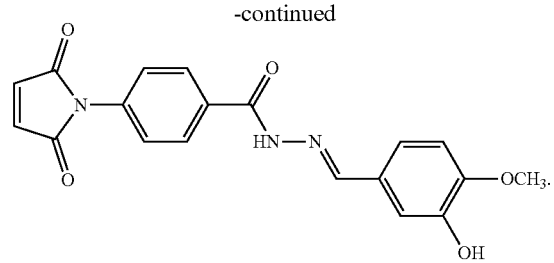
14. The compound of claim 10, wherein
$R_2$ is H or an unsubstituted member chosen from acetyl and propiolyl; and
$R_7$ is a phenyl substituted with at least one substituent —$OR_9$.
15. The compound of claim 10, wherein
$R_2$ is H; and
$R_7$ is a phenyl substituted with at least one substituent —$OR_9$ in which $R_9$ is H, and with at least one substituent —$OR_9$ in which $R_9$ is $C_1$-$C_8$ alkyl.
* * * * *